(12) United States Patent
Vu et al.

(10) Patent No.: US 7,632,845 B2
(45) Date of Patent: Dec. 15, 2009

(54) PHENYL QUINOLINES AND THEIR USE AS ESTROGENIC AGENTS

(75) Inventors: An Thien Vu, Pottstown, PA (US); Stephen Todd Cohn, Reading, PA (US); Richard Eric Mewshaw, King of Prussia, PA (US)

(73) Assignee: Wyeth, Madison, NJ (US)

( * ) Notice: Subject to any disclaimer, the term of this patent is extended or adjusted under 35 U.S.C. 154(b) by 339 days.

(21) Appl. No.: 11/443,861

(22) Filed: May 31, 2006

(65) Prior Publication Data

US 2006/0217399 A1    Sep. 28, 2006

Related U.S. Application Data

(63) Continuation of application No. 10/846,216, filed on May 13, 2004, now Pat. No. 7,084,276.

(60) Provisional application No. 60/471,436, filed on May 16, 2003.

(51) Int. Cl.
    *A61K 31/47* (2006.01)
(52) U.S. Cl. .................................................. 514/311
(58) Field of Classification Search ................ 546/173, 546/179; 514/311
    See application file for complete search history.

(56) References Cited

U.S. PATENT DOCUMENTS

| 4,418,068 | A   | 11/1983 | Jones ........................ 514/337 |
| 5,126,351 | A   | 6/1992  | Luzzio et al. ................ 514/291 |
| 5,998,402 | A   | 12/1999 | Miller et al. ................. 514/183 |
| 7,084,276 | B2* | 8/2006  | Vu et al. ..................... 546/173 |

FOREIGN PATENT DOCUMENTS

| EP | 0 835 867 A1 | 4/1998 |
| WO | 01/24785 A2 | 4/2001 |
| WO | 02/04418 A2 | 1/2002 |
| WO | 02/094268 AL | 11/2002 |
| WO | 02/094788 AL | 11/2002 |
| WO | 03/051805 A2 | 6/2003 |
| WO | 03/051860 A2 | 6/2003 |

OTHER PUBLICATIONS

Lacreuse, Physiology & behavior, vol. 96, pp. 448-456, 1009.*
Radjabian CA 143:373009, abstract only of Faslnamah-i Giyahan-i Daruyi, vol. 4(Suppl. 1), pp. 33-41, 2005.*
Al-Azzawi, F., "The menopause and its treatment in perspective," Postgraduate Medical Journal 77: 292-304 (2001).
Bhat, R. A. et al., "A Novel Human Estrogen Receptor β: Identification and Functional Analysis of Additional N-terminal Amino Acids," Journal of Steroid Biochemistry & Molecular Biology 67: 233-240 (1998).
Black, L. J. et al., "Uterine Bioassay of Tamoxifen, Trioxifene and a New Estrogen Antagonist (LY117018) in Rats and Mice," Life Sciences, 26, 1453 (1980).
Brincat, M. P., "Hormone replacement therapy and the skin," Maturitas 35: 107-117 (2000).
Calvin, M., "Oestrogens and Wound Healing," Maturitas 34: 195-210 (2000).
Chemical Abstract Service; Lakhani, R. R. et al., Database Accession No. 1992:448192; RN 141853-28-3; 141853-36-3; 141853-44-3; 141853-52-3 abstract &Acta Ciencia Indica, Chemistry, 1991, 17C(1): 47-54.
Chemical Abstracts Service; Gyul 'budagyan, L. V. et al., Database Accession No. 1969:28794; RN 21202-81-3; 21202-99-3; 21203-00-9; 21203-01-0; 21203-02-1; 21203-03-2 abstract & Armyanskii Khimicheskii Zhurnal, 1968, 21(5): 418-21.
Chemical Abstracts Service; Hamana, M. et al., Database Accession No. 1977:567845; RN 64388-10-9 abstract & Chemical & Pharmaceutical Bulletin, 1977, 25(6): 1256-64.
Chemical Abstracts Service; Lakhani, R. R. et al., Database Accession No. 1998:549419; RN 116720-97-9; 116721-05-2; 116721-13-2; 116721-21-2 abstract & Journal of the Indian Chemical Society, 1988, 65(3): 197-9.
Chemical Abstracts Service; Lakhani, R. R. et al., Database Accession No. 1988:549314; RN 116734-27-1; 116734-35-1 abstract & Journal of the Institution of Chemists (India), 1987, 59(5): 230-2.
Couse, J. F. et al., "Tissue Distribution and Quantitative Analysis of Estrogen Receptor-α(ERα) and Estrogen Receptor-β(ERβ) Messenger Ribonucleic Acid in the Wild-Type and ERα-Knockout Mouse," Endocrinology 138: 4613-4621 (1997).
Cowley, S. M. et al., "Estrogen Receptors α and β Form Heterodimers on DNA," Journal of Biological Chemistry 272: 19858-19862 (1997).
Crandall, C. J. "Estrogen Replacement Therapy and Colon Cancer: A Clinical Review," Journal of Womens Health & Gender Based Medicine 8: 1155-1166 (1999).

(Continued)

*Primary Examiner*—D. Margaret Seaman
(74) *Attorney, Agent, or Firm*—Pepper Hamilton LLP

(57) ABSTRACT

This invention provides estrogen receptor modulators of formula I, having the structure

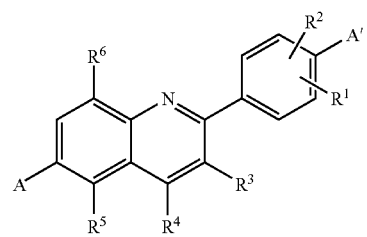

wherein,
$R^1$, $R^2$, $R^3$, $R^4$, $R^5$, and $R^6$ are as defined in the specification, or a N-oxide thereof or a pharmaceutically acceptable salt thereof or a prodrug thereof.

1 Claim, No Drawings

OTHER PUBLICATIONS

Epperson, C. N. et al., "Gonadal Steroids in the Treatment of Mood Disorders," Psychosomatic Medicine 61: 676-697 (1999).

Finking, G. et al., "Die Wirkungen von Östrogen im kardiovaskulären System," Zeitschrift fur Kardiologie 89: 442-453 (2000) (English abstract included).

Fitzpatrick, S. L. et al., "Expression of Estrogen Receptor-β Protein in Rodent Ovary," Endocrinology 140: 2581-2591(1999).

Goldstein, S. R. et al., "A Pharmacological review of selective oestrogen receptor modulators," Human Reproduction Update 6: 212-224 (2000).

Green, S. et al., "Human oestrogen receptor cDNA: sequence, expression and homology to v-*erb*-A," Nature 320: 134-9 (1986).

Hall, J. M. et al., "The Multifaceted Mechanisms of Estradiol and Estrogen Receptor Signaling," Journal of Biological Chemistry 276: 36869-36872 (2001).

Hurn, P. D. et al., "Estrogen as a Neuroprotectant in Stroke," Journal of Cerebral Blood Flow & Metabolism 20: 631-652 (2000).

Kuiper, G. et al., "Cloning of a novel estrogen receptor expressed in rat prostate and ovary," Proceedings of the National Academy of Sciences of the United States of America 93: 5925-5930 (1996).

Kuiper, G. et al., "Comparison of the Ligand Binding Specificity and Transcript Tissue Distribution of Estrogen Receptors α and β," Endocrinology 138: 863-870.

Levin, E. R. "Cellular Functions of the Plasma Membrane Estrogen Receptor," Trends in Endocrinology & Metabolism 10: 374-377 (1999).

Levin, E. R., "*Genome and Hormones: Gender Differences in Physiology* Invited Review: Cell localization, physiology, and nongenomic actions of estrogen receptors," Journal of Applied Physiology 91: 1860-1867 (2001).

McDonnell, D. P., "Selective Estrogen Receptor Modulators (SERMs): A First Step in the Development of Perfect Hormone Replacement Therapy Regimen," Journal of the Society for Gynecologic Investigation 7: S10-S15 (2000).

McDonnell, D. P., Principles Of Molecular Regulation, Ch. 20, Humana Press,. pp. 351-361(2000) Totowa, New Jersey.

McKenna, N. J. et al., "Nuclear Receptor Coregulators: Cellular and Molecular Biology," Endocrine Reviews 20: 321-344 (1999).

Mendelsohn, M. E. et al., "The Protective Effects of Estrogen on the Cardiovascular System," New England Journal of Medicine 340: 1801-1811 (1999).

Meyers, Marvin J, et al., "Estrogen Receptor Subtype-Selective Ligands: Asymmetric Synthesis and Biological Evaluation of cis- and trans-5,11-Dialkyl-5,6,11,12-tetrahydrochrysenes," *J. Med. Chem.* (1999), 42(13), 2456-2468.

Moggs, J. G. et al., "Estrogen receptors: orchestrators of pleiotropic cellular responses," EMBO Reports 2: 775-781 (2001).

Monk, D. et al., "Use of Estrogens for the Prevention and Treatment of Alzhimer's Disease," Dementia & Cognitive Geriatric Disorders 11: 1-10 (2000).

Monyer, H. et al., "Glucose deprivation neuronal injury in cortical culture," 1989, Brain Research 483:347-354.

Paige, et al., "Estrogen receptor (ER) modulators each induce distinct conformational changes in ER αand ER β," Proceedings of the National Academy of Sciences of the United States of America 96: 3999-4004 (1999).

Peele, D. B. et al., "Effects of Selection Delays on Radial Maze Performance: Acquisition and Effects of Scopolamine," Pharmacology, Biochemistry, and Behavior, 29:143-150, (1988)

Pelzer, T. et al., "Estrogen Effects in the Myocardium: Ihibition of NF-κB DNA Binding by Estrogen Receptor-α and -β," Biochemical & Biophysical Research Communications 286: 1153-7 (2001).

Pike, A. C. W. et al., "Structure of the ligand-binding domain of oestrogen receptor beta in the presence of a partial agonist and a full antagonist," Embo 18: 4608-4618 (1999).

Quaedackers, M. E. et al., "4-Hydroxytamoxifen Trans-Represses Nuclear Factor-κB Activity in Human Osteoblastic U2-OS Cells through Estrogen Receptor (ER)α, and Not through ERβ," Endocrinology 142: 1156-1166 (2001).

Sar, M. et al., "Differential Expression of Estrogen Receptor-β and Esrogen Receptor-α in the Rat Ovary," Endocrinology 140: 963-971 (1999).

Shiau, A. K. et al.,"The Structural Basis of Estrogen Receptor/Coactivator Recognition and the Antagonism of This Interaction by Tamoxifen," Cell 95: 927-937 (Dec. 23, 1998).

Swenson, R. E. et al., "Synthesis of Substituted Quinolines Using the Dianion Addition of *N*-Boc-anilines and α-Tolylsulfonyl- α,β-unsaturated Ketones," *Journal of Organic Chemistry*, 2002, 67(26): 9182-9185

Syeda Huma, H. Z. et al., "Cu(I)-catalyzed three component coupling protocol for the synthesis of quinoline derivatives," *Tetrahedron Letters*, 2002, 43(36): 6485-6488.

Teo, C. et al., "Synthesis of 2-(p-Chlorobenzyl)-3-aryl-6-methoxybenzofurans as Selective Ligands for Antiestrogen-Binding Sites. Effects on Cell Proliferation and Cholesterol Synthesis," *J Med Chem*, 1992, 35: 1330-1339.

Wallace, 0. B. et al., "Tetrahydroquinoline-Based Selective Estrogen Receptor Modulators (SERMs)," *Bioorganic & Medicinal Chemistry Letters*, 2003, 13(11): 1907-1910.

Wroblewski, F. et al. "Lactic Dehydrogenase Activity in Blood," 1955, Proc. Soc. Exp. Biol. Med. 90:210-213.

Yagi K., "Short Communications —A Simple Fluorometric Assay for Lipoperoxide in Blood Plasma," Biochem Med 15:212-216 (1976).

\* cited by examiner

PHENYL QUINOLINES AND THEIR USE AS ESTROGENIC AGENTS

CROSS-REFERENCE TO RELATED APPLICATIONS

The present application is a continuation of U.S. application Ser. No. 10/846,216, filed May 13, 2004 and also claims benefit to U.S. Provisional Application Ser. No. 60/471,436, filed May 16, 2003, each of which is incorporated herein by reference in its entirety.

FIELD OF THE INVENTION

This invention relates to phenyl quinoline compounds, their use as estrogenic agents, and methods of their preparation.

BACKGROUND OF THE INVENTION

The pleiotropic effects of estrogens in mammalian tissues have been well documented, and it is now appreciated that estrogens affect many organ systems [Mendelsohn and Karas, New England Journal of Medicine 340: 1801-1811 (1999), Epperson, et al., Psychosomatic Medicine 61: 676-697 (1999), Crandall, Journal of Womens Health & Gender Based Medicine 8: 1155-1166 (1999), Monk and Brodaty, Dementia & Geriatric Cognitive Disorders 11: 1-10 (2000), Hurn and Macrae, Journal of Cerebral Blood Flow & Metabolism 20: 631-652 (2000), Calvin, Maturitas 34: 195-210 (2000), Finking, et al., Zeitschrift fur Kardiologie 89: 442-453 (2000), Brincat, Maturitas 35: 107-117 (2000), Al-Azzawi, Postgraduate Medical Journal 77: 292-304 (2001)]. Estrogens can exert effects on tissues in several ways. Probably, the most well characterized mechanism of action is their interaction with estrogen receptors leading to alterations in gene transcription. Estrogen receptors are ligand-activated transcription factors and belong to the nuclear hormone receptor superfamily. Other members of this family include the progesterone, androgen, glucocorticoid and mineralocorticoid receptors. Upon binding ligand, these receptors dimerize and can activate gene transcription either by directly binding to specific sequences on DNA (known as response elements) or by interacting with other transcription factors (such as AP1), which in turn bind directly to specific DNA sequences [Moggs and Orphanides, EMBO Reports 2: 775-781 (2001), Hall, et al., Journal of Biological Chemistry 276: 36869-36872 (2001), McDonnell, Principles Of Molecular Regulation. p 351-361 (2000)]. A class of "coregulatory" proteins can also interact with the ligand-bound receptor and further modulate its transcriptional activity [McKenna, et al., Endocrine Reviews 20: 321-344 (1999)]. It has also been shown that estrogen receptors can suppress NFκB-mediated transcription in both a ligand-dependent and independent manner [Quaedackers, et al., Endocrinology 142: 1156-1166 (2001), Bhat, et al., Journal of Steroid Biochemistry & Molecular Biology 67: 233-240 (1998), Pelzer, et al., Biochemical & Biophysical Research Communications 286: 1153-7 (2001)].

Estrogen receptors can also be activated by phosphorylation. This phosphorylation is mediated by growth factors such as EGF and causes changes in gene transcription in the absence of ligand [Moggs and Orphanides, EMBO Reports 2: 775-781 (2001), Hall, et al., Journal of Biological Chemistry 276: 36869-36872 (2001)].

A less well-characterized means by which estrogens can affect cells is through a so-called membrane receptor. The existence of such a receptor is controversial, but it has been well documented that estrogens can elicit very rapid non-genomic responses from cells. The molecular entity responsible for transducing these effects has not been definitively isolated, but there is evidence to suggest it is at least related to the nuclear forms of the estrogen receptors [Levin, Journal of Applied Physiology 91: 1860-1867 (2001), Levin, Trends in Endocrinology & Metabolism 10: 374-377 (1999)].

Two estrogen receptors have been discovered to date. The first estrogen receptor was cloned about 15 years ago and is now referred to as ERα [Green, et al., Nature 320: 134-9 (1986)]. The second was found comparatively recently and is called ERβ [Kuiper, et al., Proceedings of the National Academy of Sciences of the United States of America 93: 5925-5930 (1996)]. Early work on ERβ focused on defining its affinity for a variety of ligands and, indeed, some differences with ERα were seen. The tissue distribution of ERβ has been well mapped in the rodent and it is not coincident with ERα. Tissues such as the mouse and rat uterus express predominantly ERα, whereas the mouse and rat lung express predominantly ERβ [Couse, et al., Endocrinology 138: 4613-4621 (1997), Kuiper, et al., Endocrinology 138: 863-870 (1997)]. Even within the same organ, the distribution of ERα and ERβ can be compartmentalized. For example, in the mouse ovary, ERβ is highly expressed in the granulosa cells and ERα is restricted to the thecal and stromal cells [Sar and Welsch, Endocrinology 140: 963-971 (1999), Fitzpatrick, et al., Endocrinology 140: 2581-2591 (1999)]. However, there are examples where the receptors are coexpressed and there is evidence from in vitro studies that ERα and ERβ can form heterodimers [Cowley, et al., Journal of Biological Chemistry 272: 19858-19862 (1997)].

The most potent endogenous estrogen is 17β-estradiol. A large number of compounds have been described that either mimic or block the activity of 17β-estradiol. Compounds having roughly the same biological effects as 17β-estradiol are referred to as "estrogen receptor agonists". Those which block the effect of 17β-estradiol, when given in combination with it, are called "estrogen receptor antagonists". In reality, there is a continuum between estrogen receptor agonist and estrogen receptor antagonist activity and some compounds behave as estrogen receptor agonists in some tissues but estrogen receptor antagonists in others. These compounds with mixed activity are called selective estrogen receptor modulators (SERMS) and are therapeutically useful agents (e.g. EVISTA) [McDonnell, Journal of the Society for Gynecologic Investigation 7: S10-S15 (2000), Goldstein, et al., Human Reproduction Update 6: 212-224 (2000)]. The precise reason why the same compound can have cell-specific effects has not been elucidated, but the differences in receptor conformation and/or in the milieu of coregulatory proteins have been suggested.

It has been known for some time that estrogen receptors adopt different conformations when binding ligands. However, the consequence and subtlety of these changes only recently has been revealed. The three dimensional structures of ERα and ERβ have been solved by co-crystallization with various ligands and clearly show the repositioning of helix 12 in the presence of an estrogen receptor antagonist, which sterically hinders the protein sequences required for receptor-coregulatory protein interaction [Pike, et al., Embo 18: 4608-4618 (1999), Shiau, et al., Cell 95: 927-937 (1998)]. In addition, the technique of phage display has been used to identify peptides that interact with estrogen receptors in the presence of different ligands [Paige, et al., Proceedings of the National Academy of Sciences of the United States of America 96: 3999-4004 (1999). For example, a peptide was identified that distinguished between ERα bound to the full estrogen receptor agonists 17β-estradiol and diethylstilbesterol. A different peptide was shown to distinguish between clomiphene bound to ERα and ERβ. These data indicate that each ligand potentially places the receptor in a unique and unpredictable conformation that is likely to have distinct biological activities.

As mentioned above, estrogens affect a panoply of biological processes. In addition, where gender differences have been described (e.g. disease frequencies, responses to challenge, etc), it is possible that the explanation involves the difference in estrogen levels between males and females.

SUMMARY OF THE INVENTION

This invention provides phenyl quinoline compounds that find use as estrogenic agents. In certain embodiments, such compounds are of formula I:

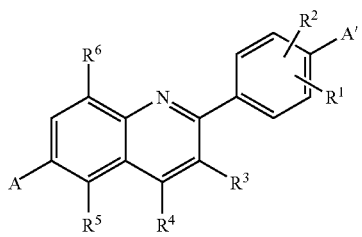

I wherein:
A and A' are each, independently, OH or OP;
P is alkyl, alkenyl, benzyl, acyl, aroyl, alkoxycarbonyl, sulfonyl or phosphoryl;
$R^1$ and $R^2$ are each, independently, H, halogen, $C_1$-$C_6$ alkyl, $C_2$-$C_7$ alkenyl, or $C_1$-$C_6$ alkoxy;
$R^3$ is H, halogen, or $C_1$-$C_6$ alkyl;
$R^4$ is H, halogen, $C_1$-$C_6$ alkyl, $C_2$-$C_7$ alkenyl, $C_2$-$C_7$ alkynyl, $C_3$-$C_7$ cycloalkyl, $C_1$-$C_6$ alkoxy, —CN, —CHO, acyl, or heteroaryl;
$R^5$ and $R^6$ are each, independently, H, halogen, $C_1$-$C_6$ alkyl, $C_2$-$C_7$ alkenyl, $C_2$-$C_7$ alkynyl, $C_3$-$C_7$ cycloalkyl, $C_1$-$C_6$ alkoxy, —CN, —CHO, acyl, phenyl, aryl or heteroaryl, provided that at least one of $R^4$, $R^5$ and $R^6$ is halogen, $C_1$-$C_6$ alkyl, $C_2$-$C_7$ alkenyl, $C_2$-$C_7$ alkynyl, $C_3$-$C_7$ cycloalkyl, $C_1$-$C_6$ alkoxy, —CN, —CHO, acyl, phenyl, aryl or heteroaryl;
wherein the alkyl or alkenyl moieties of $R^4$, $R^5$ or $R^6$ may be optionally substituted with halogen, OH, —CN, trifluroalkyl, trifluoroalkoxy, —$NO_2$, or phenyl;
wherein the alkynyl moiety of $R^4$, $R^5$ or $R^6$ may be optionally substituted with halogen, —CN, —CHO, acyl, trifluroalkyl, trialkylsilyl, or optionally substituted phenyl;
wherein the phenyl moiety of $R^5$ or $R^6$ may be optionally mono-, di-, or tri-subsitituted with halogen, $C_1$-$C_6$ alkyl, $C_2$-$C_7$ alkenyl, OH, $C_1$-$C_6$ alkoxy, —CN, —CHO, —$NO_2$, amino, $C_1$-$C_6$ alkylamino, di-($C_1$-$C_6$)alkylamino, thiol, or $C_1$-$C_6$ alkylthio;
provided that when each of $R^4$, $R^5$ and $R^6$ are H, $C_1$-$C_6$ alkyl, $C_2$-$C_7$ alkenyl, or $C_1$-$C_6$ alkoxy, then at least one of $R^1$ and $R^2$ is halogen, $C_1$-$C_6$ alkyl, $C_2$-$C_7$ alkenyl, or $C_1$-$C_6$ alkoxy;
provided that at least one of $R^4$ and $R^6$ is other than H;
or a N-oxide thereof or a pharmaceutically acceptable salt thereof or a prodrug thereof.

In another aspect, the invention is drawn to a pharmaceutical composition that comprises one or more of compound of the invention and a pharmaceutically acceptable carrier.

In yet other aspects, the invention is directed to use of the compounds of the invention in the treatment or prevention of diseases such as inflammatory bowel diseases, Crohn's disease, ulcerative proctitis, colitis, estrogen dependent cancers, hypercholesteremia, hyperlipidemia, cardiovascular disease, osteoporosis, atherosclerosis, senile dementias, Alzheimer's disease, anxiety disorders, neurodegenerative disorders, infertility, or arthritis.

DETAILED DESCRIPTION OF THE INVENTION

This invention relates to phenyl quinolines. In certain aspects, the invention relates to substituted 2-phenyl quinoline compounds. The invention also relates to use of phenyl quinoline compounds as estrogenic agents. The compounds of the invention are useful in the treatment and prevention of diseases that are associated with the estrogen receptor, particularly ERβ.

This invention provides estrogenic compounds of formula I:

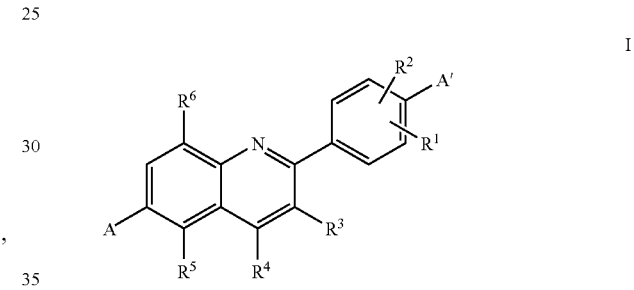

I wherein:
A and A' are each, independently, OH or OP;
P is alkyl, alkenyl, benzyl, acyl, aroyl, alkoxycarbonyl, sulfonyl or phosphoryl;
$R^1$ and $R^2$ are each, independently, H, halogen, $C_1$-$C_6$ alkyl, $C_2$-$C_7$ alkenyl, or $C_1$-$C_6$ alkoxy;
$R^3$ is H, halogen, or $C_1$-$C_6$ alkyl;
$R^4$, $R^5$ and $R^6$ are each, independently, H, halogen, $C_1$-$C_6$ alkyl, $C_2$-$C_7$ alkenyl, $C_2$-$C_7$ alkynyl, $C_3$-$C_7$ cycloalkyl, $C_1$-$C_6$ alkoxy, —CN, —CHO, acyl, phenyl, aryl or heteroaryl;
wherein the alkyl or alkenyl moieties of $R^3$, $R^4$, $R^5$ or $R^6$ may be optionally substituted with halogen, OH, —CN, trifluroalkyl, trifluoroalkoxy, —$NO_2$, or phenyl;
wherein the alkynyl moiety of $R^4$, $R^5$ or $R^6$ may be optionally substituted with halogen, —CN, —CHO, acyl, trifluroalkyl, trialkylsilyl, or optionally substituted phenyl;
wherein the phenyl moiety of $R^4$, $R^5$ or $R^6$ may be optionally mono-, di-, or tri-subsitituted with halogen, $C_1$-$C_6$ alkyl, $C_2$-$C_7$ alkenyl, OH, $C_1$-$C_6$ alkoxy, —CN, —CHO, —$NO_2$, amino, $C_1$-$C_6$ alkylamino, di-($C_1$-$C_6$)alkylamino, thiol, or $C_1$-$C_6$ alkylthio;

or a N-oxide thereof or a pharmaceutically acceptable salt thereof or a prodrug thereof.

In some embodiments, the invention concerns a compound of formula I wherein:
$R^4$ is H, halogen, $C_1$-$C_6$ alkyl, $C_2$-$C_7$ alkenyl, $C_2$-$C_7$ alkynyl, $C_3$-$C_7$ cycloalkyl, $C_1$-$C_6$ alkoxy, —CN, —CHO, acyl, or heteroaryl;

provided that when each of $R^4$, $R^5$ and $R^6$ are H, $C_1$-$C_6$ alkyl, $C_2$-$C_7$ alkenyl, or $C_1$-$C_6$ alkoxy, then at least one of $R^1$ and $R^2$ is halogen, $C_1$-$C_6$ alkyl, $C_2$-$C_7$ alkenyl, or $C_1$-$C_6$ alkoxy; and provided that at least one of $R^4$ and $R^6$ is other than H;

In some aspects, the invention relates to compounds of the formula I wherein:

$R^1$ and $R^2$ are each H; and $R^4$, $R^1$ and $R^6$ are each, independently, H, $C_1$-$C_6$ alkyl, $C_2$-$C_7$ alkenyl, or $C_1$-$C_6$ alkoxy, provided that at least one of $R^4$, $R^5$ and $R^6$ is $C_1$-$C_6$ alkyl, $C_2$-$C_7$ alkenyl, or $C_1$-$C_6$ alkoxy;

wherein the alkyl or alkenyl moieties of $R^4$, $R^5$ or $R^6$ may be optionally substituted with halogen, OH, —CN, trifluroalkyl, trifluoroalkoxy, —$NO_2$, or phenyl;

or a N-oxide thereof or a pharmaceutically acceptable salt thereof or a prodrug thereof.

In other aspects, the invention concerns compounds of the formula I wherein:

$R^3$ is H; and $R^4$ is H, aryl, or substituted aryl;

or a N-oxide thereof or a pharmaceutically acceptable salt thereof or a prodrug thereof.

In some compounds of formula I, it is preferred that at least one of A and A' is OH. Both A and A' are OH in some embodiments. In other embodiments, $R^1$, $R^2$ and $R^3$ are each, independently H or halogen. $R^1$ and $R^2$ are sometimes each halogen. In certain embodiments, $R^4$ and $R^6$ are each, independently H, halogen, $C_1$-$C_6$ alkyl, $C_2$-$C_7$ alkenyl, $C_2$-$C_7$ alkynyl, —CN, —CHO, acyl, or optionally substituted phenyl; and/or $R^5$ is H, halogen or —CN.

In some embodiments, A and A' are each OH, at least one of $R^1$ and $R^2$ are halogen, $R^5$ is H, and $R^4$ and $R^6$ are each independently halogen, $C_2$-$C_7$ alkynyl, or CN.

In some preferred embodiments of formula I, $R^5$ is H, halogen or CN. In other compounds, $R^4$ is H, halogen, $C_1$-$C_6$ alkyl, $C_2$-$C_7$ alkenyl, $C_2$-$C_7$ alkynyl, CN, CHO, or acyl; and $R^6$ is H, halogen, $C_1$-$C_6$ alkyl, $C_2$-$C_7$ alkenyl, $C_2$-$C_7$ alkynyl, CN, CHO, acyl or optionally substituted phenyl.

In certain embodiments of formula I, $R^4$ is halogen, $C_1$-$C_6$ alkyl, $C_2$-$C_7$ alkenyl, $C_2$-$C_7$ alkynyl or CN. In some compounds, $R^6$ is H, halogen, $C_1$-$C_6$ alkyl, $C_2$-$C_7$ alkenyl, $C_2$-$C_7$ alkynyl, CN or optionally substituted phenyl. In yet other embodiments, $R^4$ and $R^6$ are each, independently, halogen, $C_2$-$C_7$ alkynyl or CN. In some compounds, $R^4$ and $R^6$ are each independently halogen, $C_2$-$C_7$ alkynyl or CN; and $R^5$ is H.

When used herein the term "sulfonyl" refers to the group —S(=O)$_2$$R^{13}$ where $R^{13}$ is OH, alkyl, alkoxy or aryl and the term "phosphoryl" refers to the group —P(=O)($R^{14}$)$_2$ where $R^{14}$ is independently OH, alkyl, alkoxy or aryl.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable aids when a compound of this invention contains a basic moiety. Salts may also be formed from organic and inorganic bases, such as alkali metal salts (for example, sodium, lithium, or potassium) alkaline earth metal salts, ammonium salts, alkylammonium salts containing 1-6 carbon atoms or dialkylammonium salts containing 1-6 carbon atoms in each alkyl group, and trialkylammonium salts containing 1-6 carbon atoms in each alkyl group, when a compound of this invention contains an acidic moiety.

The instant invention also encompasses N-oxide derivatives of the compounds disclosed herein. These N-oxides can be prepared by methods known for preparing analogous compounds. For example, the compounds may be oxidized with a peracid, hydrogen peroxide, an alkali metal peroxide or an alkyl peroxide. One useful N-oxide derivative is a composition where the nitrogen atom of the quinoline ring forms the N-oxide group.

The instant invention also encompasses prodrug derivatives. "Prodrug derivative" means derivatives of the instant compounds that are converted in vivo to the corresponding non-derivatized form of the instant compounds.

The term "alkyl", as used herein, whether used alone or as part of another group, refers to a substituted or unsubstituted aliphatic hydrocarbon chain and includes, but is not limited to, straight and branched chains containing from 1 to 12 carbon atoms, preferably 1 to 6 carbon atoms, unless explicitly specified otherwise. For example, methyl, ethyl, propyl, isopropyl, butyl, i-butyl and t-butyl are encompassed by the term "alkyl." Specifically included within the definition of "alkyl" are those aliphatic hydrocarbon chains that are optionally substituted.

The carbon number as used in the definitions herein refers to carbon backbone and carbon branching, but does not include carbon atoms of the substituents, such as alkoxy substitutions and the like.

The term "alkenyl", as used herein, whether used alone or as part of another group, refers to a substituted or unsubstituted aliphatic hydrocarbon chain and includes, but is not limited to, straight and branched chains having 2 to 8 carbon atoms and containing at least one double bond. Preferably, the alkenyl moiety has 1 or 2 double bonds. Such alkenyl moieties may exist in the E or Z conformations and the compounds of this invention include both conformations. Specifically included within the definition of "alkenyl" are those aliphatic hydrocarbon chains that are optionally substituted. Heteroatoms, such as O, S or N—R, attached to an alkenyl should not be attached to a carbon atom that is bonded to a double bond.

The term acyl refers to alkylcarbonyl groups. The term benzyl includes substituted benzyl groups. The term aryl includes optionally substituted mono- and polycyclic aromatic ring systems, for example phenyl, naphthyl, etc. The term aroyl refers to optionally substituted arylcarbonyl groups such as benzoyl group. The term heteroaryl refers to optionally substituted heterocyclic aromatic ring systems containing up to 5 carbon atoms and at least one heteroatom selected from O, N, or S. Examples include furyl, thienyl, pyrrolyl, pyridyl, pyrimidinyl, oxazolyl, thiazolyl, etc.

An optionally substituted alkyl, alkenyl, aryl, heteroaryl, and phenyl may be substituted with one or more substituents which may be the same or different. Suitable substituents may be selected independently from nitro, cyano, —N($R_{11}$)($R_{12}$), halo, hydroxy, carboxy, alkyl, alkenyl, alkynyl, cycloalkyl, aryl, heteroaryl, alkoxy, aryloxy, heteroaryloxy, alkylalkoxy, alkoxycarbonyl, alkoxyalkoxy, perfluoroalkyl, perfluoroalkoxy, arylalkyl, alkylaryl, hydroxyalkyl, alkoxyalkyl, alkylthio, —S(O)$_2$—N($R_{11}$)($R_{12}$), —C(=O)—N($R_{11}$)($R_{12}$), ($R_{11}$)($R_{12}$)N-alkyl, ($R_{11}$)($R_{12}$)N-alkoxyalkyl, ($R_{11}$)($R_{12}$)N-alkylaryloxyalkyl, —S(O)$_s$-aryl (where s=0-2) or —S(O)$_s$-heteroaryl (where s=0-2). In certain embodiments of the invention, preferred substitutents for alkyl, alkenyl, alkynyl and cycloalkyl include nitro, cyano, —N($R_{11}$)($R_{12}$), halo, hydroxyl, aryl, heteroaryl, alkoxy, alkoxyalkyl, and alkoxycarbonyl. In certain embodiments of the invention, preferred substituents for aryl and heteroaryl include —N(R$_{11}$)(R$_{12}$), alkyl, halo, perfluoroalkyl, perfluoroalkoxy, arylalkyl and alkylaryl.

When alkyl or alkenyl moieties are substituted, for example, they may typically be mono-, di-, tri- or persubstituted. Examples for a halogen substituent include 1-bromo vinyl, 1-fluoro vinyl, 1,2-difluoro vinyl, 2,2-difluorovinyl, 1,2,2-trifluorovinyl, 1,2-dibromo ethane, 1,2 difluoro ethane, 1-fluoro-2-bromo ethane, CF$_2$CF$_3$, CF$_2$CF$_2$CF$_3$, and the like.

The term halogen includes bromine, chlorine, fluorine, and iodine.

The term "lower alkyl" refers to an alkyl group having 1 to 6 carbon atoms, in some embodiments 1 to 3 carbon atoms are preferred.

The term "lower alkoxy," as used herein, refers to the group R—O— where R is an alkyl group of 1 to 6 carbon atoms, in some embodiments 1 to 3 carbon atoms are preferred.

Unless otherwise specified all terms which may be substituted by one or more substituents may be substituted by one or more substituents which are the same or different.

As used in accordance with this invention, the term "providing," with respect to providing a compound or substance covered by this invention, means either directly administering such a compound or substance, or administering a prodrug, derivative, or analog which will form the effective amount of the compound or substance within the body.

The compounds of this invention can be prepared by methods known in the art of organic chemistry. The reagents used in the preparation of the compounds of this invention can be either commercially obtained or can be prepared by standard procedures described in the literature.

The syntheses of representative examples of this invention are described in the following Schemes 1-16.

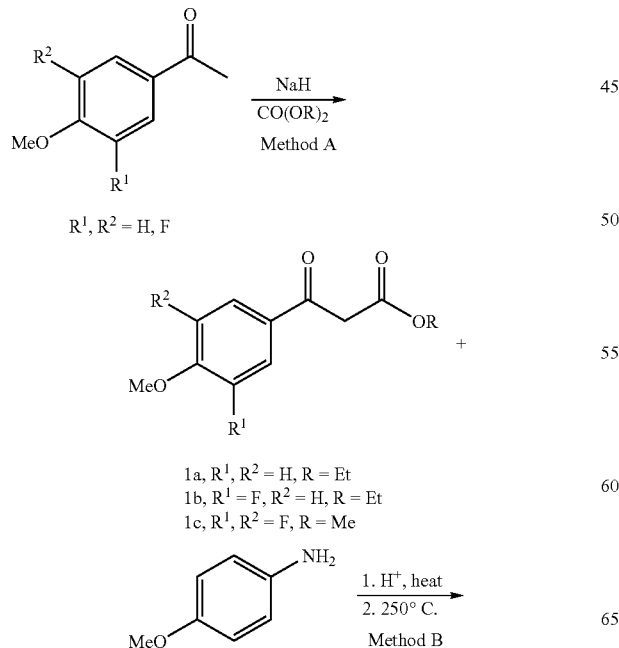

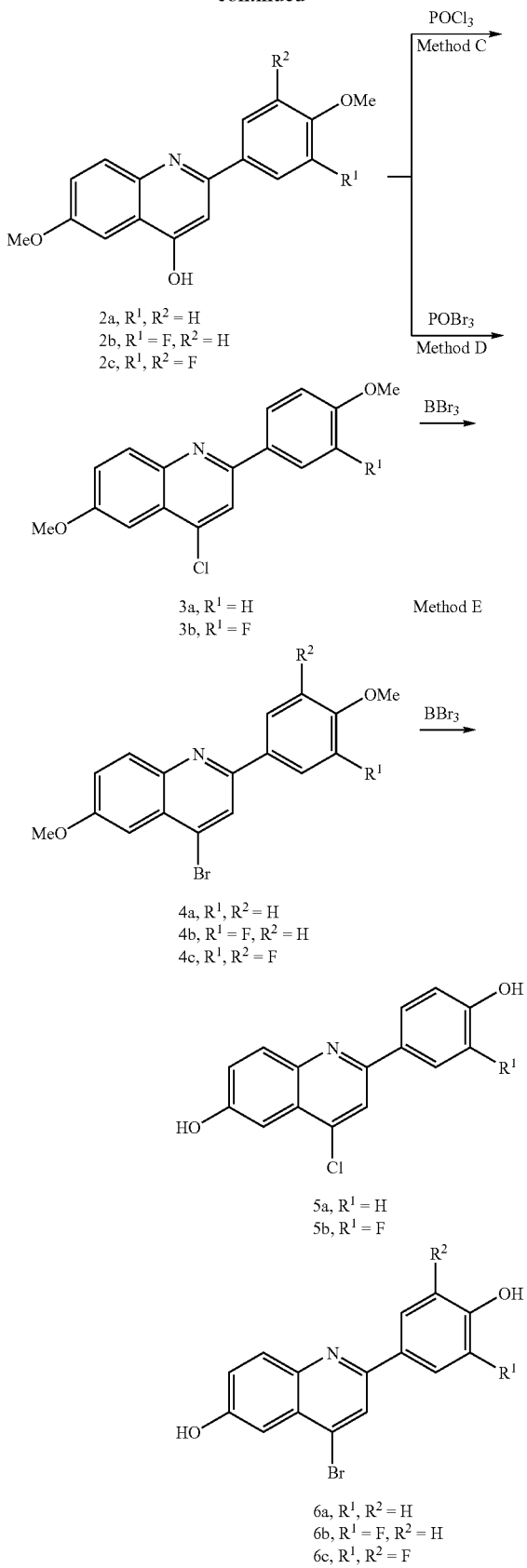

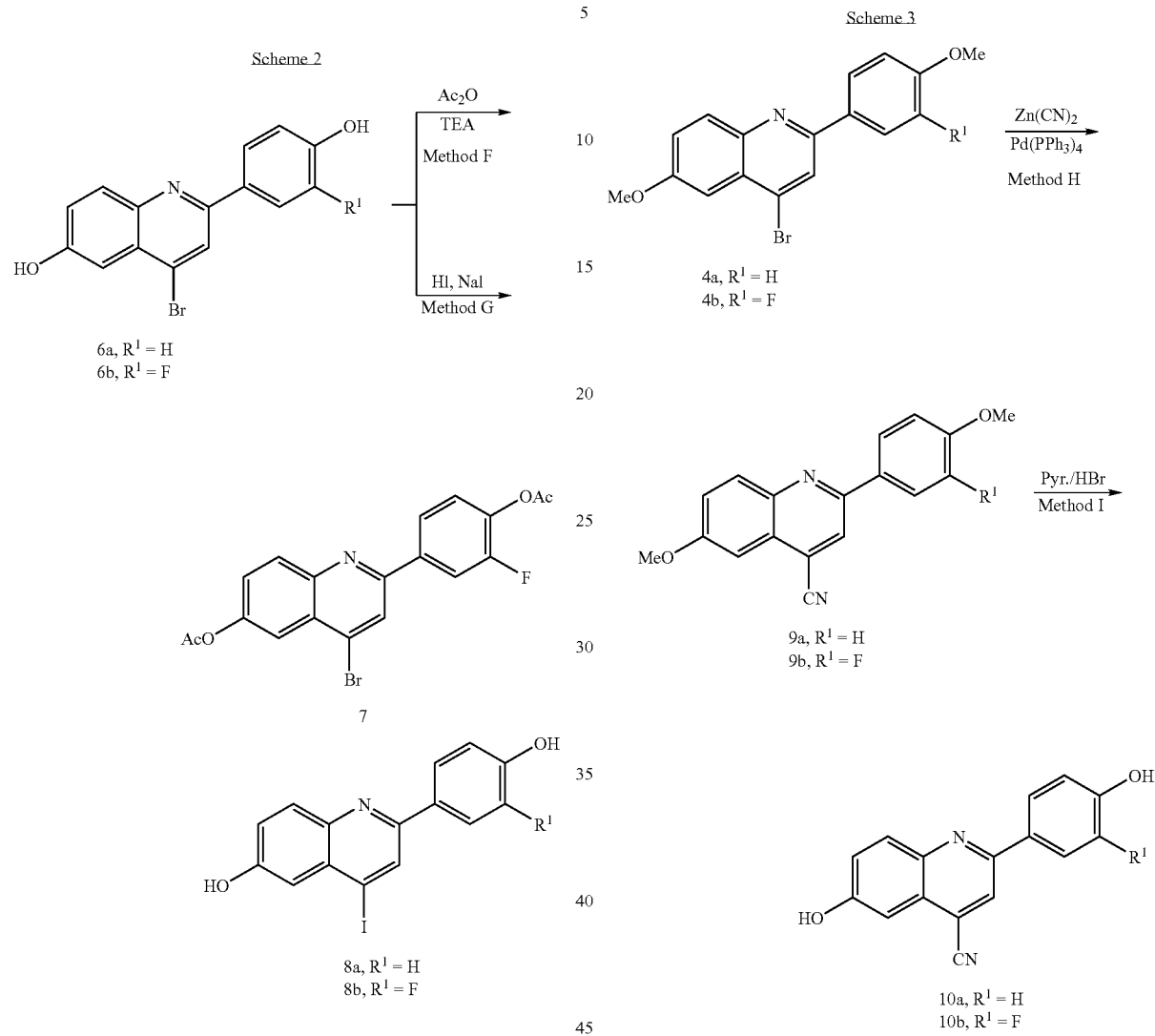

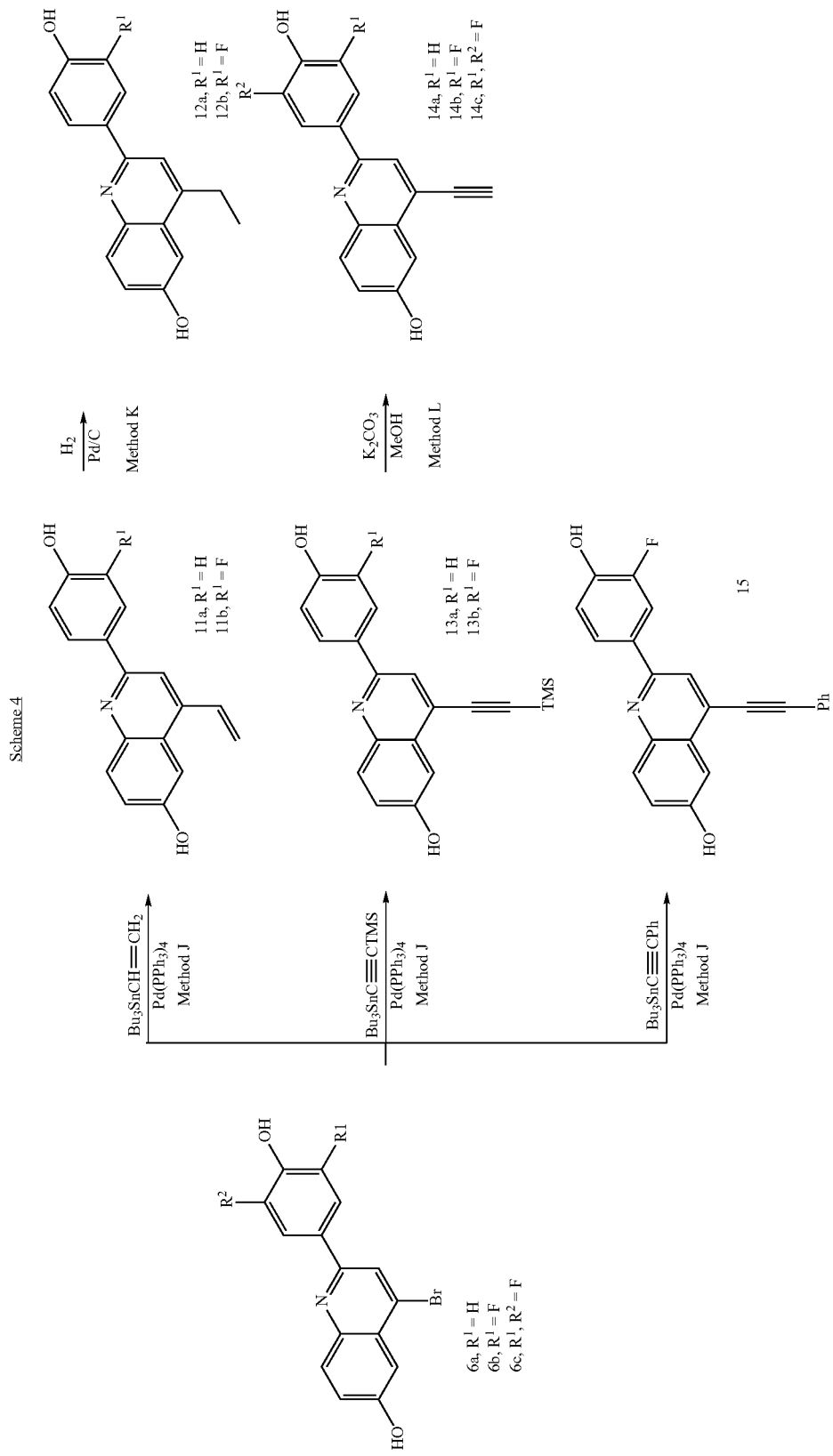

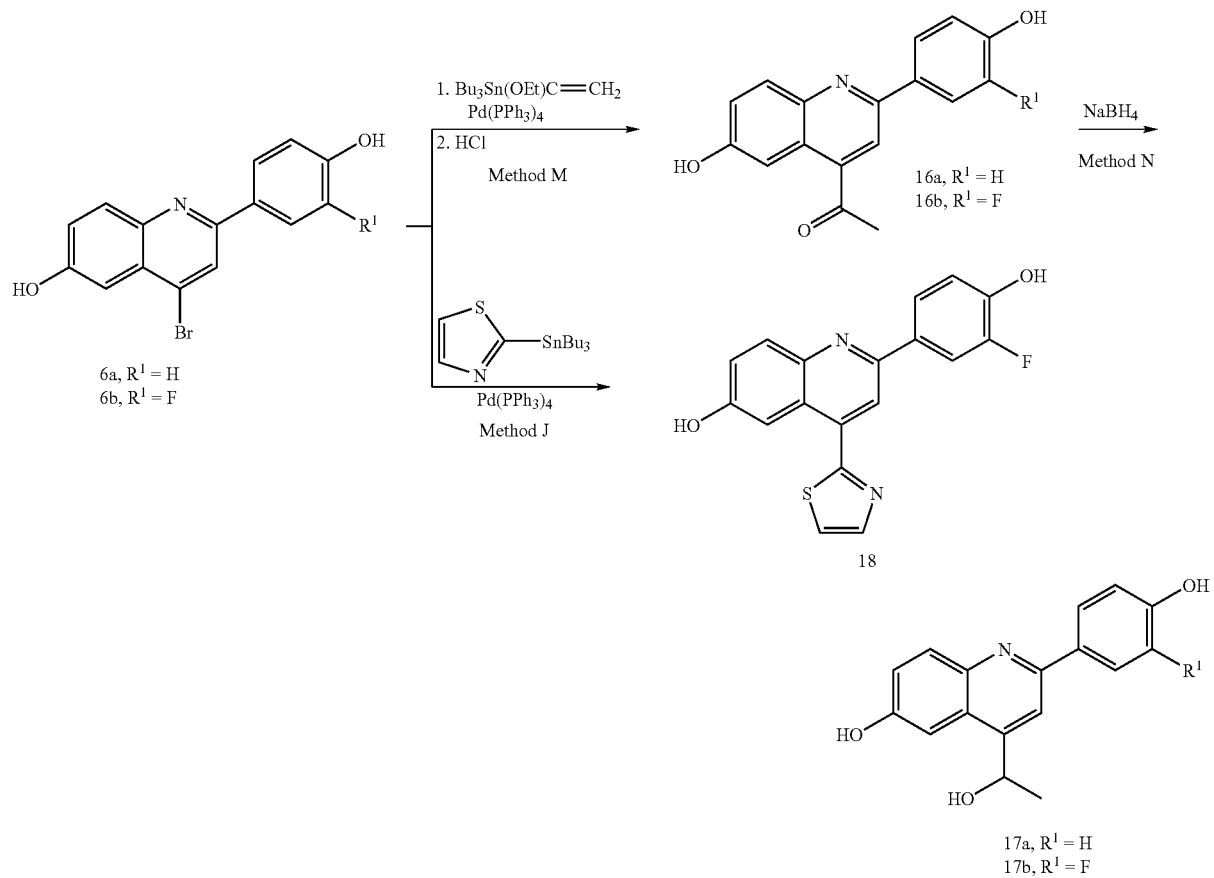
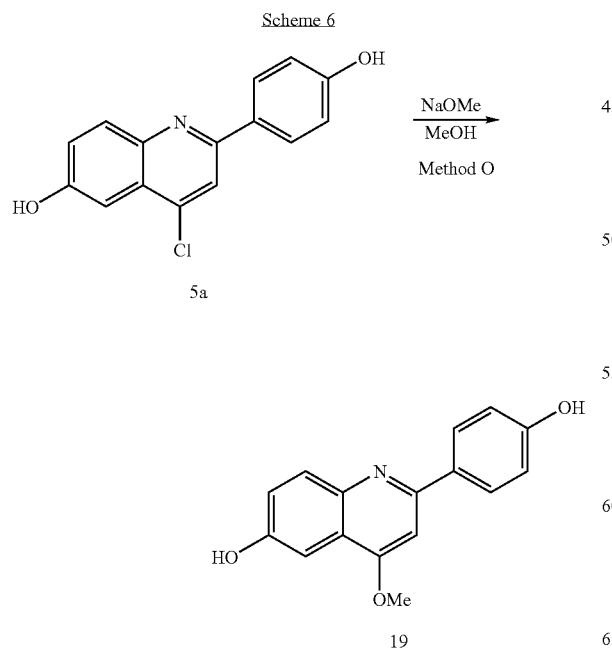
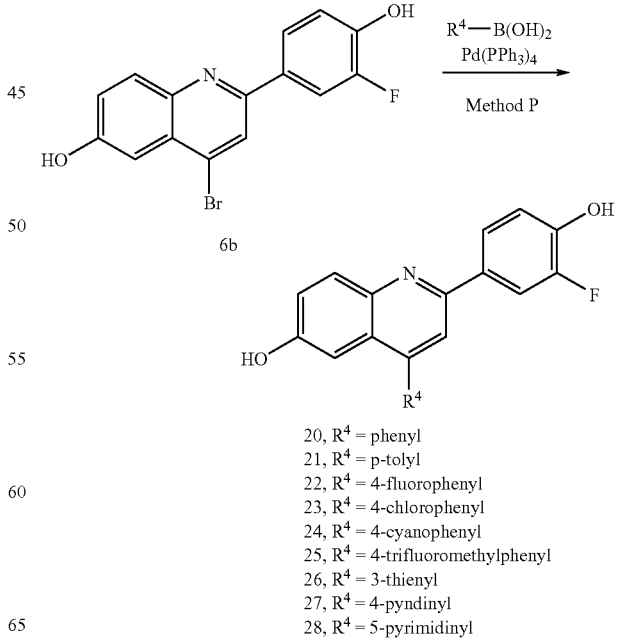

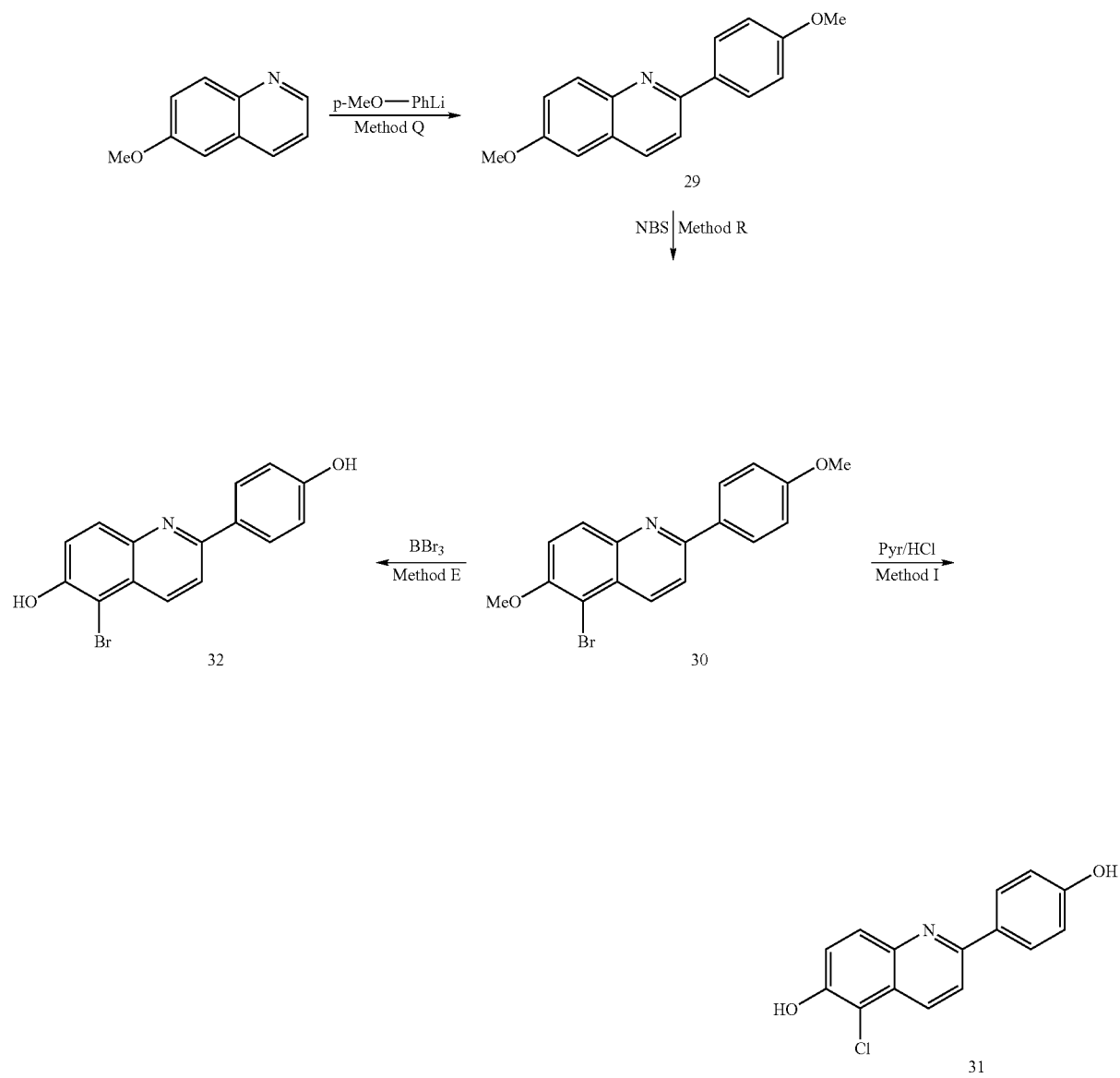

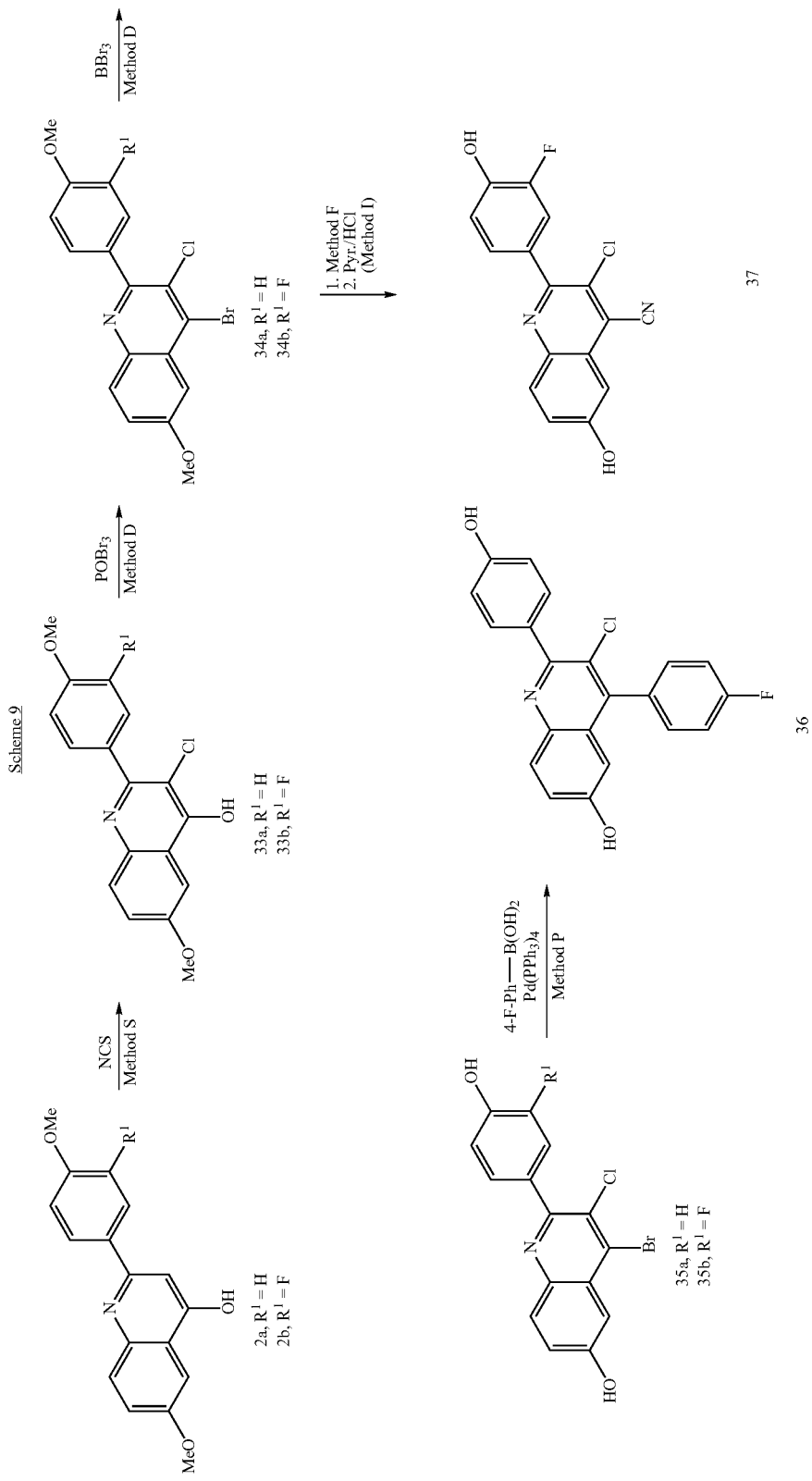

Scheme 10
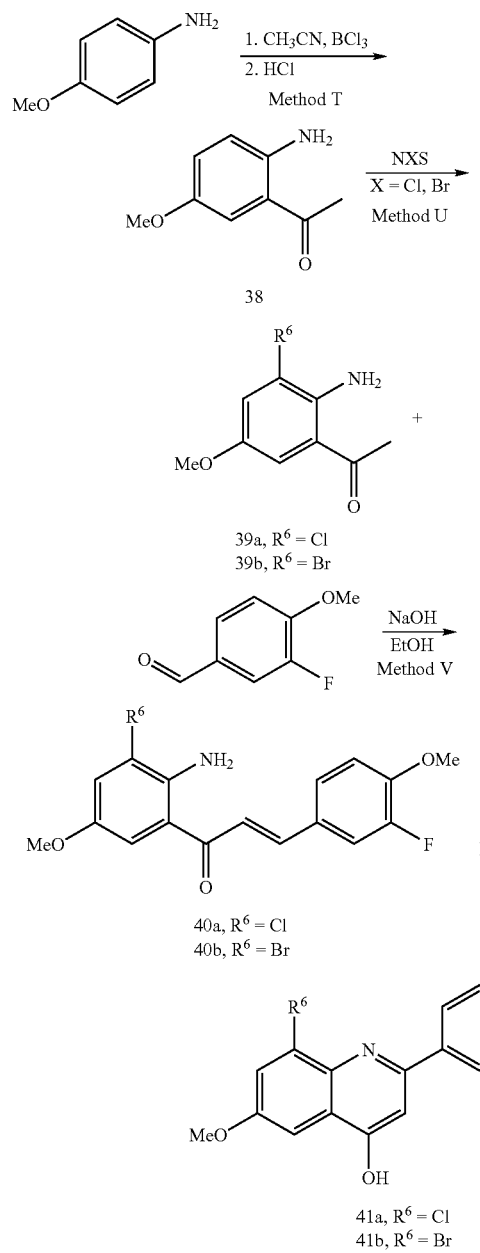
Scheme 11
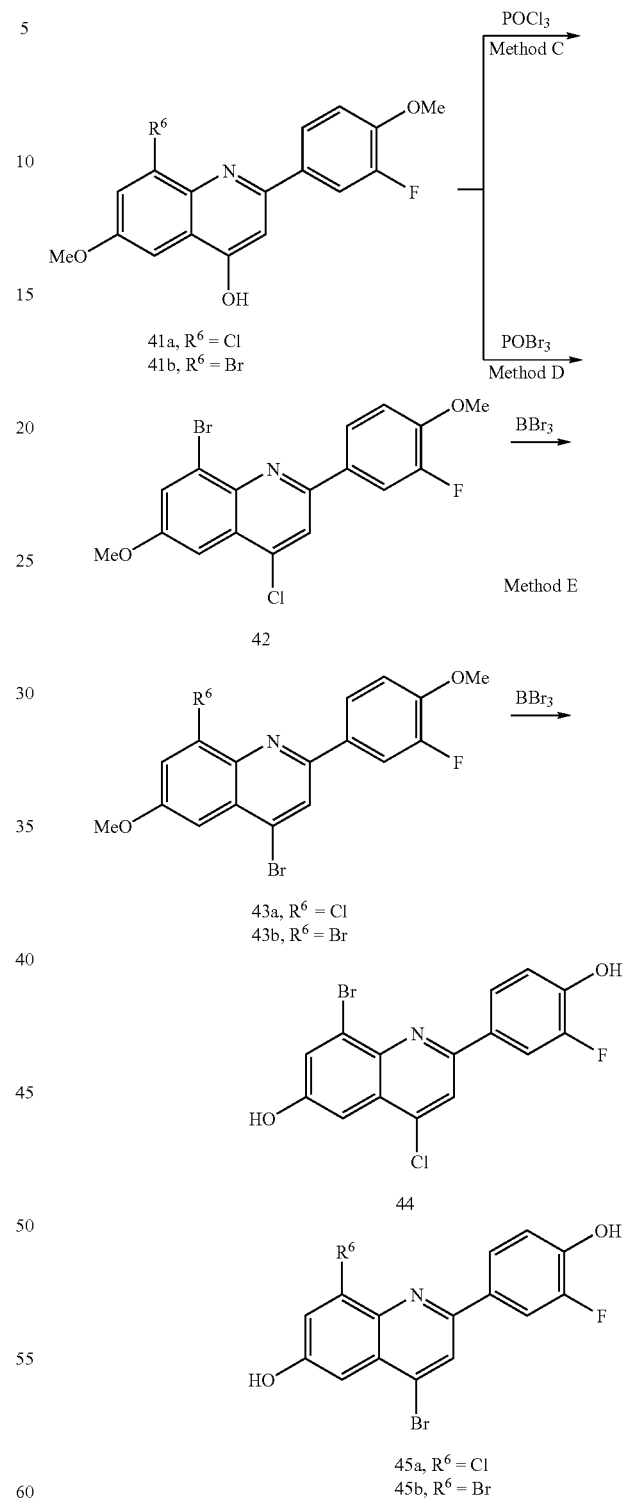

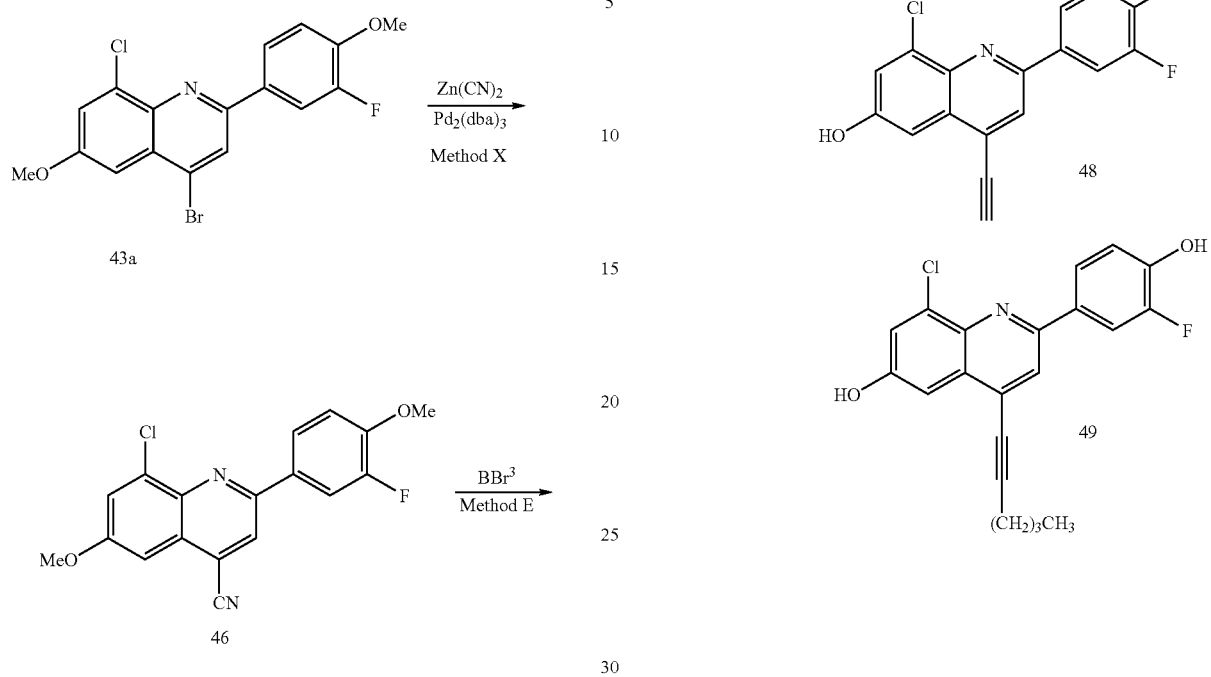
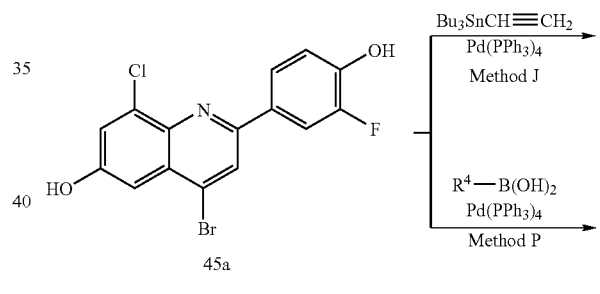
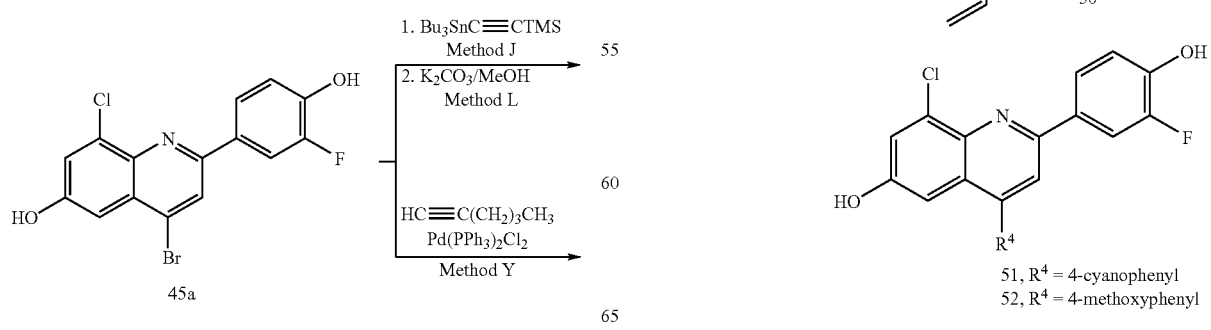

Scheme 15
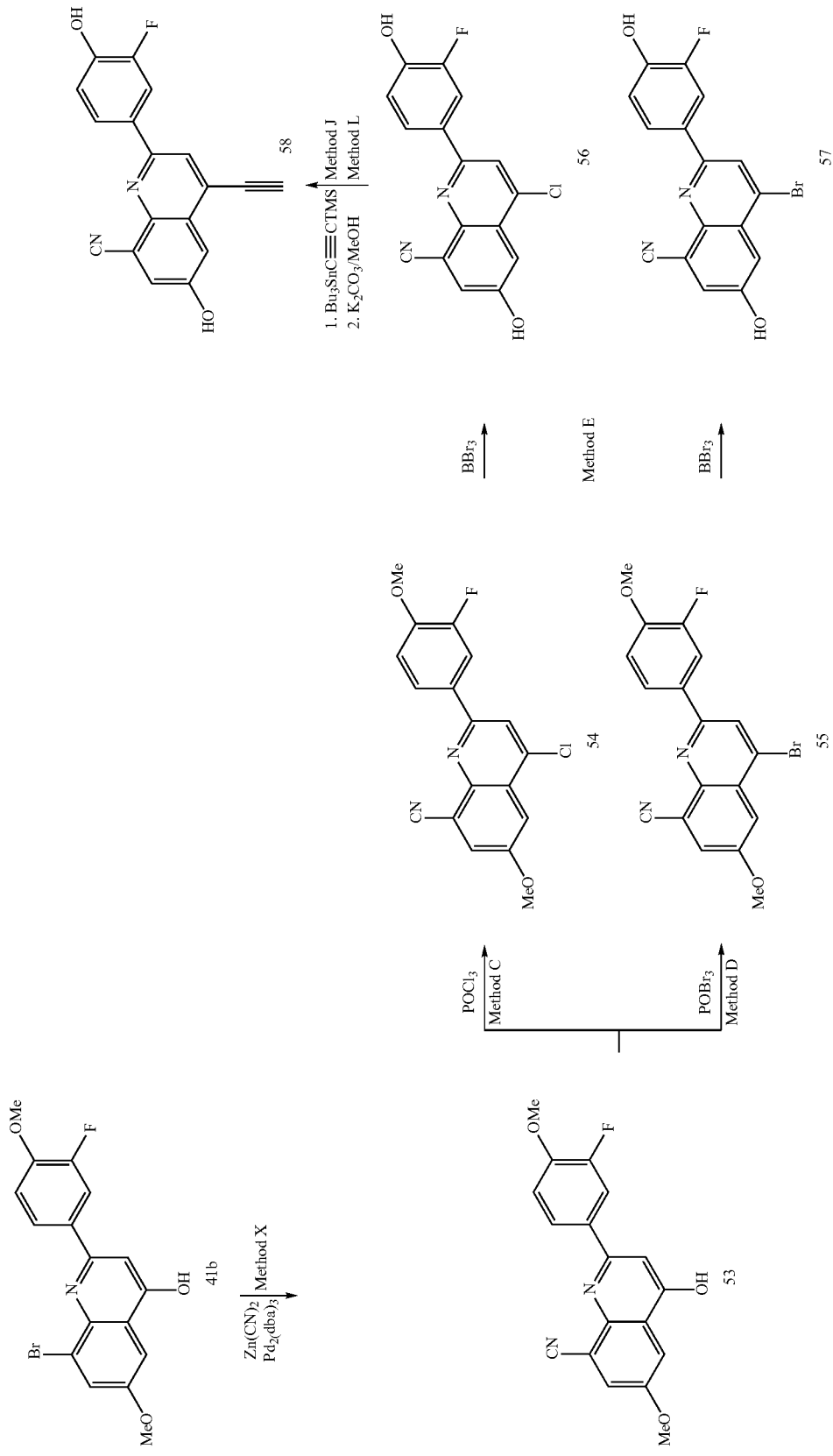

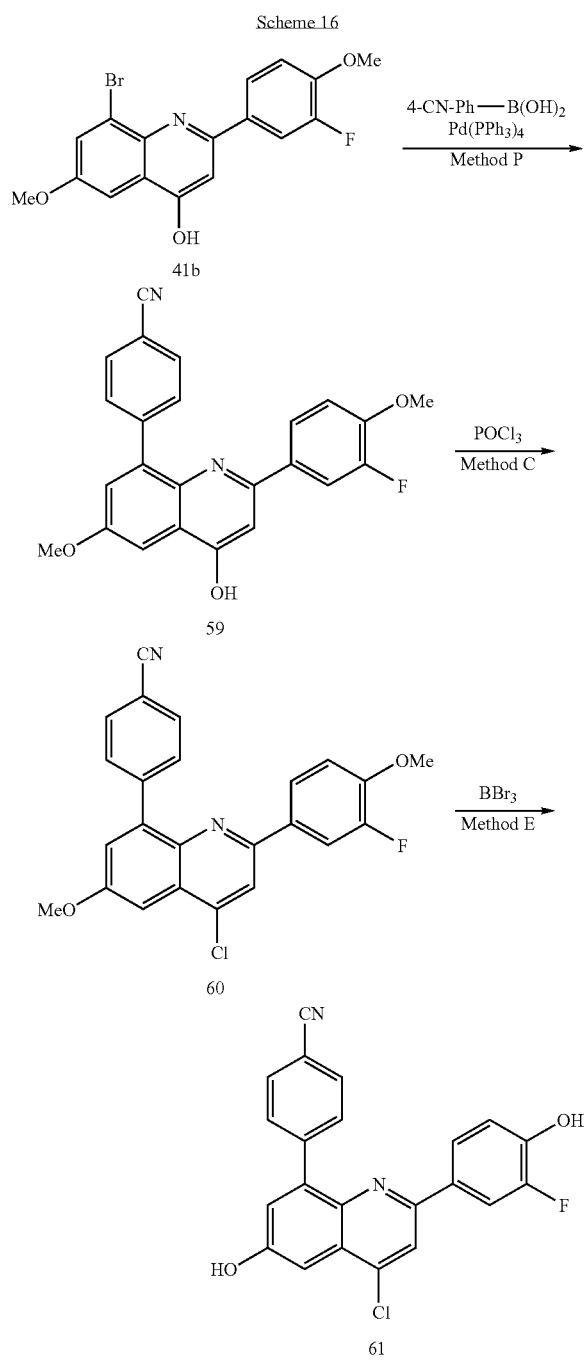

Scheme 16

Synthesis of Representative Compounds of the Invention

General Method—Aldrich Sure Seal™ Solvents, anhydrous without further purification, may be used for the reactions described herein and may be obtained from Aldrich Chemical Company. All reactions were carried out under a nitrogen atmosphere. Chromatography was performed using 230-400 mesh silica gel (Merck Grade 60, Aldrich Chemical Company). Thin layer chromatography was performed with Silica Gel 60 $F_{254}$ plates from EM Science. $^1$H and $^{19}$F NMR spectra were obtained on a Bruker AM-400 or Bruker DPX-300 instrument in deuterated solvents such as CDCl$_3$, DMSO-d6 or acetone-d6. Chemical shifts (δ) are given in parts per million (ppm) down field from tetramethylsilane (TMS). Melting points were determined on a Thomas-Hoover apparatus and are uncorrected. IR spectra were recorded on a Perkin-Elmer diffraction grating or Perkin-Elmer 784 spectrophotometers. Mass spectra were recorded on a Kratos MS 50 or Finnigan 8230 mass spectrometers. Compound nomenclature was generally arrived at by use of the Beilstein Autonomy™ program.

EXAMPLE 1

Method A: Preparation of substituted ethyl benzoylacetates 1. A typical procedure is described for the preparation of ethyl (3-fluoro-4-methoxybenzoyl)acetate (1b). To a refluxing suspension of NaH (60% dispersion in mineral oil, 42 g, 1.05 mol, 3 equiv., washed with hexane) and CO(OEt)$_2$ (85 mL, 0.70 mol, 2 equiv.) in 1,4-dioxane (300 mL), was added dropwise via an addition funnel a solution of 3-fluoro-4-methoxyacetophenone (58.9 g, 0.350 mol) in 1,4-dioxane (150 mL) under nitrogen. After the addition was complete, the mixture was stirred under reflux for an addition 30 min. After cooling to room temperature (rt), the reaction mixture was acidified by slow addition of glacial acetic acid and solvent was removed under reduced pressure. Water was then added and the mixture was extracted with EtOAc. The organic layer was washed with water, aq. NaHCO$_3$, brine, dried (Na$_2$SO$_4$), filtered and concentrated to give pure crude product as a yellow oil, which can be used directly in subsequent reactions. Yield: 78.90 g (94%).

EXAMPLE 1a

Ethyl(4-methoxybenzoyl)acetate (1a)

This compound was prepared from 4-methoxyacetophenone according to method A. Yellow oil; Yield: 95%; $^1$H-NMR (300 MHz, CDCl$_3$): δ 1.26 (t, J=7.3 Hz, 3H), 3.88 (s, 3H), 3.94 (s, 2H), 4.21 (q, J=7.3 Hz, 2H), 6.95 (m, 2H), 7.93 (m, 2H). Minor tautomer: 1.33 (t, J=7.3 Hz, 3H), 3.86 (s, 3H), 4.27 (q, J=7.3 Hz, 2H), 5.57 (s, 1H), 6.92 (m, 2H), 7.74 (m, 2H), 12.65 (s, 1H); MS (ESI) m/z 223 ([M+H]$^+$); Anal. Calcd for C$_{12}$H$_{14}$O$_4$: C, 64.85; H, 6.35. Found: C, 64.92; H, 6.11.

EXAMPLE 1b

Ethyl(3-fluoro-4-methoxybenzoyl)acetate (1b)

This compound was prepared according to method A. Yellow oil; Yield: 94%; $^1$H-NMR (300 MHz, CDCl$_3$) δ 1.26 (t, J=7.1 Hz, 3H), 3.93 (s, 2H), 3.97 (s, 3H), 4.21 (q, J=7.1 Hz, 2H), 7.01 (dd, J=8.4, 8.5 Hz, 1H), 7.72 (m, 2H). Minor tautomer: 1.33 (t, J=7.1 Hz, 3H), 3.94 (s, 3H), 4.28 (q, J=7.1 Hz, 2H), 5.57 (s, 1H), 6.99 (t, J=8.4 Hz, 1H), 7.54 (m, 2H), 12.62 (s, 1H); MS (ESI) m/z 241 ([M+H]$^+$); Anal. Calcd for C$_{12}$H$_{13}$FO$_4$: C, 60.00; H, 5.45. Found: C, 60.12; H, 5.25.

EXAMPLE 1c

Methyl(3,5-difluoro-4-methoxybenzoyl)acetate (1c)

This compound was prepared from 3,5-difluoro-4-methoxyacetophenone and dimethyl carbonate according to method A. Yellow solid; Yield: 97%; mp 64-67° C.; $^1$H-NMR (300 MHz, CDCl$_3$) δ 3.77 (s, 3H), 3.93 (s, 2H), 4.13 (t, J=1.7

Hz, 3H), 7.52 (m, 2H). Minor tautomer: 3.81 (s, 3H), 4.06 (m, 3H), 5.58 (s, 1H), 7.34 (m, 2H), 12.47 (s, 1H); MS (FSI) m/z 243 ([M−H]$^-$), 245 ([M+H]$^+$); Anal. Calcd for $C_{11}H_{10}F_2O_4$: C, 54.10; H, 4.13. Found: C, 54.37; H, 4.08.

EXAMPLE 2

Method B: Preparation of substituted 2-phenylquinolin-4-ols 2. A typical procedure is described for the preparation of 6-methoxy-2-(4-methoxyphenyl)quinolin-4-ol (2a). A mixture of ethyl(4-methoxybenzoyl)acetate (1a) (5.12 g, 23.0 mmol), p-anisidine (2.84 g, 23.0 mmol) and p-TsOH (22 mg, 0.116 mmol, 0.5 mol %) in toluene (100 mL) was heated at 80° C. for 16 h. After cooling, solvent was removed under reduced pressure. The resulting crude solid was dissolved in $Ph_2O$ (50 mL) and heated under reflux for 3 h. Upon cooling to rt, hexane (150 mL) was added to the mixture. The precipitate formed was collected by filtration, washed with $Et_2O$ and $CHCl_3$, and dried in vacuo. Yield: 4.49 g (69%).

EXAMPLE 2a

6-Methoxy-2-(4-methoxyphenyl)quinolin-4-ol (2a)

This compound was prepared according to method B. White solid; Yield: 69%; mp>260° C.; $^1$H-NMR (300 MHz, DMSO-d6) δ 3.85 (s, 6H), 6.29 (s, 1H), 7.14 (d, J=8.7 Hz, 2H), 7.31 (dd, J=9.0, 2.9 Hz, 1H), 7.50 (d, J=2.7 Hz, 1H), 7.73 (d, J=9.0 Hz, 1H), 7.80 (d, J=8.5 Hz, 2H), 11.59 (s, 1H); MS (ESI) m/z 280 ([M−H]$^-$), 282 ([M+H]$^+$); Anal. Calcd for $C_{17}H_{15}NO_3$: C, 72.58; H, 5.37; N, 4.98. Found: C, 72.11; H, 5.31; N, 4.84.

EXAMPLE 2b 2-(3-Fluoro-4-methoxyphenyl)-6-methoxyquinolin-4-ol (2b)

This compound was prepared from 1b according to method B. White solid; Yield: 49%; mp 326-328° C.; $^1$H-NMR (300 MHz, DMSO-d6) δ 3.85 (s, 3H), 3.93 (s, 3H), 6.37 (s, 1H), 7.33 (m, 2H), 7.50 (d, J=2.9 Hz, 1H), 7.69 (d, J=8.5 Hz, 1H), 7.72 (d, J=9.0 Hz, 1H), 7.78 (dd, J=12.6, 1.8 Hz, 1H), 11.60 (s, 1H); MS (ESI) m/z 298 ([M−H]$^-$), 300 ([M+H]$^+$); Anal. Calcd for $C_{17}H_{14}FNO_3$: C, 68.22; H, 4.71; N, 4.68. Found: C, 67.75; H, 4.78; N, 4.51.

EXAMPLE 2c 2-(3,5-Difluoro-4-methoxyphenyl)-6-methoxyquinolin-4-ol (2c)

This compound was prepared from 1c according to method B. White solid; Yield: 53%; $^1$H-NMR (300 MHz, DMSO-d6) δ 3.86 (s, 3H), 4.03 (s, 3H), 6.42 (br s, 1H), 7.35 (dd, J=9.0, 2.9 Hz, 1H), 7.48 (d, J=2.8 Hz, 1H), 7.73 (m, 3H), 11.65 (br s, 1H); MS (ESI) m/z 316 ([M−H]$^-$), 318 ([M+H]$^+$).

EXAMPLE 3

Method C: Preparation of substituted 4-chloro-2-phenylquinolines 3. A typical procedure is described for the preparation of 4-chloro-6-methoxy-2-(4-methoxyphenyl)quinoline (3a). A mixture of 6-methoxy-2-(4-methoxyphenyl)quinolin-4-ol (2a) (2.17 g, 7.70 mmol) and $POCl_3$ (5 mL) was heated at reflux for 1 h. After cooling, excess $POCl_3$ was removed under reduced pressure. Water and then aq. $K_2CO_3$ were slowly added to the solid residue and the mixture was extracted with EtOAc. The organic layer was washed with brine, dried ($Na_2SO_4$), filtered and concentrated to give a crude solid, which was passed through a short pad of silica gel and recrystallized ($CHCl_3$/hexane/−20° C.) to give pure product as a white solid. Yield: 2.12 g (92%).

EXAMPLE 3a

4-Chloro-6-methoxy-2-(4-methoxyphenyl)quinoline (3a)

This compound was prepared according to method C. White solid; Yield: 92%; mp 124-126° C.; $^1$H-NMR (300 MHz, $CDCl_3$) δ 3.88 (s, 3H), 3.98 (s, 3H), 7.02 (d, J=8.8 Hz, 2H), 7.40 (dd, J=8.8, 2.7 Hz, 1H), 7.42 (d, J=2.7 Hz, 1H), 7.88 (s, 1H), 8.03 (d, J=9.3 Hz, 1H), 8.06 (d, J=8.8 Hz, 2H); MS (ESI) m/z 300/302 ([M+H]$^+$); Anal. Calcd for $C_{17}H_{14}ClNO_2$: C, 68.12; H, 4.71; N, 4.67. Found: C, 68.05; H, 4.52; N, 4.50.

EXAMPLE 3b

4-Chloro-2-(3-fluoro-4-methoxyphenyl)-6-methoxyquinoline (3b)

This compound was prepared from 2b according to method C. White crystals; Yield: 89%; mp 112-116° C.; $^1$H-NMR (300 MHz, $CDCl_3$) δ 3.96 (s, 3H), 3.98 (s, 3H), 7.07 (dd, J=8.6, 8.6 Hz, 1H), 7.41 (m, 2H), 7.82 (dd, J=8.6, 1.2 Hz, 1H), 7.85 (s, 1H), 7.94 (dd, J=12.6, 2.0 Hz, 1H), 8.03 (d, J=8.6 Hz, 1H); MS (ESI) m/z 318/320 ([M+H]$^+$); Anal. Calcd for $C_{17}H_{13}ClFNO_2$: C, 64.26; H, 4.12; N, 4.41. Found: C, 64.03; H, 4.09; N, 4.37.

EXAMPLE 4

Method D: Preparation of substituted 4-bromo-2-phenylquinolines 4. A typical procedure is described for the preparation of 4-bromo-2-(3-fluoro-4-methoxyphenyl)-6-methoxy-quinoline (4b). A mixture of 2-(3-fluoro-4-methoxyphenyl)-6-methoxyquinolin-4-ol (2b) (10.48 g, 35.0 mmol) and $POBr_3$ (20 g, 70 mmol, 2 equiv.) in DMF (100 mL) was heated at 70° C. for 1 h. After cooling to rt, water and then aq. $K_2CO_3$ were slowly added, and the mixture was extracted with EtOAc. The organic layer was washed with water (2×), brine, dried ($Na_2SO_4$), filtered through a short pad of silica gel and concentrated to give a crude yellow solid, which was recrystallized ($CHCl_3$/hexane/−20° C.) to give pure product as a white solid. Yield: 12.00 g (95%).

EXAMPLE 4a

4-Bromo-6-methoxy-2-(4-methoxyphenyl)quinoline (4a)

This compound was prepared from 2a according to method D. White solid; Yield: 94%; mp 157-158° C.; $^1$H-NMR (500 MHz, $CDCl_3$) δ 3.88 (s, 3H), 3.99 (s, 3H), 7.03 (d, J=8.8 Hz, 2H), 7.38 (dd, J=8.8, 2.7 Hz, 1H), 7.40 (d, J=2.7 Hz, 1H), 8.02 (d, J=8.8 Hz, 1H), 8.07 (d, J=8.8 Hz, 2H), 8.09 (s, 1H); MS (ESI) m/z 344/346 ([M+H]$^+$); Anal. Calcd for $C_{17}H_{14}BrNO_2$: C, 59.32; H, 4.10; N, 4.07. Found: C, 59.37; H, 3.95; N, 4.03.

EXAMPLE 4b

4-Bromo-2-(3-fluoro-4-methoxyphenyl)-6-methoxyquinoline (4b)

This compound was prepared according to method D. White solid; Yield: 95%; mp 115-121° C.; $^1$H-NMR (300 MHz, DMSO-d6) δ 3.93 (s, 3H), 3.96 (s, 3H), 7.29 (dd, J=8.8, 8.5 Hz, 1H), 7.35 (d, J=2.6 Hz, 1H), 7.49 (dd, J=9.2, 2.7 Hz, 1H), 7.99 (d, J=9.2 Hz, 1H), 8.09 (m, 2H), 8.47 (s, 1H); MS (ESI) m/z 362/364 ([M+H]$^+$); Anal. Calcd for $C_{17}H_{13}BrFNO_2$: C, 56.37; H, 3.62; N, 3.87. Found: C, 56.44; H, 3.63; N, 3.80.

EXAMPLE 4c

4-Bromo-2-(3,5-difluoro-4-methoxyphenyl)-6-methoxyquinoline (4c)

This compound was prepared from 2c according to method D. White solid; Yield: 66%; mp 170-172° C.; $^1$H-NMR (400 MHz, CDCl$_3$) δ 4.00 (s, 3H), 4.08 (s, 3H), 7.41 (m, 2H), 7.71 (m, 2H), 8.01 (m, 2H). $^{19}$F-NMR (400 MHz, CDCl$_3$) δ −128.34 (d, J=9.0 Hz); MS (ESI) m/z 380/382 ([M+H]$^+$). Anal. Calcd for $C_{17}H_{12}BrF_2NO_2$: C, 53.71; H, 3.18; N, 3.68. Found: C, 53.47; H, 3.17; N, 3.60.

EXAMPLE 5

Method E: General Procedure for O-demethylation using BBr$_3$. A typical procedure is described for the synthesis of 4-bromo-2-(4-hydroxyphenyl)quinolin-6-ol (6a). To a solution of 4-bromo-6-methoxy-2-(4-methoxyphenyl)quinoline (4a) (241 mg, 0.70 mmol) in 1,2-dichloroethane (5 mL) was added slowly a solution of BBr$_3$ (1.0 M, 2.8 mL, 2.8 mmol) in CH$_2$Cl$_2$. The reaction mixture was stirred at rt for 30 min and then at 40° C. for 2 h. After cooling in an ice bath, aq. NaHCO$_3$ was added very slowly with vigorous stirring to quench the reaction, and the resulting mixture was extracted with EtOAc. The organic layer was washed with brine, dried (Na$_2$SO$_4$), filtered through a short pad of silica gel, and concentrated to give a yellow solid, which was recrystallized (THF/hexane). Yield: 181 mg (82%). If necessary, the product can be further purified by silica gel chromatography or by extraction with 2N HCl followed by neutralization with NaHCO$_3$.

EXAMPLE 5a

4-Chloro-2-(4-hydroxyphenyl)quinolin-6-ol (5a)

This compound was prepared from 3a according to method E. Yellow solid; Yield: 77%; mp>260° C. (dec.); $^1$H-NMR (500 MHz, DMSO-d6) δ 6.90 (d, J=8.8 Hz, 2H), 7.37 (s, 1H), 7.38 (dd, J=8.8, 2.7 Hz, 1H), 7.94 (d, J=8.8 Hz, 1H), 8.09 (d, J=8.8 Hz, 2H), 8.16 (s, 1H), 9.83 (s, 1H), 10.33 (s, 1H); MS (ESI) m/z 270/272 ([M−H]$^−$), 272/274 ([M+H]$^+$); Anal. Calcd for $C_{15}H_{10}ClNO_2$: C, 66.31; H, 3.71; N, 5.16. Found: C, 66.15; H, 3.78; N, 5.04.

EXAMPLE 5b

4-Chloro-2-(3-fluoro-4-hydroxyphenyl)quinolin-6-ol (5b)

This compound was prepared from 3b according to method E. Yellow powder; Yield: 70%; mp>320° C. (dec.); $^1$H-NMR (300 MHz, DMSO-d6) δ 7.08 (dd, J=8.9, 8.7 Hz, 1H), 7.37 (s, 1H), 7.40 (dd, J=9.0, 2.5 Hz, 1H), 7.95 (m, 2H), 8.06 (dd, J=13.0, 1.8 Hz, 1H), 8.24 (s, 1H), 10.32 (s, 1H), 10.42 (s, 1H); MS (ESI) m/z 288/290 ([M−H]$^−$), 290/292 ([M+H]$^+$); Anal. Calcd for $C_{15}H_9ClFNO_2$: C, 62.19; H, 3.13; N, 4.83. Found: C, 61.95; H, 3.30; N, 4.64.

EXAMPLE 6a

4-Bromo-2-(4-hydroxyphenyl)quinolin-6-ol (6a)

This compound was prepared according to method E. Yellow powder; Yield: 82%; mp>260° C. (dec.); $^1$H-NMR (300 MHz, DMSO-d6) δ 6.89 (d, J=8.7 Hz, 2H), 7.35 (s, 1H), 7.36 (dd, J=9.5, 2.6 Hz, 1H), 7.92 (d, J=9.5 Hz, 1H), 8.09 (d, J=8.7 Hz, 2H), 8.32 (s, 1H), 9.85 (s, 1H), 10.34 (s, 1H); MS (ESI) m/z 314/316 ([M−H]$^−$), 316/318 ([M+H]$^+$); Anal. Calcd for $C_{15}H_{10}BrNO_2$: C, 56.99; H, 3.19; N, 4.43. Found: C, 55.05; H, 3.61; N, 4.13.

EXAMPLE 6b

4-Bromo-2-(3-fluoro-4-hydroxyphenyl)quinolin-6-ol (6b)

This compound was prepared from 4b according to method E. Yellow powder; Yield: 73%; mp>230° C. (dec.); $^1$H-NMR (300 MHz, DMSO-d6) δ 7.07 (dd, J=8.9, 8.6 Hz, 1H), 7.36 (s, 1H), 7.39 (dd, J=9.0, 2.6 Hz, 1H), 7.94 (d, J=8.8 Hz, 2H), 8.06 (dd, J=13.0, 2.0 Hz, 1H), 8.39 (s, 1H), 10.32 (s, 1H), 10.42 (s, 1H); MS (ESI) m/z 332/334 ([M−H]$^−$), 334/336 ([M+H]$^+$); Anal. Calcd for $C_{15}H_9BrFNO_2$: C, 53.92; H, 2.71; N, 4.19. Found: C, 53.84; H, 2.72; N, 4.01.

EXAMPLE 6c

4-Bromo-2-(3,5-difluoro-4-hydroxyphenyl)quinolin-6-ol (6c)

This compound was prepared from 4c according to method E. Yellow powder; Yield: 66%; mp>255° C. (dec.); $^1$H-NMR (300 MHz, DMSO-d6) δ 7.37 (d, J=2.6 Hz, 1H), 7.40 (dd, J=9.0, 2.6 Hz, 1H), 7.95 (d, J=8.9 Hz, 1H), 7.99 (d, J=10.1 Hz, 2H), 8.47 (s, 1H), 10.48 (s, 1H), 10.67 (s, 1H). $^{19}$F-NMR (400 MHz, DMSO-d6) δ −132.23 (d, J=9.5 Hz); MS (ESI) m/z 350/352 ([M−H]$^−$), 352/354 ([M+H]$^+$); Anal. Calcd for $C_{15}H_8BrF_2NO_2$: C, 51.16; H, 2.29; N, 3.98. Found: C, 50.80; H, 2.60; N, 3.75.

EXAMPLE 7

6-Acetoxy-4-bromo-2-(3-fluoro-4-acetoxyphenyl)quinoline (7)

Method F. To a solution of 4-bromo-2-(3-fluoro-4-hydroxyphenyl)quinolin-6-ol (6b) (668 mg 2.00 mmol) in THF (20 mL) was added Et$_3$N (3.5 mL). After 5 min, acetic anhydride (1.2 mL) was slowly added and the mixture was stirred at rt for 12 h. The reaction mixture was filtered through Celite, and the filtrate was concentrated. Water was added to the solid residue, and the mixture was extracted with EtOAc. The organic layer was washed with water, brine, dried (Na$_2$SO$_4$), filtered and concentrated to give an ivory solid, which was recrystallized (CHCl$_3$/hexane). Yield: 821 mg (98%); mp 208-209° C.; $^1$H-NMR (400 MHz, CDCl$_3$) δ 2.38 (s, 3H), 2.40 (s, 3H), 7.29 (dd, J=8.5, 7.6 Hz, 1H), 7.53 (dd, J=9.1, 2.5 Hz, 1H), 7.90 (m, 2H), 8.03 (dd, J=11.3, 2.1 Hz, 1H), 8.13 (s, 1H), 8.15 (d, J=9.0 Hz, 1H); Anal. Calcd for $C_{19}H_{13}BrFNO_4$: C, 54.57; H, 3.13; N, 3.35. Found: C, 55.10; H, 2.96; N, 3.07.

EXAMPLE 8

Method G. A typical procedure is described for the synthesis of 2-(3-fluoro-4-hydroxyphenyl)-4-iodoquinolin-6-ol (8b). A mixture of 4-bromo-2-(3-fluoro-4-hydroxyphenyl) quinolin-6-ol (6b) (100 mg, 0.30 mmol), NaI (225 mg, 1.50 mmol), and HI (57%, 0.01 mL, 0.08 mmol) in 2-butanone (1.5 mL) was refluxed until all starting material was consumed (24 h). After cooling to rt, the reaction mixture was concentrated, and partitioned between aq. $NaHCO_3$ and EtOAc. The organic layer was dried ($Na_2SO_4$), filtered through a pad of silica gel, and concentrated to give pure product as an orange powder. Further purification was obtained by recrystallization (THF/hexanes/−20° C.). Yield: 95 mg (quant.).

EXAMPLE 8a 2-(4-Hydroxyphenyl)-4-iodoquinolin-6-ol (8a)

This compound was prepared from 6a according to method G. Yellow solid; Yield: 87%; mp 198° C. (dec.); $^1$H-NMR (300 MHz, DMSO-d6): δ 6.89 (d, J=8.7 Hz, 2H), 7.26 (d, J=2.6 Hz, 1H), 7.32 (dd, J=9.0, 2.6 Hz, 1H), 7.84 (d, J=9.0 Hz, 1H), 8.06 (d, J=8.7 Hz, 2H), 8.51 (s, 1H), 9.83 (s, 1H), 10.30 (s, 1H); MS (ESI) m/z 362 ([M−H]$^-$), 364 ([M+H]$^+$); Anal. Calcd for $C_{15}H_{10}INO_2$: C, 49.61; H, 2.78; N, 3.86. Found: C, 47.52; H, 3.11; N, 3.54.

EXAMPLE 8b 2-(3-Fluoro-4-hydroxyphenyl)-4-iodoquinolin-6-ol (8b)

This compound was prepared according to method G. Orange powder; Yield: quant.; mp>180° C. (dec.); $^1$H—N (400 MHz, DMSO-d6) δ 7.06 (t, J=8.8 Hz, 1H), 7.26 (d, J=2.6 Hz, 1H), 7.33 (dd, J=9.0, 2.6 Hz, 1H), 7.86 (d, J=9.0 Hz, 1H), 7.89-7.92 (m, 1H), 8.03 (dd, J=13.0, 2.1 Hz, 1H), 8.56 (s, 1H), 10.26 (s, 1H), 10.33 (s, 1H); MS (ESI) m/z 380 ([M−H]$^-$), 382 ([M+H]$^+$); Anal. Calcd for $C_{15}H_9FINO_2$: C, 47.27; H, 2.38; N, 3.67. Found: C, 46.31; H, 2.83; N, 3.15.

EXAMPLE 9

Method H: Conversion of aryl bromides to aryl cyanides. A typical procedure is described for the synthesis of 4-cyano-6-methoxy-2-(4-methoxyphenyl)quinoline (9a). A mixture of 4-bromo-6-methoxy-2-(4-methoxyphenyl)quinoline (4a) (172 mg, 0.50 mmol), $Zn(CN)_2$ (59 mg, 0.50 mmol) and $Pd(PPh_3)_4$ (29 mg, 0.025 mmol, 5 mol %) in anhydrous DMF (2.5 mL) was heated at 80° C. under nitrogen until all starting material was consumed (2-3 h). After cooling to rt, water and $NH_4OH$ (2N, 5 mL) were added and the mixture was extracted with EtOAc. The organic layer was washed with water, brine, dried ($Na_2SO_4$), filtered and concentrated to give a crude solid, which was recrystallized (acetone/−20° C.) to give pure product as a white solid. Yield: 127 mg (88%).

EXAMPLE 9a

4-Cyano-6-methoxy-2-(4-methoxyphenyl)quinoline (9a)

This compound was prepared according to method H. White solid; Yield: 88%; mp 183-184° C.; $^1$H-NMR (300 MHz, DMSO-d6) δ 3.86 (s, 3H), 4.00 (s, 3H), 7.12 (d, J=8.8 Hz, 2H), 7.32 (d, J=2.7 Hz, 1H), 7.58 (dd, J=9.2, 2.7 Hz, 1H), 8.09 (d, J=9.2 Hz, 1H), 8.27 (d, J=8.8 Hz, 2H), 8.71 (s, 1H); MS (ESI) m/z 291 ([M+H]$^+$); Anal. Calcd for $C_{18}H_{14}N_2O_2$: C, 74.47; H, 4.86; N, 9.65. Found: C, 73.39; H, 4.60; N, 9.49.

EXAMPLE 9b

4-Cyano-2-(3-fluoro-4-methoxyphenyl)-6-methoxyquinoline (9b)

This compound was prepared from 4b according to method H. White solid; Yield: 92%; mp 189-190° C.; $^1$H-NMR (300 MHz, CDCl$_3$) δ 3.98 (s, 3H), 4.02 (s, 3H), 7.10 (dd, J=8.6, 8.5 Hz, 1H), 7.36 (d, J=2.7 Hz, 1H), 7.48 (dd, J=9.2, 2.7 Hz, 1H), 7.84 (m, 1H), 7.98 (dd, J=12.5, 2.2 Hz, 1H), 8.08 (s, 1H), 8.09 (d, J=9.2 Hz, 1H); MS (ESI) m/z 309 ([M+H]$^+$); Anal. Calcd for $C_{18}H_{13}FN_2O_2$: C, 70.12; H, 4.25; N, 9.09. Found: C, 70.75; H, 4.64; N, 7.69.

EXAMPLE 10

Method I: General Procedure for O-demethylation using Pyr./HBr (or Pyr./HCl). A typical procedure is described for the synthesis of 4-cyano-2-(3-fluoro-4-hydroxyphenyl)quinolin-6-ol (10b). A mixture of 4-cyano-2-(3-fluoro-4-methoxyphenyl)-6-methoxyquinoline (9b) (93 mg, 0.30 mmol) and pyr./HBr (480 mg, 3.00 mmol) was heated at 200° C. in a sealed reaction vessel on a sand bath until all starting material was consumed (10-30 min for Pyr./HBr, 4-7 h for Pyr./HCl). After cooling to rt, water was added to dissolve the solid and the mixture was extracted with EtOAc. The organic layer was washed with water, brine, dried ($Na_2SO_4$), filtered through a pad of silica gel and concentrated to give a crude solid, which was recrystallized (THF/ether/−20° C.) to give pure product as a yellow powder. Yield: 80 mg (95%).

EXAMPLE 10a

4-Cyano-2-(4-hydroxyphenyl)quinolin-6-ol (10a)

This compound was prepared from 9a using Pyr./HBr according to method I. Yellow solid; Yield: 89%; mp>240° C. (dec.); $^1$H-NMR (300 MHz, DMSO-d6) δ 6.92 (d, J=8.7 Hz, 2H), 7.30 (d, J=2.6 Hz, 1H), 7.45 (dd, J=9.1, 2.6 Hz, 1H), 8.02 (d, J=9.1 Hz, 1H), 8.13 (d, J=8.7 Hz, 2H), 8.58 (s, 1H), 9.93 (s, 1H), 10.64 (s, 1H): MS (ESI) m/z 261 ([M−H]$^-$), 263 ([M+H]$^+$); Anal. Calcd for $C_{16}H_{10}N_2O_2$: C, 73.27; H, 3.84; N, 10.68. Found: C, 71.75; H, 3.86; N, 10.14.

EXAMPLE 10b

4-Cyano-2-(3-fluoro-4-hydroxyphenyl)quinolin-6-ol (10b)

This compound was prepared using Pyr./HBr according to method I. Yellow powder; Yield: 95%; mp>280° C. (dec.); $^1$H-NMR (400 MHz, DMSO-d6) δ 7.10 (dd, J=9.0, 8.8 Hz, 1H), 7.31 (d, J=2.7 Hz, 1H), 7.47 (dd, J=9.0, 2.7 Hz, 1H), 7.97 (m, 1H), 8.04 (d, J=9.0 Hz, 1H), 8.08 (dd, J=12.8, 2.1 Hz, 1H), 8.62 (s, 1H), 10.36 (s, 1H), 10.68 (s, 1H); MS (ESI) m/z 279 ([M−H]$^-$), 281 ([M+H]$^+$); Anal. Calcd for $C_{16}H_9FN_2O_2$: C, 68.57; H, 3.24; N, 10.00. Found: C, 67.26; H, 3.30; N, 9.58.

EXAMPLE 11

Method J: General procedure for Pd-catalyzed coupling reactions of 4-bromoquinolines with tin reagents. A typical procedure is described for the synthesis of 2-(3-fluoro-4-hydroxyphenyl)-4-vinylquinolin-6-ol (11b). A mixture of 4-bromo-2-(3-fluoro-4-hydroxyphenyl)quinolin-6-ol (6b) (84 mg, 0.25 mmol), tributyl(vinyl)tin (110 μL, 0.376 mmol, 1.5 equiv.), and Pd(PPh$_3$)$_4$ (29 mg, 0.025 mmol, 10 mol %) in toluene (2.5 mL) was refluxed under nitrogen until all starting material was consumed and precipitation of black palladium (0.5-1 h). Filtration through Celite and purification by passing through a short pad of silica gel gave pure product as an orange solid. Yield: 57 mg (81%).

EXAMPLE 11a 2-(4-Hydroxyphenyl)-4-vinylquinolin-6-ol (11a)

This compound was prepared from 6a and tributyl(vinyl) tin according to method J. Yellow solid; Yield: 69%; mp>200° C. (dec.); $^1$H-NMR (400 MHz, DMSO-d6) δ 5.69 (d, J=11.7 Hz, 1H), 6.23 (dd, J=18.3, 1.0 Hz, 1H), 6.90 (d, J=8.5 Hz, 2H), 7.31 (dd, J=9.0, 2.7 Hz, 1H), 7.35 (d, J=2.2 Hz, 1H), 7.40 (dd, J=17.3, 11.0 Hz, 1H), 7.88 (d, J=8.8 Hz, 1H), 8.01 (s, 1H), 8.11 (d, J=8.8 Hz, 2H), 9.73 (s, 1H), 9.98 (s, 1H); MS (ESI) m/z 262 ([M−H]$^-$), 264 ([M+H]$^+$); Anal. Calcd for C$_{17}$H$_{13}$NO$_2$: C, 77.55; H, 4.98; N, 5.32. Found: C, 74.26; H, 5.38; N, 4.82.

EXAMPLE 11b 2-(3-Fluoro-4-hydroxyphenyl)-4-vinylquinolin-6-ol (11b)

This compound was prepared according to method J. Orange solid; Yield: 81%; mp 160° C. (dec.); $^1$H-NMR (400 MHz, DMSO-d6) δ 5.71 (dd, J=11.0, 1.2 Hz, 1H), 6.27 (dd, J=17.3, 1.2 Hz, 1H), 7.08 (dd, J=8.8, 8.8 Hz, 1H), 7.36 (m, 3H), 7.90 (d, J=9.0 Hz, 1H), 7.96 (m, 1H), 8.06 (s, 1H), 8.08 (dd, J=13.1, 2.0 Hz, 1H), 10.04 (s, 1H), 10.18 (s, 1H); MS (ESI) m/z 280 ([M−H]$^-$), 282 ([M+H]$^+$); Anal. Calcd for C$_{17}$H$_{12}$FNO$_2$: C, 72.59; H, 4.30; N, 4.98. Found: C, 70.18; H, 4.43; N, 4.61.

EXAMPLE 12

Method K. A typical procedure is described for the synthesis of 4-ethyl-2-(4-hydroxyphenyl)quinolin-6-ol. (12a). A mixture of 2-(4-hydroxyphenyl)-4-vinylquinolin-6-ol (11a) (17 mg, 0.064 mmol) and Pd/C (10 wt. %) in EtOAc/THF (2 mL) was stirred under hydrogen atmosphere (1 atm, balloon) for 1 h. The reaction mixture was filtered through Celite, and concentrated to give a yellow solid, which was recrystallized (THF/hexane/−20° C.). Yield: 16 mg (94%).

EXAMPLE 12a

4-Ethyl-2-(4-hydroxyphenyl)quinolin-6-ol (12a)

This compound was prepared according to method K. Yellow solid; Yield: 94%; mp 140° C. (dec.); $^1$H-NMR (400 MHz, acetone-d6) δ 1.38 (t, J=7.6 Hz, 3H), 3.06 (q, J=7.6 Hz, 2H), 6.95 (d, J=8.8 Hz, 2H), 7.31 (dd, J=9.0, 2.7 Hz, 1H), 7.35 (d, J=2.7 Hz, 1H), 7.77 (s, 1H), 7.91 (d, J=9.0 Hz, 1H), 8.12 (d, J=8.8 Hz, 2H), 8.59 (s, 1H), 8.77 (s, 1H); MS (ESI) m/z 264 ([M−H]$^-$), 266 ([M+H]$^+$).

EXAMPLE 12b

4-Ethyl-2-(3-fluoro-4-hydroxyphenyl)quinolin-6-ol (12b)

This compound was prepared from 11b according to method K. Yellow solid; Yield: 97%; mp 118° C. (dec.); $^1$H-NMR (400 MHz, DMSO-d6) δ 1.35 (t, J=7.6 Hz, 3H), 3.02 (q, J=7.6 Hz, 2H), 7.07 (dd, J=9.0, 8.5 Hz, 1H), 7.26 (d, J=2.2 Hz, 1H), 7.29 (dd, J=9.0, 2.7 Hz, 1H), 7.81 (s, 1H), 7.88 (d, J=8.8 Hz, 1H), 7.89 (m, 1H), 8.00 (dd, J=13.1, 2.1 Hz, 1H), 9.95 (s, 1H), 10.16 (s, 1H); MS (ESI) m/z 282 ([M−H]$^-$), 284 ([M+H]$^+$); Anal. Calcd for C$_{17}$H$_{14}$FNO$_2$: C, 72.07; H, 4.98; N, 4.94. Found: C, 70.61; H, 4.86; N, 3.92.

EXAMPLE 13a 2-(4-Hydroxyphenyl)-4-[(trimethylsilyl)ethynyl] quinolin-6-ol (13a)

This compound was prepared from 6a and (trimethylsilylethynyl)tributyltin according to method J. Yellow powder; Yield: 83%; mp 210° C. (dec.); $^1$H-NMR (300 MHz, acetone-d6) δ 0.38 (s, 9H), 7.02 (d, J=8.7 Hz, 2H), 7.44 (dd, J=9.1, 2.7 Hz, 1H), 7.63 (d, J=2.7 Hz, 1H), 7.99 (d, J=9.1 Hz, 1H), 8.05 (s, 1H), 8.18 (d, J=8.7 Hz, 2H), 8.70 (s, 1H), 9.15 (s, 1H); MS (ESI) m/z 332 ([M−H]$^-$), 334 ([M+H]$^+$); Anal. Calcd for C$_{20}$H$_{19}$NO$_2$Si: C, 72.04; H, 5.74; N, 4.20. Found: C, 71.67; H, 5.79; N, 4.07.

EXAMPLE 13b 2-(3-Fluoro-4-hydroxyphenyl)-4-[(trimethylsilyl) ethynyl]quinolin-6-ol (13b)

This compound was prepared from 6b and (trimethylsilylethynyl)tributyltin according to method J. Red powder; Yield: 94%; $^1$H-NMR (300 MHz, acetone-d6) δ 0.43 (s, 9H), 7.21 (dd, J=8.8, 8.8 Hz, 1H), 7.51 (dd, J=9.1, 2.7 Hz, 1H), 7.68 (d, J=2.7 Hz, 1H), 8.05 (m, 1H), 8.07 (d, J=9.0 Hz, 1H), 8.13 (s, 1H), 8.18 (dd, J=12.8, 2.1 Hz, 1H), 9.05 (s, 1H), 9.26 (s, 1H); MS (ESI) m/z 350 ([M−H]$^-$), 352 ([M+H]$^+$).

EXAMPLE 14

Method L. A typical procedure is described for the synthesis of 4-ethynyl-2-(4-hydroxyphenyl)quinolin-6-ol (14a). To a solution of 2-(4-hydroxyphenyl)-4-[(trimethylsilyl)ethynyl]quinolin-6-ol (13a) (88 mg, 0.26 mmol) in MeOH (3 mL) was added K$_2$CO$_3$ (146 mg, 1.06 mmol, 4 equiv.) and the mixture was stirred for 30 min at rt. The reaction mixture was quenched with aq. NH$_4$Cl (5 mL) and extracted with EtOAc. The organic layer was washed with water, brine, dried (Na$_2$SO$_4$), filtered and concentrated to give a crude solid, which was purified by passing through a short pad of silica gel to give pure product as a yellow solid. Yield: 66 mg (96%).

EXAMPLE 14a

4-Ethynyl-2-(4-hydroxyphenyl)quinolin-6-ol (14a)

This compound was prepared according to method L. Yellow solid; Yield: 96%; mp 260° C. (dec.); $^1$H-NMR (300 MHz, DMSO-d6) δ 4.96 (s, 1H), 6.90 (d, J=8.7 Hz, 2H), 7.34 (dd, J=9.0, 2.6 Hz, 1H), 7.44 (d, J=2.6 Hz, 1H), 7.91 (d, J=9.0 Hz, 1H), 8.08 (s, 1H), 8.09 (d, J=8.7 Hz, 2H), 9.81 (s, 1H), 10.24 (s, 1H); MS (ESI) m/z 260 ([M−H]$^-$), 262 ([M+H]$^+$); Anal. Calcd for C$_{17}$H$_{11}$NO$_2$: C, 78.15; H, 4.24; N, 5.36. Found: C, 76.74; H, 4.05; N, 5.04.

EXAMPLE 14b

4-Ethynyl-2-(3-fluoro-4-hydroxyphenyl)quinolin-6-ol (14b)

This compound was prepared from 13b according to method L. Yellow solid; Yield: 91%; mp 222° C. (dec.); $^1$H-NMR (300 MHz, DMSO-d6) δ 4.98 (s, 1H), 7.07 (dd, J=8.8, 8.8 Hz, 1H), 7.36 (dd, J=9.1, 2.7 Hz, 1H), 7.45 (d, J=2.6 Hz, 1H), 7.92 (m, 1H), 7.94 (d, J=9.0 Hz, 1H), 8.04 (dd, J=13.0, 2.0 Hz, 1H), 8.14 (s, 1H), 10.28 (s, 1H), 10.31 (s, 1H); $^{19}$F-NMR (300 MHz, DMSO-d6) δ −136.44 (dd, J=13.2, 8.8 Hz); MS (ESI) m/z 278 ([M−H]$^-$), 280 ([M+H]$^+$); Anal. Calcd for $C_{17}H_{10}FNO_2$: C, 73.11; H, 3.61; N, 5.02. Found: C, 70.84; H, 3.84; N, 4.71.

EXAMPLE 14c 2-(3,5-Difluoro-4-hydroxyphenyl)-4-ethynylquinolin-6-ol (14c)

This compound was prepared from 6c following a combination of method J using (trimethylsilylethynyl)tributyltin and method L. Yellow solid; Yield: 87%; mp 220° C. (dec.); $^1$H-NMR (300 MHz, acetone-d6) δ 4.39 (s, 1H), 7.45 (dd, J=9.1, 2.7 Hz, 1H), 7.60 (d, J=2.7 Hz, 1H), 7.95 (d, J=10.1 Hz, 1H), 7.96 (d, J=7.1 Hz, 1H), 8.00 (d, J=9.2 Hz, 1H), 8.14 (s, 1H), 9.18 (s, 1H), 9.31 (s, 1H); MS (ESI) m/z 296 ([M−H]$^-$), 298 ([M+H]$^+$).

EXAMPLE 15

2-(3-Fluoro-4-hydroxyphenyl)-4-(phenylethynyl)quinolin-6-ol (15)

This compound was prepared from 6b and tributyl(phenylethynyl)tin according to method J. Orange powder; Yield: 92%; mp 125-129° C.; $^1$H-NMR (300 MHz, DMSO-d6) δ 7.08 (dd, J=8.8, 8.8 Hz, 1H), 7.36 (dd, J=9.0, 2.6 Hz, 1H), 7.53 (m, 3H), 7.59 (d, J=2.6 Hz, 1H), 7.74 (m, 2H), 7.94 (d, J=9.1 Hz, 2H), 8.05 (dd, J=13.0, 1.8 Hz, 1H), 8.18 (s, 1H), 10.23 (s, 1H), 10.26 (s, 1H); $^{19}$F-NMR (300 MHz, DMSO-d6) δ −136.48 (dd, J=13.7, 9.2 Hz); MS (ESI) m/z 354 ([M−H]$^-$), 356 ([M+H]$^+$); Anal. Calcd for $C_{23}H_{14}FNO_2$: C, 77.74; H, 3.97; N, 3.94. Found: C, 76.45; H, 3.88; N, 3.77.

EXAMPLE 16

Method M. A typical procedure is described for the synthesis of 4-acetyl-2-(4-hydroxyphenyl)quinolin-6-ol (16a). A mixture of 4-bromo-2-(4-hydroxyphenyl)quinolin-6-ol (6a) (111 mg, 0.350 mmol), (1-ethoxyvinyl)tributyltin (152 mg, 0.42 mmol, 1.2 equiv.), and Pd(PPh$_3$)$_4$ (40 mg, 0.035 mmol, 10 mol %) in toluene (3 mL) was refluxed under nitrogen until all starting material was consumed and precipitation of black palladium (0.5-1 h). Filtration through Celite and removal of solvent gave a dark residue, which was redissolved in THF (5 mL). To this solution was added HCl (1N, 1 mL) and the mixture was stirred for 30 min at rt. After concentration, aq. NaHCO$_3$ was added and the mixture was extracted with EtOAc. The organic layer was washed with brine, dried (Na$_2$SO$_4$), filtered and concentrated to give a crude solid, which was purified by passing through a short pad of silica gel to give pure product as a yellow solid. Yield: 76 mg (78%).

EXAMPLE 16a

4-Acetyl-2-(4-hydroxyphenyl)quinolin-6-ol (16a)

This compound was prepared according to method M. Yellow solid; Yield: 78%; mp>245° C. (dec.); $^1$H-NMR (300 MHz, DMSO-d6) δ 2.81 (s, 3H), 6.92 (d, J=8.7 Hz, 2H), 7.33 (dd, J=9.1, 2.7 Hz, 1H), 7.71 (d, J=2.7 Hz, 1H), 7.93 (d, J=9.1 Hz, 1H), 8.15 (d, J=8.7 Hz, 2H), 8.33 (s, 1H), 9.84 (s, 1H), 10.14 (s, 1H); MS (ESI) m/z 278 ([M−H]$^-$), 280 ([M+H]+): Anal. Calcd for $C_{17}H_{13}NO_3$: C, 73.11; H, 4.69; N, 5.01. Found: C, 71.75; H, 4.84; N, 4.47.

EXAMPLE 16b

4-Acetyl-2-(3-fluoro-4-hydroxyphenyl)quinolin-6-ol (16b)

This compound was prepared from 6b according to method M. Yellow solid; Yield: 83%; mp 241-244° C. (dec.); $^1$H-NMR (400 MHz, DMSO-d6) δ 2.82 (s, 3H), 7.11 (dd, J=8.9, 8.7 Hz, 1H), 7.35 (dd, J=9.1, 2.7 Hz, 1H), 7.71 (d, J=2.7 Hz, 1H), 7.95 (d, J=9.1 Hz, 1H), 8.00 (m, 1H), 8.12 (dd, J=12.9, 2.1 Hz, 1H), 8.36 (s, 1H), 10.18 (s, 1H), 10.27 (s, 1H); $^{19}$F-NMR (300 MHz, DMSO-d6) δ −136.51 (dd, J=12.9, 9.2 Hz); MS (ESI) m/z 296 ([M−H]$^-$), 298 ([M+H]$^+$); Anal. Calcd for $C_{17}H_{12}FNO_3$: C, 68.68; H, 4.07; N, 4.71. Found: C, 74.32, H, 4.09; N, 4.87.

EXAMPLE 17

Method N. A typical procedure is described for the synthesis of 4-(1-hydroxyethyl)-2-(4-hydroxyphenyl)quinolin-6-ol (17a). To a solution of 4-acetyl-2-(4-hydroxyphenyl)quinolin-6-ol (16a) (34 mg, 0.12 mmol) in EtOH (3 mL) was added NaBH$_4$ (5 mg, 0.13 mmol) and the mixture was stirred at rt for 30 min. Aq. NaHCO$_3$ was slowly added to quench the reaction and the mixture was extracted with EtOAc. The organic layer was washed with brine, dried (Na$_2$SO$_4$), filtered and concentrated to give a crude solid, which was purified by passing through a short pad of silica gel to give pure product as a yellow powder. Yield: 34 mg (98%).

EXAMPLE 17a 4-(1-Hydroxyethyl)-2-(4-hydroxyphenyl)quinolin-6-ol (17a)

This compound was prepared according to method N. Yellow powder; Yield: 98%; mp 150-154° C.; $^1$H-NMR (300 MHz, DMSO-d6) δ 1.49 (d, J=6.4 Hz, 3H), 5.33 (dq, J=6.3, 4.3 Hz, 1H), 5.55 (d, J=4.3 Hz, 1H), 6.90 (d, J=8.7 Hz, 2H), 7.25 (d, J=2.5 Hz, 1H), 7.29 (m, 1H), 7.87 (d, J=8.8 Hz, 1H), 7.98 (s, 1H), 8.03 (d, J=8.7 Hz, 2H), 9.75 (s, 1H), 9.92 (s, 1H); MS (ESI) m/z 280 ([M−H]$^-$), 282 ([M+H]$^+$); Anal. Calcd for $C_{17}H_{15}NO_3$: C, 72.58; H, 5.37; N, 4.98. Found: C, 70.68; H, 5.16; N, 4.33.

EXAMPLE 17b

2-(3-Fluoro-4-hydroxyphenyl)-4-(1-hydroxyethyl)quinolin-6-ol (17b)

This compound was prepared from 16b according to method N. Yellow powder; Yield: 98%; mp 155-165° C. (dec.); $^{1}$H-NMR (300 MHz, DMSO-d6) δ 1.49 (d, J=6.4 Hz, 3H), 5.32 (dq, J=6.1, 4.2 Hz, 1H), 5.55 (d, J=4.2 Hz, 1H), 7.09 (dd, J=8.8, 8.8 Hz, 1H), 7.23 (m, 2H), 7.84 (d, J=8.4 Hz, 1H), 7.89 (d, J=8.8 Hz, 1H), 7.96 (dd, J=13.1, 1.9 Hz, 1H), 8.00 (s, 1H), 9.98 (s, 1H), 10.22 (s, 1H); $^{19}$F-NMR (400 MHz, DMSO-d6) δ −136.52 (dd, J=12.9, 9.2 Hz); MS (ESI) m/z 298 ([M−H]$^{-}$), 300 ([M+H]$^{+}$); Anal. Calcd for $C_{17}H_{14}FNO_3$: C, 68.22; H, 4.71; N, 4.68. Found: C, 67.50; H, 4.79; N, 4.07.

EXAMPLE 18

2-(3-Fluoro-4-hydroxyphenyl)-4-thiazol-2-yl-quinolin-6-ol (18)

This compound was prepared from 6b and 2-tributylstannylthiazole according to method J. Yellow powder; Yield: 56%; mp>280° C. (dec.); $^{1}$H-NMR (400 MHz, DMSO-d6) δ 7.10 (t, J=8.8 Hz, 1H), 7.38 (dd, J=9.1, 2.7 Hz, 1H), 7.95-8.00 (m, 2H), 8.07-8.12 (m, 3H), 8.21 (m, 2H), 10.18 (s, 1H), 10.26 (s, 1H); MS (ESI) m/z 337 ([M−H]$^{-}$), 339 ([M+H]$^{+}$); Anal. Calcd for $C_{18}H_{11}FN_2O_2S$: C, 63.90; H, 3.28; N, 8.28. Found: C, 62.6; H, 3.43; N, 7.59.

EXAMPLE 19

2-(4-Hydroxyphenyl)-4-methoxyquinolin-6-ol (19)

Method O. A solution of 4-chloro-2-(4-hydroxyphenyl)quinolin-6-ol (5a) (36 mg, 0.132 mmol) and NaOMe (71 mg, 1.32 mmol) in MeOH (6 mL) was heated at 150° C. in a sealed reaction vessel for 24 h. After cooling to rt, aq. NH$_4$Cl was slowly added, and the mixture was extracted with EtOAc. The organic layer was washed with water, brine, dried (Na$_2$SO$_4$), filtered and concentrated to give a crude solid, which was purified by silica gel chromatography give pure product as a yellow solid. $^{1}$H-NMR (300 MHz, DMSO-d6) δ 4.10 (s, 3H), 6.89 (d, J=8.7 Hz, 2H), 7.24 (dd, J=9.0, 2.8 Hz, 1H), 7.30 (d, J=2.7 Hz, 1H), 7.35 (s, 1H), 7.79 (d, J=9.0 Hz, 1H), 8.08 (d, J=8.7 Hz, 2H), 9.74 (s, 1H), 9.89 (s, 1H); MS (ESI) m/z 266 ([M−H]$^{-}$), 268 ([M+H]$^{+}$).

EXAMPLE 20

Method P: General procedure for Pd-catalyzed coupling reactions of 4-bromoquinolines with boronic acids. A typical procedure is described for the synthesis of 2-(3-fluoro-4-hydroxyphenyl)-4-phenylquinolin-6-ol (20). To a suspension of Pd(PPh$_3$)$_4$ (23 mg, 0.020 mmol, 10 mol %) in DME (3 mL) was added 4-bromo-2-(3-fluoro-4-hydroxyphenyl)quinolin-6-ol (6b) (67 mg, 0.20 mmol) and the mixture was stirred for 10 min at rt. To this mixture were added sequentially phenylboronic acid (30 mg, 0.24 mmol, 1.2 equiv.) and aq. Na$_2$CO$_3$ (2 M soln, 5 equiv.) and the mixture was refluxed until all starting material was consumed and precipitation of black palladium (2-3 h). After cooling, aq. NH$_4$Cl was added and the reaction mixture extracted with EtOAc. The organic layer was washed with water, brine, dried (Na$_2$SO$_4$), filtered and concentrated to give a crude solid, which was purified by passing through a short pad of silica gel to give pure product as a yellow powder. Yield: 60 mg (91%).

2-(3-Fluoro-4-hydroxyphenyl)-4-phenylquinolin-6-ol (20)

This compound was prepared according to method P. Yellow powder; Yield: 91%; mp 158-162° C.; $^{1}$H-NMR (400 MHz, DMSO-d6) δ 7.07 (dd, J=8.8, 8.8 Hz, 1H), 7.10 (d, J=2.7 Hz, 1H), 7.32 (dd, J=9.1, 2.7 Hz, 1H), 7.57 (m, 5H), 7.85 (s, 1H), 7.94 (dd, J=8.4, 2.1 Hz, 1H), 7.97 (d, J=9.1 Hz, 1H), 8.08 (dd, J=12.9, 2.1 Hz, 1H), 9.93 (s, 1H), 10.19 (s, 1H); $^{19}$F-NMR (400 MHz, DMSO-d6) δ −136.61 (dd, J=13.0, 8.7 Hz); MS (ESI) m/z 330 ([M−H]$^{-}$), 332 ([M+H]$^{+}$); Anal. Calcd for $C_{21}H_{14}FNO_2$: C, 76.12; H, 4.26; N, 4.23. Found: C, 74.52; H, 3.57; N, 3.77.

EXAMPLE 21

2-(3-Fluoro-4-hydroxyphenyl)-4-(4-methylphenyl)quinolin-6-ol (21)

This compound was prepared from 6b using p-tolylboronic acid according to method P. Orange powder; Yield: 85%; mp 184-188° C.; $^{1}$H-NMR (300 MHz, DMSO-d6) δ 2.44 (s, 3H), 7.07 (dd, J=8.8, 8.8 Hz, 1H), 7.12 (d, J=2.6 Hz, 1H), 7.31 (dd, J=9.1, 2.6 Hz, 1H), 7.40 (d, J=8.0 Hz, 2H), 7.49 (d, J=8.0 Hz, 2H), 7.82 (s, 1H), 7.94 (dd, J=8.4, 2.1 Hz, 1H), 7.96 (d, J=9.0 Hz, 1H), 8.07 (dd, J=13.0, 2.0 Hz, 1H), 9.91 (s, 1H), 10.21 (s, 1H); MS (ESI) m/z 344 ([M−H]$^{-}$), 346 ([M+H]$^{+}$); Anal. Calcd for $C_{22}H_{16}FNO_2$: C, 76.51; H, 4.67; N, 4.06. Found: C, 75.55; H, 4.50; N, 3.74.

EXAMPLE 22

2-(3-Fluoro-4-hydroxyphenyl)-4-(4-fluorophenyl)quinolin-6-ol (22)

This compound was prepared from 6b using 4-fluorophenylboronic acid according to method P. Orange powder; Yield: 90%; mp 240-243° C.; $^{1}$H-NMR (300 MHz, DMSO-d6) δ 7.05 (d, J=2.6 Hz, 1H), 7.07 (dd, J=8.9, 8.7 Hz, 1H), 7.32 (dd, J=9.0, 2.6 Hz, 1H), 7.44 (dd, J=8.9, 8.9 Hz, 2H), 7.63 (m, 2H), 7.86 (s, 1H), 7.95 (dd, J=8.4, 1.9 Hz, 1H), 7.97 (d, J=9.1 Hz, 1H), 8.08 (dd, J=13.0, 2.0 Hz, 1H), 9.96 (s, 1H), 10.21 (s, 1H); MS (ESI) m/z 348 ([M−H]$^{-}$), 350 ([M+H]$^{+}$); Anal. Calcd for $C_{21}H_{13}F_2NO_2$: C, 72.20; H, 3.75; N, 4.01. Found: C, 69.48; H, 3.81; N, 3.68.

EXAMPLE 23

4-(4-Chlorophenyl)-2-(3-fluoro-4-hydroxyphenyl)quinolin-6-ol (23)

This compound was prepared from 6b using 4-chlorophenylboronic acid according to method P. Orange powder; Yield: 87%; mp 140-147° C.; $^{1}$H-NMR (400 MHz, DMSO-d6) δ 7.03 (d, J=2.7 Hz, 1H), 7.06 (t, J=8.8 Hz, 1H), 7.32 (dd, J=9.1, 2.7 Hz, 1H), 7.63 (d, J=8.8 Hz, 2H), 7.67 (d, J=8.7 Hz, 2H), 7.87 (s, 1H), 7.93-7.98 (m, 2H), 8.07 (dd, J=13.0, 2.1 Hz, 1H), 9.94 (s, 1H), 10.20 (s, 1H); MS (ESI) m/z 364/366 ([M−H]$^{-}$), 366/368 ([M+H]$^{+}$); Anal. Calcd for $C_{21}H_{13}ClFNO_2$: C, 68.95; H, 3.58; N, 3.83. Found: C, 68.23; H, 3.54; N, 3.78.

EXAMPLE 24

4-(4-Cyanophenyl)-2-(3-fluoro-4-hydroxyphenyl)quinolin-6-ol (24)

This compound was prepared from 6b using 4-cyanophenylboronic acid according to method P. Yellow powder; Yield: 52%; mp 266-267° C.; $^1$H-NMR (400 MHz, DMSO-d6) δ 6.97 (d, J=2.7 Hz, 1H), 7.07 (t, J=8.8 Hz, 1H), 7.34 (dd, J=9.0, 2.6 Hz, 1H), 7.82 (d, J=8.5 Hz, 2H), 7.92 (s, 1H), 7.95-8.00 (m, 2H), 8.07-8.10 (m, 3H), 10.00 (s, 1H), 10.21 (s, 1H); MS (ESI) m/z 355 ([M−H]$^−$), 357 ([M+H]$^+$); Anal. Calcd for $C_{22}H_{13}FN_2O_2$: C, 74.15; H, 3.68; N, 7.86. Found: C, 73.69; H, 3.53; N, 7.86.

EXAMPLE 25

2-(3-Fluoro-4-hydroxyphenyl)-4-(4-trifluoromethylphenyl)quinolin-6-ol (25)

This compound was prepared from 6b using 4-trifluoromethylphenylboronic acid according to method P. Yellow crystals; Yield: 76%; mp 299-300° C.; $^1$H-NMR (400 MHz, DMSO-d6) δ 7.07 (dd, J=8.8, 8.8 Hz, 1H), 7.12 (d, J=2.6 Hz, 1H), 7.31 (dd, J=9.1, 2.6 Hz, 1H), 7.40 (d, J=8.0 Hz, 2H), 7.49 (d, J=8.0 Hz, 2H), 7.82 (s, 1H), 7.94 (dd, J=8.4, 2.1 Hz, 1H), 7.96 (d, J=9.0 Hz, 1H), 8.07 (dd, J=13.0, 2.0 Hz, 1H), 9.91 (s, 1H), 10.21 (s, 1H); $^{19}$F-NMR (400 MHz, DMSO-d6) δ −136.58 (dd, J=13.2, 9.3 Hz), −61.43 (s); MS (ESI) m/z 398 ([M−H]$^−$), 400 ([M+H]$^+$); Anal. Calcd for $C_{22}H_{13}F_4NO_2$: C, 66.17; H, 3.28; N, 3.51. Found: C, 66.09; H, 3.41; N, 3.45.

EXAMPLE 26

2-(3-Fluoro-4-hydroxyphenyl)-4-thiophen-3-yl-quinolin-6-ol (26)

This compound was prepared from 6b using 3-thipheneboronic acid according to method P. Orange powder; Yield: 95%; mp>160° C. (dec.); $^1$H-NMR (400 MHz, DMSO-d6) δ 7.06 (t, J=8.8 Hz, 1H), 7.30-7.33 (m, 2H), 7.50 (dd, J=4.9, 1.2 Hz, 1H), 7.82 (dd, J=4.9, 3.0 Hz, 1H), 7.90-7.95 (m, 4H), 8.06 (dd, J=13.0, 2.1 Hz, 1H), 9.97 (s, 1H), 10.19 (s, 1H); MS (ESI) m/z 336 ([M−H]$^−$), 338 ([M+H]$^+$); Anal. Calcd for $C_{19}H_{12}FNO_2S$: C, 67.64; H, 3.59; N, 4.15. Found: C, 66.81; H, 4.14; N, 3.58.

EXAMPLE 27

2-(3-Fluoro-4-hydroxyphenyl)-4-(4-pyridinyl)quinolin-6-ol (27)

This compound was prepared from 6b using 4-pyridinylboronic acid according to method P. Yellow powder; Yield: 20%; mp>350° C. (dec.); $^1$H-NMR (400 MHz, DMSO-d6) δ 7.02 (d, J=2.6 Hz, 1H), 7.07 (t, J=8.8 Hz, 1H), 7.34 (dd, J=9.0, 2.6 Hz, 1H), 7.64 (d, J=5.9 Hz, 2H), 7.93 (s, 1H), 7.95-8.00 (m, 2H), 8.08 (dd, J=13.0, 2.1 Hz, 1H), 8.79 (d, J=3.9 Hz, 2H), 10.02 (s, 1H), 10.22 (s, 1H); MS (ESI) m/z 331 ([M−H]$^−$), 333 ([M+H]$^+$); Anal. Calcd for $C_{20}H_{13}FN_2O_2$: C, 72.28; H, 3.94; N, 8.43. Found: C, 70.79; H, 4.08; N, 7.87.

EXAMPLE 28

2-(3-Fluoro-4-hydroxyphenyl)-4-(5-pyrimidinyl)quinolin-6-ol (28)

This compound was prepared from 6b using 5-pyrimidinylboronic acid according to method P. Yellow powder; Yield: 34%; mp>340° C. (dec.); $^1$H-NMR (400 MHz, DMSO-d6) δ 7.00 (d, J=2.6 Hz, 1H), 7.08 (t, J=8.8 Hz, 1H), 7.36 (dd, J=9.0, 2.6 Hz, 1H), 7.98-8.02 (m, 2H), 8.08 (s, 1H), 8.11 (dd, J=13.1, 2.2 Hz, 1H), 9.11 (s, 2H), 9.37 (s, 1H), 10.07 (s, 1H), 10.24 (s, 1H); MS (ESI) m/z 332 ([M−H]$^−$), 334 ([M+H]$^+$); Anal. Calcd for $C_{19}H_{12}FN_3O_2$: C, 68.47; H, 3.63; N, 12.61. Found: C, 65.37; H, 3.98; N, 11.30.

EXAMPLE 29

6-Methoxy-2-(4-methoxyphenyl)-quinoline (29)

Method Q. A solution of p-anisyl bromide (17.62 g, 94.2 mmol) in ether (80 mL) was cooled to −78° C. n-Butyllithium (42.8 mL, 2.5 M in hexanes, 107 mmol) was slowly added, stirred for 15 min, after which 6-methoxyquinoline (10.0 g, 62.8 mmol) was added dropwise and the reaction mixture was warmed to rt. The reaction was quenched with water and the organic layer was dried ($Na_2SO_4$), passed through a pad of silica gel and concentrated. Purification by silica gel column chromatography (20% EtOAc/hexanes) afforded pure product as a yellow solid. Yield: 1.71 g (10%); $^1$H-NMR (400 MHz, DMSO-d6) δ 3.84 (s, 3H), 3.91 (s, 3H), 7.09 (d, J=9.0 Hz, 2H), 7.37-7.41 (m, 2H), 7.94 (d, J=9.0, 1H), 8.04 (d, J=8.8 Hz, 1H), 8.20 (d, J=9.0 Hz, 2H), 8.29 (d, J=8.1 Hz, 1H); MS (ESI) m/z 266 ([M+H]$^+$); Anal. Calcd for $C_{17}H_{15}NO_2$: C, 76.96; H, 5.70; N, 5.28. Found: C, 77.11; H, 5.53; N, 4.99.

EXAMPLE 30

5-Bromo-6-methoxy-2-(4-methoxyphenyl)-quinoline (30)

Method R. To a solution of 6-methoxy-2-(4-methoxyphenyl)-quinoline (29) (408 mg, 1.54 mmol) in acetonitrile (5 mL) was added NBS (288 mg, 1.62 mmol, 1.05 equiv.) portionwise. After the addition was complete, the reaction mixture was allowed stirred at rt under nitrogen until all starting material was consumed (2-4 h). Solvent was removed under reduced pressure. Water and aq. $NaHCO_3$ were added and the mixture was extracted with EtOAc. The organic layer was washed with brine, dried ($Na_2SO_4$), filtered through a short pad of silica gel and concentrated to give pure product as a yellow solid. Yield: 400 mg (76%); $^1$H-NMR (400 MHz, DMSO-d6) δ 3.85 (s, 3H), 4.03 (s, 3H), 7.11 (d, J=9.0 Hz, 2H), 7.78 (d, J=9.5 Hz, 1H), 8.11 (dd, J=9.3, 1.0 Hz, 1H), 8.20 (d, J=9.0 Hz, 1H), 8.23 (d, J=9.0 Hz, 2H), 8.47 (dd, J=9.0, 0.7 Hz, 1H); MS (ESI) m/z 344/346 ([M+H]$^+$); Anal. Calcd for $C_{17}H_{14}BrNO_2$: C, 59.32; H, 4.10, N, 4.07. Found: C, 60.95; H, 4.43; N, 3.57.

EXAMPLE 31

5-Chloro-2-(4-hydroxyphenyl)quinolin-6-ol (31)

This compound was prepared from 30 using Pyr./HCl according to method I. Tan solid; Yield: 80%; mp 215-216° C.; $^1$H-NMR (400 MHz, DMSO-d6) δ 6.91 (d, J=8.8 Hz, 2H), 7.51 (d, J=9.0 Hz, 1H), 7.87 (dd, J=9.2, 0.7 Hz, 1H), 8.09 (m, 3H), 8.41 (dd, J=9.0, 0.7 Hz, 1H), 9.81 (s, 1H), 10.65 (s, 1H);

MS (ESI) m/z 270/272 ([M−H]−), 272/274 ([M+H]+); Anal. Calcd for $C_{15}H_{10}ClNO_2$: C, 66.31; H, 3.71; N, 5.16. Found: C, 65.27; H, 4.28; N, 4.94.

EXAMPLE 32

5-Bromo-2-(4-hydroxyphenyl)quinolin-6-ol (32)

This compound was prepared from 30 according to method E. Yellow solid; Yield: 71%; mp 187-188° C.; $^1$H-NMR (400 MHz, DMSO-d6) δ 6.91 (d, J=8.8 Hz, 2H), 7.51 (d, J=9.0 Hz, 1H), 7.91 (dd, J=9.2, 0.7 Hz, 1H), 8.09 (d, J=9.0 Hz, 3H), 8.38 (dd, J=8.9, 0.7 Hz, 1H), 9.82 (s, 1H), 10.75 (s, 1H); MS (ESI) m/z 314/316 ([M−H]−), 316/318 ([M+H]+); Anal. Calcd for $C_{15}H_{10}BrNO_2$: C, 56.99; H, 3.19; N, 4.43. Found: C, 55.31; H, 3.39; N, 3.51.

EXAMPLE 33

Method S. A typical procedure is described for the synthesis of 3-chloro-6-methoxy-2-(4-methoxyphenyl)quinolin-4-ol (33a). To a stirred suspension of 6-methoxy-2-(4-methoxyphenyl)quinolin-4-ol (2a) (1.83 g, 6.50 mmol) in DMF (20 mL) at 80° C. under nitrogen was added a solution of N-chlorosuccinimide (0.911 g, 6.82 mmol, 1.05 equiv.) in DMF (10 mL) dropwise via an addition funnel. After the addition was complete, the reaction mixture was stirred at 80° C. for an additional 2 h. Upon cooling to rt, water was added to the reaction mixture. The yellow precipitate formed was collected by filtration, washed with water and dried in vacuo. Yield: 1.94 g (95%).

EXAMPLE 33a

3-Chloro-6-methoxy-2-(4-methoxyphenyl)quinolin-4-ol (33a)

This compound was prepared according to method S. White solid; Yield: 95%; mp>300° C. (dec.); $^1$H-NMR (300 MHz, DMSO-d6) δ 3.86 (s, 3H), 3.87 (s, 3H), 7.14 (d, J=8.8 Hz, 2H), 7.35 (dd, J=9.1, 2.9 Hz, 1H), 7.53 (d, J=2.9 Hz, 1H), 7.61 (d, J=8.8 Hz, 2H), 7.64 (d, J=9.1 Hz, 1H), 12.14 (s, 1H); MS (ESI) m/z 314/316 ([M−H]−), 316/318 ([M+H]+); Anal. Calcd for $C_{17}H_{14}ClNO_3$: C, 64.67; H, 4.47; N, 4.44. Found: C, 64.18; H, 4.40; N, 4.35.

EXAMPLE 33b

3-Chloro-2-(3-fluoro-4-methoxyphenyl)-6-methoxyquinolin-4-ol (33b)

This compound was prepared from 2b according to method S. Ivory solid; Yield: 98%; mp 320° C. (dec.); $^1$H-NMR (300 MHz, DMSO-d6) δ 3.87 (s, 3H), 3.95 (s, 3H), 7.36 (dd, J=9.1, 3.0 Hz, 1H), 7.38 (dd, J=9.0, 8.8 Hz, 1H), 7.49 (m, 1H), 7.53 (d, J=2.9 Hz, 1H), 7.61 (dd, J=12.1, 2.1 Hz, 1H), 7.64 (d, J=8.9 Hz, 1H), 12.20 (s, 1H); MS (ESI) m/z 332/334 ([M−H]−), 334/336 ([M+H]+); Anal. Calcd for $C_{17}H_{13}ClFNO_3$: C, 61.18; H, 3.93; N, 4.20. Found: C, 60.72; H, 4.11; N, 4.38.

EXAMPLE 34a

4-Bromo-3-chloro-6-methoxy-2-(4-methoxyphenyl)quinoline (34a)

This compound was prepared from 33a according to method D. White solid; Yield: 87%; mp 184-185° C.; $^1$H-NMR (300 MHz, CDCl$_3$) δ 3.88 (s, 3H), 4.00 (s, 3H), 7.01 (d, J=8.8 Hz, 2H), 7.37 (dd, J=9.1, 2.8 Hz, 1H), 7.42 (d, J=2.7 Hz, 1H), 7.69 (d, J=8.8 Hz, 2H), 8.00 (d, J=9.1 Hz, 1H); MS (ESI) m/z 378/380/382 ([M+H]+); Anal. Calcd for $C_{17}H_{13}BrClNO_2$: C, 53.92; H, 3.46; N, 3.70. Found: C, 53.99; H, 3.31; N, 3.53.

EXAMPLE 34b

4-Bromo-3-chloro-2-(3-fluoro-4-methoxyphenyl)-6-methoxyquinoline (34b)

This compound was prepared from 33b according to method D. White solid; Yield: 84%; mp 197-199° C.; $^1$H-NMR (300 MHz, CDCl$_3$) δ 3.97 (s, 3H), 4.00 (s, 3H), 7.07 (dd, J=9.0, 8.4 Hz, 1H), 7.39 (dd, J=9.1, 2.8 Hz, 1H), 7.43 (d, J=2.6 Hz, 1H), 7.52 (m, 2H), 7.99 (d, J=9.1 Hz, 1H); $^{19}$F-NMR (400 MHz, CDCl$_3$) δ −135.76 (dd, J=12.2, 9.2 Hz); MS (ESI) m/z 396/398/400 ([M+H]+); Anal. Calcd for $C_{17}H_{12}BrClFNO_2$: C, 51.48; H, 3.05; N, 3.53. Found: C, 51.63; H, 2.92; N, 3.38.

EXAMPLE 35a

4-Bromo-3-chloro-2-(4-hydroxyphenyl)quinolin-6-ol (35a)

This compound was prepared from 34a according to method E. Yellow solid; Yield: 90%; mp>300° C. (dec.); $^1$H-NMR (400 MHz, DMSO-d6) 6.88 (d, J=8.8 Hz, 2H), 7.39 (m, 2H), 7.54 (d, J=8.7 Hz, 2H), 7.93 (d, J=9.8 Hz, 1H), 9.81 (s, 1H), 10.59 (s, 1H); MS (ESI) m/z 348/350/354 ([M−H]−), 350/352/354 ([M+H]+); Anal. Calcd for $C_{15}H_9BrClNO_2$: C, 51.39; H, 2.59; N, 4.00. Found: C, 51.13; H, 2.69; N, 3.78.

EXAMPLE 35b

4-Bromo-3-chloro-2-(3-fluoro-4-hydroxyphenyl)quinolin-6-ol (35b)

This compound was prepared from 34b according to method E. Yellow powder; Yield: 81%; mp 256° C. (dec.); $^1$H-NMR (300 MHz, DMSO-d6) δ 7.07 (dd, J=8.8, 8.7 Hz, 1H), 7.38 (m, 3H), 7.49 (dd, J=12.2, 2.0 Hz, 1H), 7.95 (d, J=9.8 Hz, 1H), 10.26 (s, 1H), 10.63 (s, 1H); MS (ESI) m/z 366/368/370 ([M−H]−), 368/370/372 ([M+H]+); Anal. Calcd for $C_{15}H_8BrClFNO_2$: C, 48.88; H, 2.19; N, 3.80. Found: C, 49.08; H, 2.24; N, 3.49.

EXAMPLE 36

3-Chloro-4-(4-fluorophenyl)-2-(4-hydroxyphenyl)quinolin-6-ol (36)

This compound was prepared from 35a and 4-fluorophenylboronic acid according to method P. White solid; Yield: 95%; mp 295-296° C.; 1H-NMR (300 MHz, DMSO-d6) δ 6.55 (d, J=2.6 Hz, 1H), 6.87 (d, J=8.6 Hz, 2H), 7.31 (dd, J=9.1, 2.6 Hz, 1H), 7.45 (m, 4H), 7.57 (d, J=8.6 Hz, 2H), 7.92 (d, J=9.1 Hz, 1H), 9.73 (s, 1H), 10.07 (s, 1H); MS (ESI) m/z 364/366 ([M−H]−), 366/368 ([M+H]+); Anal. Calcd for $C_{21}H_{13}ClFNO_2$: C, 68.96; H, 3.58; N, 3.83. Found: C, 68.19; H, 3.56; N, 3.74.

EXAMPLE 37

3-Chloro-4-cyano-2-(3-fluoro-4-hydroxyphenyl)quinolin-6-ol (37)

This compound was prepared from 34b according to method F and method G (using Pyr./HCl). Yellow solid; Yield: 41% (for two steps); mp 325-328° C. (dec.); $^1$H-NMR (300 MHz, DMSO-d6) δ 7.10 (dd, J=8.8, 8.7 Hz, 1H), 7.27 (d, J=2.5 Hz, 1H), 7.43 (dd, J=8.4, 1.4 Hz, 1H), 7.49 (dd, J=9.2, 2.5 Hz, 1H), 7.55 (dd, J=12.2, 2.0 Hz, 1H), 8.04 (d, J=9.1 Hz, 1H), 10.37 (s, 1H), 10.97 (s, 1H); MS (ESI) m/z 313 ([M−H]$^-$), 315 ([M+H]$^+$); Anal. Calcd for $C_{16}H_8ClFN_2O_2$: C, 61.07; H, 2.56; N, 8.90. Found: C, 60.80; H, 2.57; N, 8.55.

EXAMPLE 38

2-Acetyl-p-anisidine (38)

Method T. To a ice-cooled solution of p-anisidine (40 g, 325 mmol) in anhydrous 1,2-dichloroethane (160 mL) in a 2000-mL round bottom flask was added slowly boron trichloride (1.0 M in $CH_2Cl_2$, 360 mL, 357 mmol). After stirring at 0° C. for 20 min, anhydrous acetonitrile (168 mL) was added, and the reaction mixture was heated to 80° C. overnight. $CH_2Cl_2$ was collected during heating via a Dean-Stark apparatus. Upon cooling to 0° C., 2N HCl (300 ml) was added and the mixture was heated at 80° C. for 30 min with stirring until a homogeneous solution was obtained. Upon cooling to rt, the reaction mixture was neutralized slowly with solid $NaHCO_3$ and extracted with $CH_2Cl_2$ (3×). The organic layer was washed with water, dried ($Na_2SO_4$) and concentrated. The crude residue was purified by silica gel chromatography to give pure product as a dark oil, which solidified upon standing at rt for a few days. Yield: 12 g (22%). $^1$H NMR (300 MHz, CDCl$_3$) δ 2.57 (s, 3H), 3.78 (s, 3H), 5.96 (br s, 2H), 6.63 (d, J=8.9 Hz, 2H), 6.97 (dd, J=8.9 Hz, 2.9 Hz, 1H), 7.18 (d, J=2.9 Hz, 1H); MS (ESI) m/z 166 ([M+H]$^+$).

EXAMPLE 39

Method U. A typical procedure is described for the synthesis of 2-acetyl-6-chloro-p-anisidine (39a). To a solution of 2-acetyl-p-anisidine (38) (1.165 g, 7.05 mmol) in acetonitrile (10 mL) at 55° C. under nitrogen was added a solution of N-chlorosuccinimide (0.942 g, 7.05 mmol, 1 equiv.) in acetonitrile (7 mL) dropwise to via an addition funnel. After the addition was complete, the reaction mixture was stirred at 55° C. for an additional 2 h. Upon cooling to rt, solvent was removed under reduced pressure. Water and aq. $NaHCO_3$ were added and the mixture was extracted with EtOAc. The organic layer was washed with brine, dried ($Na_2SO_4$), filtered and concentrated to give a crude solid, which was purified by silica gel chromatography to give pure product as yellow needles. Yield: 0.351 g (25%).

EXAMPLE 39a

2-Acetyl-6-chloro-p-anisidine (39a)

This compound was prepared according to method U. Yellow needles; Yield: 25%; mp 88-89° C.; $^1$H-NMR (300 MHz, CDCl$_3$) δ 2.59 (s, 3H), 3.78 (s, 3H), 6.43 (br s, 2H), 7.15 (d, J=2.8 Hz, 1H), 7.21 (d, J=2.8 Hz, 1H); MS (ESI) m/z 200/202 ([M+H]$^+$); Anal. Calcd for $C_9H_{10}ClNO_2$: C, 54.15; H, 5.05; N, 7.02. Found: C, 54.50; H, 5.00; N, 6.94.

EXAMPLE 39b

2-Acetyl-6-bromo-p-anisidine (39b)

This compound was prepared from 38 based on method U using NBS at rt. Yellow needles; Yield: 81%; mp 93-94° C.; $^1$H-NMR (300 MHz, CDCl$_3$) δ 2.59 (s, 3H), 3.78 (s, 3H), 6.49 (br s, 2H), 7.26 (d, J=2.8 Hz, 1H), 7.31 (d, J=2.8 Hz, 1H); MS (ESI) m/z 244/246 ([M+H]$^+$); Anal. Calcd for $C_9H_{10}BrNO_2$: C, 44.29; H, 4.13; N, 5.74. Found: C, 44.47; H, 4.11; N, 5.63.

EXAMPLE 40

Method V. A typical procedure is described for the synthesis of (2E)-1-(2-amino-3-chloro-5-methoxyphenyl)-3-(3-fluoro-4-methoxyphenyl)prop-2-en-1-one (40a). To a mixture of 2-acetyl-6-chloro-p-anisidine (39a) (1.074 g, 5.38 mmol) and 3-fluoro-4-methoxybenzaldehyde (829 mg, 5.38 mmol) in EtOH (10 mL) were added a NaOH pellet and a several drops of water. The reaction mixture was stirred at 45° C. overnight during which time orange precipitate formed. Upon cooling to rt, water was added to the reaction mixture and the precipitate was collected by filtration, washed with 10% EtOH/water, and dried in vacuo. Yield: 1.741 g (96%).

EXAMPLE 40a

(2E)-1-(2-Amino-3-chloro-5-methoxyphenyl)-3-(3-fluoro-4-methoxyphenyl)prop-2-en-1-one (40a)

This compound was prepared according to method V. Orange solid; Yield: 96%; mp 144-145° C.; $^1$H-NMR (300 MHz, CDCl$_3$) δ 3.81 (s, 3H), 3.94 (s, 3H), 6.39 (br s, 2H), 6.98 (dd, J=8.5, 8.5 Hz, 1H), 7.16 (d, J=2.8 Hz, 1H), 7.31 (d, J=2.8 Hz, 1H), 7.33 (d, J=8.6 Hz, 1H), 7.37 (d, J=15.4 Hz, 1H), 7.39 (dd, J=12.0, 2.0 Hz, 1H), 7.67 (d, J=15.4 Hz, 1H); MS (ESI) m/z 336/338 ([M+H]$^+$); Anal. Calcd for $C_{17}H_{15}ClFNO_3$: C, 60.81; H, 4.50; N, 4.17. Found: C, 60.93; H, 4.68; N, 4.07.

EXAMPLE 40b

(2E)-1-(2-Amino-3-bromo-5-methoxyphenyl)-3-(3-fluoro-4-methoxyphenyl)prop-2-en-1-one (40b)

This compound was prepared from 39b according to method V. Orange solid; Yield: 97%; mp 123-125° C.; $^1$H NMR (400 MHz, DMSO-d6) δ 3.79 (s, 3H), 3.90 (s, 3H), 6.89 (br s, 2H), 7.23 (t, J=8.8 Hz, 1H), 7.45 (d, J=2.8 Hz, 1H), 7.62-7.67 (m, 2H), 7.70 (d, J=2.8 Hz, 1H), 7.86 (d, J=15.4 Hz, 1H), 7.97 (dd, J=12.9, 2.0 Hz, 1H); MS (ESI) m/z 380/382 ([M+H]$^+$); Anal. Calcd for $C_{17}H_{15}BrFNO_3$: C, 53.70; H, 3.98; N, 3.68. Found: C, 53.38; H, 3.81; N, 3.65.

EXAMPLE 41

Method W. A typical procedure is described for the synthesis of 8-chloro-2-(3-fluoro-4-methoxyphenyl)-6-methoxyquinolin-4-ol (41a). A mixture of (2E)-1-(2-amino-3-chloro-5-methoxyphenyl)-3-(3-fluoro-4-methoxyphenyl)prop-2-en-1-one (40a) (1.712 g, 5.10 mmol), acetic acid (15 mL) and phosphoric acid (85%, 4 mL) was stirred under reflux until all starting material and reaction intermediates were completely converted to the desired product (3-4 d). Upon cooling to rt, water was added to the reaction mixture and the gray precipitate formed was collected by filtration, washed with aq. $NaHCO_3$ and water, and dried in vacuo. Yield: 1.66 g (97%).

EXAMPLE 41a

8-Chloro-2-(3-fluoro-4-methoxyphenyl)-6-methoxyquinolin-4-ol (41a)

This compound was prepared according to method W. Gray solid; Yield: 97%; mp 233-234° C.; $^1$H-NMR (400 MHz, DMSO-d6) δ 3.90 (s, 3H), 3.93 (s, 3H), 7.33 (dd, J=8.8, 8.7 Hz, 1H), 7.38 (s, 1H), 7.42 (d, J=2.4 Hz, 1H), 7.59 (d, J=2.5 Hz, 1H), 7.91 (d, J=8.5 Hz, 1H), 8.02 (d, J=13.1 Hz, 1H), 11.65 (s, 1H); $^{19}$F-NMR (400 MHz, DMSO-d6) δ −135.46 (dd, J=12.9, 9.2 Hz); MS (ESI) m/z 332/334 ([M−H]$^-$), 334/336 ([I+H]$^+$); Anal. Calcd for $C_{17}H_{13}ClFNO_3$: C, 61.18; H, 3.93; N, 4.20. Found: C, 60.97; H, 3.73; N, 3.96.

EXAMPLE 41b

8-Bromo-2-(3-fluoro-4-methoxyphenyl)-6-methoxyquinolin-4-ol (41b)

This compound was prepared from 40b according to method W. Off-white solid; Yield: 91%; mp 200-201° C.; $^1$H-NMR (400 MHz, DMSO-d6) δ 3.90 (s, 3H), 3.93 (s, 3H), 7.33 (dd, J=8.8, 8.7 Hz, 1H), 7.38 (s, 1H), 7.46 (d, J=2.3 Hz, 1H), 7.77 (d, J=2.4 Hz, 1H), 7.92 (d, J=8.6 Hz, 1H), 8.04 (d, J=13.2 Hz, 1H), 11.66 (s, 1H); MS (ESI) m/z 376/378 ([M−H]$^-$), 378/380 ([M+H]$^+$); Anal. Calcd for $C_{17}H_{13}BrFNO_3$: C, 53.99; H, 3.46; N, 3.70. Found: C, 54.13; H, 3.30; N, 3.66.

EXAMPLE 42

8-Bromo-4-chloro-2-(3-fluoro-4-methoxyphenyl)-6-methoxyquinoline (42)

This compound was prepared from 41b according to method C. White solid; Yield: 38%; $^1$H-NMR (400 MHz, DMSO-d6) δ 3.94 (s, 3H), 3.98 (s, 3H), 7.35 (t, J=8.9 Hz, 1H), 7.48 (d, J=2.7 Hz, 1H), 7.96 (d, J=2.7 Hz, 1H), 8.19-8.25 (m, 2H), 8.50 (s, 1H); MS (ESI) m/z 396/398/400 ([M+H]$^+$); Anal. Calcd for $C_{17}H_{12}BrClFNO_2$: C, 51.48; H, 3.05; N, 3.53. Found: C, 52.34; H, 3.24; N, 3.27.

EXAMPLE 43a

4-Bromo-8-chloro-2-(3-fluoro-4-methoxyphenyl)-6-methoxyquinoline (43a)

This compound was prepared from 41a according to method D. White powder; Yield: 86%; mp 156-157° C.; $^1$H-NMR (400 MHz, CDCl$_3$) δ 3.97 (s, 3H), 3.98 (s, 3H), 7.07 (dd, J=8.6, 8.6 Hz, 1H), 7.35 (d, J=2.7 Hz, 1H), 7.56 (d, J=2.7 Hz, 1H), 7.91 (ddd, J=8.6, 1.1, 1.0 Hz, 1H), 8.04 (dd, J=12.7, 2.1 Hz, 1H), 8.12 (s, 1H); $^{19}$F-NMR (400 MHz, CDCl$_3$) δ −134.87 (dd, J=13.2, 10.0 Hz); MS (ESI) m/z 396/398/400 ([M+H]$^+$); Anal. Calcd for $C_{17}H_{12}BrClFNO_2$: C, 51.48; H, 3.05; N, 3.53. Found: C, 51.44; H, 2.85; N, 3.36.

EXAMPLE 43b

4,8-Dibromo-2-(3-fluoro-4-methoxyphenyl)-6-methoxyquinoline (43b)

This compound was prepared from compound 41b according to method D. Tan solid; yield: 60%; mp 178-179° C.; $^1$H NMR (400 MHz, DMSO-d6) δ 3.94 (s, 3H), 3.98 (s, 3H), 7.34 (t, J=8.9 Hz, 1H), 7.43 (d, J=2.7 Hz, 1H), 7.95 (d, J=2.7 Hz, 1H), 8.19-8.25 (m, 2H), 8.63 (s, 1H); $^{19}$F NMR (400 MHz, DMSO-d6) δ −135.21 (dd, J=12.3, 8.8 Hz); MS (EI) m/z 440/442/444 ([M+H]$^+$); Anal. Calcd for $C_{17}H_{12}Br_2FNO_2$: C, 46.29; H, 2.74; N, 3.18. Found: C, 46.31; H, 2.70; N, 3.09.

EXAMPLE 44

8-Bromo-4-chloro-2-(3-fluoro-4-hydroxyphenyl)-quinolin-6-ol (44)

This compound was prepared from 42 according to method E. Yellow solid; Yield: 45%; mp>210° C. (dec.); $^1$H-NMR (400 MHz, DMSO-d6) δ 7.09 (t, J=8.8 Hz, 1H), 7.40 (d, J=2.6 Hz, 1H), 7.78 (d, J=2.6 Hz, 1H), 8.03 (dd, J=8.5, 1.7 Hz, 1H), 8.15 (dd, J=12.9, 2.2 Hz, 1H), 8.35 (s, 1H), 10.38 (s, 1H), 10.69 (s, 1H); MS (ESI) m/z 366/368/370 ([M−H]$^-$), 368/370/372 ([M+H]$^+$); Anal. Calcd for $C_{15}H_8BrClFNO_2$: C, 48.88; H, 2.19; N, 3.80. Found: C, 47.03; H, 2.18; N, 3.58.

EXAMPLE 45a

4-Bromo-8-chloro-2-(3-fluoro-4-hydroxyphenyl)quinolin-6-ol (45a)

This compound was prepared from 43a according to method E. White solid; Yield: 99%; mp 184-186° C.; $^1$H-NMR (400 MHz, DMSO-d6) δ 7.10 (dd, J=8.8, 8.8 Hz, 1H), 7.36 (d, J=2.6 Hz, 1H), 7.59 (d, J=2.6 Hz, 1H), 8.00 (m, 1H), 8.13 (dd, J=12.9, 2.2 Hz, 1H), 8.50 (s, 1H), 10.38 (s, 1H), 10.71 (s, 1H); $^{19}$F-NMR (400 MHz, DMSO-d6) δ −136.28 (dd, J=12.8, 9.2 Hz); MS (ESI) m/z 366/368/370 ([M−H]$^-$), 368/370/372 ([M+H]$^+$); Anal. Calcd for $C_{15}H_8BrClFNO_2$: C, 48.88; H, 2.19 N, 3.80. Found: C, 48.71; H, 2.21; N, 3.73.

EXAMPLE 45b

4,8-Dibromo-2-(3-fluoro-4-hydroxyphenyl)quinolin-6-ol (45b)

This compound was prepared from 43b according to method E. Brown solid; Yield: 75%; mp 180° C. (dec.); $^1$H NMR (400 MHz, DMSO-d6) δ 7.09 (t, J=8.8 Hz, 1H), 7.39 (d, J=2.6 Hz, 1H), 7.76 (d, J=2.6 Hz, 1H), 8.02 (dd, J=8.5, 1.6 Hz, 1H), 8.14 (dd, J=12.9, 2.1 Hz, 1H), 8.50 (s, 1H), 10.37 (s, 1H), 10.69 (s, 1H); $^{19}$F NMR (400 MHz, DMSO-d6) δ −136.22 (dd, J=12.7 Hz, 9.2 Hz); MS (EI) m/z 410/412/414 ([M−H]$^-$), 412/414/416 ([M+H]$^+$); Anal. Calcd for $C_{15}H_8Br_2FNO_2$: C, 43.62; H, 1.95; N, 3.39. Found: C, 43.45; H, 2.34; N, 3.07.

EXAMPLE 46

Method X. A typical procedure is described for the synthesis of 8-chloro-4-cyano-2-(3-fluoro-4-methoxyphenyl)-6-methoxyquinoline (46). A mixture of 4-bromo-8-chloro-2-(3-fluoro-4-methoxyphenyl)-6-methoxyquinoline (43a) (1.556 g, 3.923 mmol), Zn(CN)$_2$ (470 mg, 4.00 mmol, 1.02 equiv.), tris(dibenzylideneacetone)dipalladium [Pd$_2$(dba)$_3$] (180 mg, 0.197 mmol, 5 mol %), 1,1'-bis(diphenylphosphino)ferrocene (dppf) (218 mg, 0.392 mmol, 10 mol %), Zn dust (64 mg, 0.979 mmol, 25 mol %) in anhydrous DMF (15 mL) was heated at 85° C. under nitrogen until all starting material was consumed (1 h). After cooling to rt, water and NH$_4$OH (2N, 10 mL) were added and the mixture was extracted with (warm) CHCl$_3$ (2-3×). The organic layer was washed with water, brine, dried (Na$_2$SO$_4$), filtered through a short pad of silica gel, and concentrated to give a crude yellow solid, which was recrystallized (hot CHCl$_3$/−20° C.) to give pure product as a yellow needles. Yield: 1.295 g (96%).

8-Chloro-4-cyano-2-(3-fluoro-4-methoxyphenyl)-6-methoxyquinoline (46)

This compound was prepared according to method X. Yellow needles; Yield: 96%; mp 227-228° C.; $^1$H-NMR (400 MHz, CDCl$_3$) δ 3.98 (s, 3H), 4.01 (s, 3H), 7.10 (dd, J=8.7, 8.5 Hz, 1H), 7.30 (d, J=2.6 Hz, 1H), 7.63 (d, J=2.6 Hz, 1H), 7.91 (ddd, J=8.6, 1.6, 1.3 Hz, 1H), 8.07 (dd, J=12.6, 2.2 Hz, 1H), 8.14 (s, 1H); $^{19}$F-NMR (400 MHz, CDCl$_3$) δ −134.34 (dd, J=12.5, 8.3 Hz); MS (ESI) m/z 343/345 ([M+H]$^+$); Anal. Calcd for C$_{18}$H$_{12}$ClFN$_2$O$_2$: C, 63.08; H, 3.53; N, 8.17. Found: C, 63.22; H, 3.43; N, 7.89.

EXAMPLE 47

8-Chloro-4-cyano-2-(3-fluoro-4-hydroxyphenyl)quinolin-6-ol (47)

This compound was prepared from 46 according to method E. Yellow powder; Yield: 72%; mp 315° C. (dec.); $^1$H-NMR (400 MHz, DMSO-d6) δ 7.12 (dd, J=8.8, 8.8 Hz, 1H), 7.29 (d, J=2.5 Hz, 1H), 7.66 (d, J=2.5 Hz, 1H), 8.03 (dd, J=8.5, 1.7 Hz, 1H), 8.13 (dd, J=12.8, 2.1 Hz, 1H), 8.74 (s, 1H), 10.45 (s, 1H), 10.97 (s, 1H); $^{19}$F-NMR (400 MHz, DMSO-d6) δ −136.09 (dd, J=13.1, 9.1 Hz); MS (ESI) m/z 313/315 ([M−H]$^-$), 315/317 ([M+H]$^+$); Anal. Calcd for C$_{16}$H$_8$ClFN$_2$O$_2$: C, 61.07; H, 2.56; N, 8.90. Found: C, 61.01; H, 2.48; N, 8.67.

EXAMPLE 48

8-Chloro-4-ethynyl-2-(3-fluoro-4-hydroxyphenyl)quinolin-6-ol (48)

This compound was prepared from 45a following a combination of method J using (trimethylsilylethynyl)tributyltin and method L. Yellow solid; Yield: 73%; mp 210° C. (dec.); $^1$H-NMR (400 MHz, DMSO-d6) δ 5.06 (s, 1H), 7.09 (dd, J=8.9, 8.8 Hz, 1H), 7.45 (d, J=2.6 Hz, 1H), 7.56 (d, J=2.6 Hz, 1H), 8.00 (dd, J=8.5, 1.7 Hz, 1H), 8.12 (dd, J=12.9, 2.2 Hz, 1H), 8.26 (s, 1H), 10.34 (s, 1H), 10.60 (s, 1H); $^{19}$F-NMR (400 MHz, DMSO-d6) δ −136.30 (dd, J=13.2, 9.3 Hz); MS (ESI) m/z 312/314 ([M−H]$^-$), 314/316 ([M+H]$^+$); Anal. Calcd for C$_{17}$H$_9$ClFNO$_2$: C, 65.09; H, 2.89; N, 4.46. Found: C, 64.86; H, 3.14; N, 4.05.

EXAMPLE 49

8-Chloro-2-(3-fluoro-4-hydroxyphenyl)-4-hex-1-ynylquinolin-6-ol (49)

Method Y. A mixture of 4-bromo-8-chloro-2-(3-fluoro-4-hydroxyphenyl)quinolin-6-ol (45a) (30 mg, 0.0814 mmol), Pd(PPh$_3$)$_2$Cl$_2$ (3 mg, 0.0042 mmol, 5 mol %), CuI (1.6 mg, 0.0084 mmol, 10 mol %), 1-hexyne (13 mg, 0.158 mmol, 2 equiv.), Et$_3$N (12 mg, 0.119 mmol, 1.5 equiv.) in anhydrous DMF (0.5 mL) was stirred at rt for 2 h and then at 40° C. for an additional 2 h under nitrogen until all starting material was consumed. The reaction mixture was diluted with water and extracted with EtOAc. The organic layer was washed with water, brine, dried (Na$_2$SO$_4$), filtered and concentrated to give a crude product, which was passed through a short pad of silica gel to give pure product as a brown solid. Yield: 27 mg (90%); mp 172-173° C.; $^1$H-NMR (400 MHz, DMSO-d6) δ 0.97 (t, J=7.3 Hz, 3H), 1.53 (hex, J=7.4 Hz, 2H), 1.67 (p, J=7.4 Hz, 2H), 2.65 (t, J=7.1 Hz, 2H), 7.08 (dd, J=8.9, 8.7 Hz, 1H), 7.42 (d, J=2.6 Hz, 1H), 7.53 (d, J=2.6 Hz, 1H), 7.99 (dd, J=8.5, 1.7 Hz, 1H), 8.11 (dd, J=13.1, 2.2 Hz, 1H), 8.13 (s, 1H), 10.43 (br s, 2H); $^{19}$F-NMR (400 MHz, DMSO-d6) δ −136.37 (dd, J=12.9, 9.2 Hz); MS (ESI) m/z 368/370 ([M−H]$^-$), 370/372 ([M+H]$^+$); Anal. Calcd for C$_{21}$H$_{17}$ClFNO$_2$: C, 68.20; H, 4.63; N, 3.79. Found: C, 65.08; H, 4.83; N, 3.28.

EXAMPLE 50

8-Chloro-2-(3-fluoro-4-hydroxyphenyl)-4-vinylquinolin-6-ol (50)

This compound was prepared from 45a based on method J using 1.1 equiv. of tributyl(vinyl)tin at 90° C. Red solid; Yield: 84%; mp 225° C. (dec.); $^1$H-NMR (400 MHz, DMSO-d6) δ 5.74 (dd, J=11.1, 1.0 Hz, 1H), 6.30 (dd, J=17.3, 1.1 Hz, 1H), 7.10 (dd, J=8.8, 8.8 Hz, 1H), 7.35 (d, J=2.6 Hz, 1H), 7.38 (dd, J=17.3, 11.1 Hz, 1H), 7.53 (d, J=2.5 Hz, 1H), 8.04 (dd, J=8.4, 1.7 Hz, 1H), 8.16 (dd, J=13.1, 2.1 Hz, 1H), 8.16 (s, 1H), 10.27 (s, 1H), 10.35 (s, 1H); $^{19}$F-NMR (400 MHz, DMSO-d6) δ −136.51 (dd, J=13.2, 9.3 Hz); MS (ESI) m/z 314/316 ([M−H]$^-$), 316/318 ([M+H]$^+$); Anal. Calcd for C$_{17}$H$_{11}$ClFNO$_2$: C, 64.67; H, 3.51; N, 4.44. Found: C, 63.57; H, 3.61; N, 4.04.

EXAMPLE 51

8-Chloro-4-(4-cyanophenyl)-2-(3-fluoro-4-hydroxyphenyl)quinolin-6-ol (51)

This compound was prepared from 45a using 4-cyanophenylboronic acid according to method P. Yellow solid; Yield: 94%; mp 324° C. (dec.); $^1$H-NMR (400 MHz, DMSO-d6) δ 6.93 (d, J=2.5 Hz, 1H), 7.09 (dd, J=8.8, 8.8 Hz, 1H), 7.54 (d, J=2.6 Hz, 1H), 7.81 (d, J=8.4 Hz, 2H), 8.03 (s, 1H), 8.04 (dd, J=8.5, 1.6 Hz, 1H), 8.09 (d, J=8.4 Hz, 2H), 8.17 (dd, J=12.9, 2.1 Hz, 1H), 10.32 (s, 2H); $^{19}$F-NMR (400 MHz, DMSO-d6) δ −136.43 (dd, J=13.0, 9.7 Hz); MS (ESI) m/z 389/391 ([M−H]$^-$), 391/393 ([M+H]$^+$); Anal. Calcd for C$_{22}$H$_{12}$ClFN$_2$O$_2$: C, 67.62; H, 3.09; N, 7.17. Found: C, 67.00; H, 3.74; N, 6.64.

EXAMPLE 52

8-Chloro-2-(3-fluoro-4-hydroxyphenyl)-4-(4-methoxyphenyl)quinolin-6-ol (52)

This compound was prepared from 45a using 4-methoxyphenylboronic acid according to method P. Orange solid; Yield: 97%; mp 140-142° C.; $^1$H-NMR (400 MHz, DMSO-d6) δ 3.87 (s, 3H), 7.09 (dd, J=8.8, 8.8 Hz, 1H), 7.11 (d, J=2.7 Hz, 1H), 7.16 (d, J=8.8 Hz, 2H), 7.51 (d, J=2.6 Hz, 1H), 7.53 (d, J=8.8 Hz, 2H), 7.93 (s, 1H), 8.02 (dd, J=8.5, 1.7 Hz, 1H), 8.14 (dd, J=13.1, 2.1 Hz, 1H), 10.21 (s, 1H), 10.27 (s, 1H); $^{19}$F-NMR (400 MHz, DMSO-d6) δ −136.48 (dd, J=13.0, 9.7 Hz); MS (ESI) m/z 394/396 ([M−H]$^-$), 396/398 ([M+H]$^+$); Anal. Calcd for C$_{22}$H$_{15}$ClFNO$_3$: C, 66.76; H, 3.82; N, 3.54. Found: C, 66.05; H, 4.01; N, 3.19.

EXAMPLE 53

8-Cyano-2-(3-fluoro-4-methoxyphenyl)-6-methoxyquinolin-4-ol (53)

This compound was prepared from 41b according to method X. White solid; Yield: 85%; mp 218-220° C.; $^1$H NMR (400 MHz, DMSO-d6) δ 3.93 (s, 3H), 3.94 (s, 3H), 7.36 (t, J=8.8 Hz, 1H), 7.42 (s, 1H), 7.72 (d, J=2.8 Hz, 1H), 7.95 (d, J=8.7 Hz, 1H), 8.02 (d, J=2.9 Hz, 1H), 8.03 (dd, J=13.1, 2.1

Hz, 1H), 11.93 (s, 1H); MS (ESI) m/z 325 ([M+H]$^+$); Anal. Calcd for $C_{18}H_{13}FN_2O_2$: C, 66.66; H, 4.04; N, 8.64. Found: C, 66.51; H, 4.34; N, 7.69.

EXAMPLE 54

4-Chloro-8-cyano-2-(3-fluoro-4-methoxyphenyl)-6-methoxyquinoline (54)

This compound was prepared from 53 according to method C. Brown solid; Yield: 95%; mp 220° C. (dec.); $^1$H NMR (400 MHz, DMSO-d6) δ 3.95 (s, 3H), 4.02 (s, 3H), 7.38 (t, J=8.7 Hz, 1H), 7.71 (d, J=2.8 Hz, 1H), 8.20-8.24 (m, 3H), 8.57 (s, 1H); MS (ESI) m/z 343/345 ([M+H]$^+$); Anal. Calcd for $C_{18}H_{12}ClFN_2O_2$: C, 63.08; H, 3.53; N, 8.17. Found: C, 61.28; H, 3.51; N, 7.30.

EXAMPLE 55

4-Bromo-8-cyano-2-(3-fluoro-4-methoxyphenyl)-6-methoxyquinoline (55)

This compound was prepared from 53 according to method D. Yellow solid; Yield: 48%; $^1$H NMR (400 MHz, DMSO-d6) δ 3.95 (s, 3H), 4.02 (s, 3H), 7.38 (t, J=8.7 Hz, 1H), 7.67 (d, J=2.8 Hz, 1H), 8.21-8.25 (m, 3H), 8.73 (s, 1H); $^{19}$F NMR (400 MHz, DMSO-d$_6$) δ −135.11 (dd, J=12.1 Hz, 9.2 Hz); MS (ESI) m/z 387/389 ([M+H]$^+$).

EXAMPLE 56

4-Chloro-8-cyano-2-(3-fluoro-4-hydroxyphenyl)quinolin-6-ol (56)

This compound was prepared from 54 according to method E. Tan solid; Yield: 82%; mp 296-298° C.; $^1$H NMR (400 MHz, DMSO-d6) δ 7.12 (t, J=8.8 Hz, 1H), 7.66 (d, J=2.6 Hz, 1H), 7.94 (d, J=2.7 Hz, 1H), 8.04 (dd, J=8.5, 1.7 Hz, 1H), 8.14 (dd, J=12.8, 2.1 Hz, 1H), 8.44 (s, 1H), 10.48 (s, 1H), 10.97 (s, 1H); MS (ESI) m/z 313/315 ([M−H]$^−$), 315/317 ([M+H]$^+$); Anal. Calcd for $C_{16}H_8ClFN_2O_2$: C, 61.07; H, 2.56; N, 8.90. Found: C, 60.69; H, 2.82; N, 8.47.

EXAMPLE 57

4-Bromo-8-cyano-2-(3-fluoro-4-hydroxyphenyl)quinolin-6-ol (57)

This compound was prepared from 55 according to method E. Yellow solid; Yield: 54%; mp>290° C. (dec.); $^1$H NMR (400 MHz, DMSO-d6) δ 7.12 (t, J=8.8 Hz, 1H), 7.65 (d, J=2.7 Hz, 1H), 7.93 (d, J=2.7 Hz, 1H), 8.04 (dd, J=7.9, 2.0 Hz, 1H), 8.15 (dd, J=12.8, 2.2 Hz, 1H), 8.60 (s, 1H), 10.47 (s, 1H) 10.97 (s, 1H); $^{19}$F NMR (400 MHz, DMSO-d6) δ −136.10 (dd, J=12.9, 8.8 Hz); MS (ESI) m/z 359/361 ([M+H]$^+$); Anal. Calcd for $C_{16}H_8BrFN_2O_2$: C, 53.51; H, 2.25; N, 7.80. Found: C, 54.84; H, 2.65; N, 7.04.

EXAMPLE 58

8-Cyano-4-ethynyl-2-(3-fluoro-4-hydroxyphenyl)quinolin-6-ol (58)

This compound was prepared from 56 following a combination of method J using (trimethylsilylethynyl)tributyltin and method L. Yellow solid; Yield: 48%; mp>270° C. (dec.); $^1$H NMR (400 MHz, DMSO-d6) δ 5.14 (s, 1H), 7.11 (t, J=8.8 Hz, 1H), 7.73 (d, J=2.7 Hz, 1H), 7.91 (d, J=2.7 Hz, 1H), 8.04 (dd, J=8.5, 1.7 Hz, 1H), 8.14 (dd, J=12.9, 2.1 Hz, 1H), 8.35 (s, 1H), 10.44 (s, 1H), 10.87 (s, 1H); MS (ESI) m/z 303 ([M−H]$^−$), 305 ([M+H]$^+$).

EXAMPLE 59

8-(4-Cyanophenyl)-2-(3-fluoro-4-methoxyphenyl)-6-methoxyquinolin-4-ol (59)

This compound was prepared from 41b using 4-cyanophenylboronic acid according to method P. Orange solid; Yield: 56%; mp 248-250° C.; $^1$H NMR (300 MHz, DMSO-d6) δ 3.89 (s, 3H), 3.94 (s, 3H), 7.28 (t, J=8.8 Hz, 1H), 7.36 (s, 1H), 7.44 (d, J=2.9 Hz, 1H), 7.53 (d, J=2.9 Hz, 1H), 7.75-7.79 (m, 2H), 7.97 (br s, 4H), 11.50 (s, 1H); MS (ESI) m/z 401 ([M+H]$^+$). Anal. Calcd for $C_{24}H_{17}FN_2O_3$: C, 71.99; H, 4.28; N, 7.00. Found: C, 71.55; H, 4.47; N, 6.60.

EXAMPLE 60

4-Chloro-8-(4-cyanophenyl)-2-(3-fluoro-4-methoxyphenyl)-6-methoxyquinoline (60)

This compound was prepared from 59 according to method C. White solid; Yield: 48%; mp 278-280° C.; $^1$H NMR (400 MHz, DMSO-d6) δ 3.90 (s, 3H), 4.02 (s, 3H), 7.30 (t, J=8.8 Hz, 1H), 7.55 (d, J=2.8 Hz, 1H), 7.62 (d, J=2.7 Hz, 1H), 7.95-8.02 (m, 6H), 8.46 (s, 1H); MS (ESI) m/z 419/421 ([M+H]$^+$). Anal. Calcd for $C_{24}H_{16}ClFN_2O_2$: C, 68.82; H, 3.85; N, 6.69. Found: C, 63.57; H, 3.38; N, 6.02.

EXAMPLE 61

4-Chloro-8-(4-cyanophenyl)-2-(3-fluoro-4-hydroxyphenyl)quinolin-6-ol (61)

This compound was prepared from 60 according to method E. Brown solid; Yield: 51%; mp>300° C. (dec.); $^1$H NMR (400 MHz, DMSO-d6) δ 7.03 (t, J=8.8 Hz, 1H), 7.46 (d, J=2.6 Hz, 1H), 7.48 (d, J=2.7 Hz, 1H), 7.79 (dd, J=8.5, 1.7 Hz, 1H), 7.88 (dd, J=13.0, 2.0 Hz, 1H), 7.93 (d, J=8.6 Hz, 2H), 8.00 (d, J=8.5 Hz, 2H), 8.31 (s, 1H), 10.31 (s, 1H) 10.58 (s, 1H); MS (ESI) m/z 389/391 ([M−H]$^−$), 391/393 ([M+H]$^+$); Anal. Calcd for $C_{22}H_{12}ClFN_2O_2$: C, 67.62; H, 3.09; N, 7.17. Found: C, 63.89; H, 2.87; N, 6.75.

EXAMPLE 62

Representative examples of the invention were evaluated for their ability to compete with 17β-estradiol for both ERα and ERβ. This test procedure provides the methodology for one to determine whether a particular compound binds to the estrogen receptor (and is therefore "estrogenic") and whether there is selectivity for ERα or ERβ. The values are shown in the Table infra and are reported as IC$_{50}$s. 17β-estradiol is included as a standard reference for compalison. The procedure used is briefly described below. A crude lysate of E. coli expressing the estrogen receptor ligand binding domains (D, E, & F) of human ERα or ERβ was prepared. Both receptors and compounds were diluted in 1× Dulbecco's PBS (DPBS) supplemented with 1 mM EDTA. Using a high binding masked microtiter plate, 100 uL of receptor (1 uG/well) was combined with 2 nM [$^3$H]-17β-estradiol and various concentrations of compound. After between 5 and 15 hours at room temperature, the plates were washed with DPBS/1 mM EDTA and bound radioactivity determined by liquid scintillation counting. The IC$_{50}$ is defined as the concentration of compound that decreases total 17β-estradiol binding by 50%. The results obtained are described in the Table 1 below.

TABLE 1

Binding affinities and receptor selectivity of representative compounds of the invention.

| Cpd | P | R¹ | R² | R³ | R⁴ | R⁵ | R⁶ | ERβ IC$_{50}$ (nM) | ERα IC$_{50}$ (nM) | α/β |
|---|---|---|---|---|---|---|---|---|---|---|
| 5a | H | H | H | H | Cl | H | H | 4.6 | 213 | 46 |
| 5b | H | F | H | H | Cl | H | H | 5.3 | 246 | 46 |
| 6a | H | H | H | H | Br | H | H | 4.3 | 212 | 50 |
| 6b | H | F | H | H | Br | H | H | 3.4 | 283 | 83 |
| 6c | H | F | F | H | Br | H | H | 42 | 976 | 23 |
| 7 | Ac | F | H | H | Br | H | H | 198 | >5000 | >25 |
| 8a | H | H | H | H | I | H | H | 2.4 | 103 | 43 |
| 8b | H | F | H | H | I | H | H | 5 | 365 | 73 |
| 10a | H | H | H | H | CN | H | H | 28 | 455 | 16 |
| 10b | H | F | H | H | CN | H | H | 23 | 1047 | 46 |
| 11a | H | H | H | H | CH=CH$_2$ | H | H | 60 | 504 | 8 |
| 11b | H | F | H | H | CH=CH$_2$ | H | H | 37 | 458 | 12 |
| 12a | H | H | H | H | Et | H | H | 61 | 837 | 14 |
| 12b | H | F | H | H | Et | H | H | 40 | 1030 | 26 |
| 13a | H | H | H | H | C≡C—TMS | H | H | 161 | 1510 | 9 |
| 13b | H | F | H | H | C≡C—TMS | H | H | 153 | 1690 | 11 |
| 14a | H | H | H | H | C≡CH | H | H | 76 | 1500 | 20 |
| 14b | H | F | H | H | C≡CH | H | H | 32 | 3413 | 106 |
| 14c | H | F | F | H | C≡CH | H | H | 750 | 4820 | 6 |
| 15 | H | F | H | H | C≡C—Ph | H | H | 195 | 12000 | 62 |
| 16a | H | H | H | H | COMe | H | H | 211 | 2937 | 14 |
| 16b | H | F | H | H | COMe | H | H | 93 | 3370 | 36 |
| 17a | H | H | H | H | CH(OH)Me | H | H | >5000 | >5000 | ND |
| 17b | H | F | H | H | CH(OH)Me | H | H | >5000 | >5000 | ND |
| 19 | H | H | H | H | OMe | H | H | 1190 | 6630 | 6 |
| 20 | H | F | H | H | Ph | H | H | 128 | 1378 | 11 |
| 21 | H | F | H | H | p-tolyl | H | H | 112 | 2920 | 26 |
| 22 | H | F | H | H | 4-F—Ph | H | H | 33 | 591 | 18 |
| 23 | H | F | H | H | 4-Cl—Ph | H | H | 146 | >1000 | >6 |
| 24 | H | F | H | H | 4-NC—Ph | H | H | 53 | 1810 | 34 |
| 25 | H | F | H | H | 4-CF$_3$—Ph | H | H | >5000 | >5000 | ND |
| 26 | H | F | H | H | 3-thienyl | H | H | 75 | 868 | 12 |
| 18 | H | F | H | H | 2-thiazolyl | H | H | 208 | 2160 | 10 |
| 27 | H | F | H | H | 4-pyridinyl | H | H | 78 | >1000 | >12 |
| 28 | H | F | H | H | 5-pyrimidinyl | H | H | 968 | 3310 | 3 |
| 31 | H | H | H | H | H | Cl | H | 38 | 840 | 22 |
| 32 | H | H | H | H | H | Br | H | 90 | 1190 | 13 |
| 35a | H | H | H | Cl | Br | H | H | 1.25 | 78 | 62 |
| 35b | H | F | H | Cl | Br | H | H | 3.7 | 90 | 24 |
| 36 | H | H | H | Cl | 4-F—Ph | H | H | 244 | 340 | 1.4 |
| 37 | H | F | H | Cl | CN | H | H | 26 | 318 | 12 |
| 45a | H | H | H | H | Br | H | Cl | 0.35 | 18.7 | 53 |
| 48 | H | F | H | H | C≡CH | H | Cl | 0.75 | 37 | 50 |
| 49 | H | F | H | H | C≡C(CH$_2$)$_3$CH$_3$ | H | Cl | 21 | 304 | 14 |
| 47 | H | F | H | H | CN | H | Cl | 1.7 | 192 | 113 |
| 50 | H | F | H | H | CH=CH$_2$ | H | Cl | 0.95 | 75 | 79 |
| 51 | H | F | H | H | 4-NC—Ph | H | Cl | 37 | 2065 | 56 |
| 52 | H | F | H | H | 4-MeO—Ph | H | Cl | 13 | 195 | 15 |
| 45b | H | F | H | H | Br | H | Br | 1.7 | 11.6 | 7 |
| 44 | H | F | H | H | Cl | H | Br | 0.54 | 31 | 57 |
| 56 | H | F | H | H | Cl | H | CN | 1.1 | 116 | 105 |
| 57 | H | F | H | H | Br | H | CN | 1.4 | 86 | 61 |
| 58 | H | F | H | H | C≡CH | H | CN | 1.3 | 87 | 67 |
| 61 | H | F | H | H | Cl | H | 4-NC—Ph | 13 | 522 | 40 |
| 62 | H | F | H | H | H | H | CN | 17 | 548 | 32 |

The results obtained in the standard pharmacologic test procedure demonstrate that the compounds of this invention are estrogenic compounds, many with strong preferential affinity for the ERβ receptor. The compounds of this invention range from having high preferential affinity for ERβ over ERα to almost equal affinity for both receptors. Thus, compounds of this invention will span a range of activity based, at least partially, on their receptor affinity selectivity profiles. Additionally, since each novel receptor ligand complex is unique and thus its interaction with various coregulatory proteins is unique, compounds of this invention will display different modulatory behavior depending on the cellular context they are in. For example, in some cell-types, it is possible for a compound to behave as an estrogen agonist while in other tissues, an antagonist. Compounds with such activity have sometimes been referred to as SERMs (Selective Estrogen Receptor Modulators). Unlike many estrogens, however, many of the SERMs do not cause increases in uterine wet weight. These compounds are antiestrogenic in the uterus and can completely antagonize the trophic effects of estrogen agonists in uterine tissue. These compounds, however, act as estrogen agonists in the bone, cardiovascular, and central nervous systems. Due to this tissue selective nature of these compounds, they are useful in treating or preventing in a mammal disease states or syndromes which are caused or associated with an estrogen deficiency (in certain tissues such as bone or cardiovascular) or an excess of estrogen (in the uterus or mammary glands).

Even beyond such cell-specific modulation, compounds of this invention also have the potential to behave as agonists on one receptor type while behaving as antagonists on the other. For example, it has been demonstrated that compounds can be an antagonist on ERβ while being an agonist on ERα (Meyers, Marvin J.; Sun, Jun; Carlson, Kathryn E.; Katzenellenbogen, Benita S.; Katzenellenbogen, John A. *J. Med. Chem.* (1999), 42(13), 2456-2468). Such ERSAA (Estrogen Receptor Selective Agonist Antagonist) activity provides for pharmacologically distinct estrogenic activity within this series of compounds.

Standard pharmacological test procedures are readily available to determine the activity profile of a given test compound. The following briefly summarizes several representative test procedures. Standard pharmacological test procedures for SERMs are also provided in U.S. Pat. Nos. 4,418,068 and 5,998,402.

EXAMPLE 63

Rat Uterotrophic/Antiuterotrophic Test Procedure

The estrogenic and antiestrogenic properties of the compounds can be determined in an immature rat uterotrophic assay (4 day) that (as described previously by L. J. Black and R. L. Goode, Life Sciences, 26, 1453 (1980). Immature Sprague-Dawley rats (female, 18 days old) were tested in groups of six. The animals are treated by daily ip injection with 10 uG compound, 100 uG compound, (100 uG compound+1 uG 17β-estradiol) to check antiestrogenicity, and 1 uG 17β-estradiol, with 50% DMSO/50% saline as the injection vehicle. On day 4 the animals are sacrificed by $CO_2$ asphyxiation and their uteri removed and stripped of excess lipid, any fluid removed and the wet weight determined. A small section of one horn is submitted for histology and the remainder used to isolate total RNA in order to evaluate complement component 3 gene expression.

EXAMPLE 64

6-Week Ovariectomized Rat Test Procedure—Bone and Cardioprotection

Female Sprague Dawley CD rats, ovx or sham ovx, are obtained 1 day after surgery from Taconic Farm (weight range 240-275 g). They are housed 3 or 4 rats/cage in a room on a 12/12 (light/dark) schedule and provided with food (Purina 5K96C rat chow) and water ad libitum. Treatment for all studies begin 1 day after the animals arrival and dosed 7 days per week as indicated for 6 weeks. A group of age matched sham operated rats not receiving any treatment serve as an intact, estrogen replete control group for each study.

All treatments are prepared in 1% tween 80 in normal saline at defined concentrations so that the treatment volume is 0.1 mL/100 g body weight. 17β-estradiol is dissolved in corn oil (20 μg/mL) and delivered subcutaneously, 0.1 mL/rat. All dosages are adjusted at three week intervals according to group mean body weight measurements.

Five weeks after the initiation of treatment and one week prior to the termination of the study, each rat is evaluated for bone mineral density (BMD). The total and trabecular density of the proximal tibia are evaluated in anesthetized rats using an XCT-960M (pQCT; Stratec Medizintechnik, Pforzheim, Germany). The measurements are performed as follows: Fifteen minutes prior to scanning, each rat is anesthetized with an intraperitoneal injection of 45 mg/kg ketamine, 8.5 mg/kg xylazine, and 1.5 mg/kg acepromazine.

The right hind limb is passed through a polycarbonate tube with a diameter of 25 mm and taped to an acrylic frame with the ankle joint at a 90° angle and the knee joint at 180°. The polycarbonate tube is affixed to a sliding platform that maintains it perpendicular to the aperture of the pQCT. The platform is adjusted so that the distal end of the femur and the proximal end of the tibia would be in the scanning field. A two dimensional scout view is run for a length of 10 mm and a line resolution of 0.2 mm. After the scout view is displayed on the monitor, the proximal end of the tibia is located. The pQCT scan is initiated 3.4 mm distal from this point. The pQCT scan is 1 mm thick, has a voxel (three dimensional pixel) size of 0.140 mm, and consists of 145 projections through the slice.

After the pQCT scan is completed, the image is displayed on the monitor. A region of interest including the tibia but excluding the fibula is outlined. The soft tissue is automatically removed using an iterative algorithm. The density of the remaining bone (total density) is reported in $mg/cm^3$. The outer 55% of the bone is peeled away in a concentric spiral. The density of the remaining bone (Trabecular density) is reported in $mg/cm^3$. One week after BMD evaluation the rats are euthanized by carbon dioxide suffocation and blood collected for cholesterol determination. The uteri are removed and the weights taken. Total cholesterol is determined using a Boehringer-Mannheim Hitachi 911 clinical analyzer using the Cholesterol/HP kit. Statistics were compared using one-way analysis of variance with Dunnet's test.

EXAMPLE 65

MCF-7/ERE Antiproliferative Test Procedure

Stock solutions of test compounds (usually 0.1 M) are prepared in DMSO and then diluted 10 to 100-fold with DMSO to make working solutions of 1 or 10 mM. The DMSO stocks are stored at either 4° C. (0.1 M) or −20° C. (<0.1M). MCF-7 cells are passaged twice a week with growth medium [D-MEM/F-12 medium containing 10% (v/v) heat-inactivated fetal bovine serum, 1% (v/v) Penicillin-Streptomycin, and 2 mM glutaMax-1]. The cells are maintained in vented flasks at 37° C. inside a 5% $CO_2$/95% humidified air incubator. One day prior to treatment, the cells are plated with growth medium at 25,000/well into 96 well plates and incubated at 37° C. overnight.

The cells are infected for 2 hr at 37° C. with 50 μl/well of a 1:10 dilution of adenovirus 5-ERE-tk-luciferase in experimental medium [phenol red-free D-MEM/F-12 medium containing 10% (v/v) heat-inactived charcoal-stripped fetal bovine serum, 1% (v/v) Penicillin-Streptomycin, 2 mM glutaMax-1, 1 mM sodium pyruvate]. The wells are then washed once with 150 μl of experimental medium. Finally, the cells are treated for 24 hr at 37° C. in replicates of 8 wells/treatment with 150 μl/well of vehicle (≦0.1% v/v DMSO) or compound that is diluted≧1000-fold into experimental medium.

Initial screening of test compounds is done at a single dose of 1 μM that is tested alone (agonist mode) or in combination with 0.1 nM 17β-estradiol ($EC_{80}$; antagonist mode). Each 96 well plate also includes a vehicle control group (0.1% v/v DMSO) and an agonist control group (either 0.1 or 1 nM 17β-estradiol). Dose-response experiments are performed in either the agonist and/or antagonist modes on active compounds in log increases from $10^{-14}$ to $10^{-5}$ M. From these dose-response curves, $EC_{50}$ and $IC_{50}$ values, respectively, are generated. The final well in each treatment group contains 5 μl of $3\times10^{-5}$ M ICI-182,780 ($10^{-6}$ M final concentration) as an ER antagonist control.

After treatment, the cells are lysed on a shaker for 15 min with 25 μl/well of 1X cell culture lysis reagent (Promega Corporation). The cell lysates (20 μl) are transferred to a 96 well luminometer plate, and luciferase activity is measured in a MicroLumat LB 96 P luminometer (EG & G Berthold) using 100 μl/well of luciferase substrate (Promega Corporation). Prior to the injection of substrate, a 1 second background measurement is made for each well. Following the injection of substrate, luciferase activity is measured for 10 seconds after a 1 second delay. The data are transferred from the luminometer to a Macintosh personal computer and analyzed using the JMP software (SAS Institute); this program subtracts the background reading from the luciferase measurement for each well and then determines the mean and standard deviation of each treatment.

The luciferase data are transformed by logarithms, and the Huber M-estimator is used to down-weight the outlying transformed observations. The JMP software is used to analyze the transformed and weighted data for one-way ANOVA (Dunnett's test). The compound treatments are compared to the vehicle control results in the agonist mode, or the positive agonist control results (0.1 nM 17β-estradiol) in the antagonist mode. For the initial single dose experiment, if the compound treatment results are significantly different from the appropriate control (p<0.05), then the results are reported as the percent relative to the 17β-estradiol control [i.e., ((compound−vehicle control)/(17β-estradiol control−vehicle control))×100]. The JMP software is also used to determine the $EC_{50}$ and/or $IC_{50}$ values from the non-linear dose-response curves.

EXAMPLE 66

Inhibition of LDL Oxidation—Antioxidant Activity

Porcine aortas are obtained from an abattoir, washed, transported in chilled PBS, and aortic endothelial cells are harvested. To harvest the cells, the intercostal vessels of the aorta are tied off and one end of the aorta clamped. Fresh, sterile filtered, 0.2% collagenase (Sigma Type I) is placed in the vessel and the other end of the vessel then clamped to form a closed system. The aorta is incubated at 37° C. for 15-20 minutes, after which the collagenase solution is collected and centrifuged for 5 minutes at 2000×g. Each pellet is suspended in 7 mL of endothelial cell culture medium consisting of phenol red free DMEM/Ham's F12 media supplemented with charcoal stripped FBS (5%), NuSerum (5%), L-glutamine (4 mM), penicillin-streptomycin (1000 U/ml, 100 μg/ml) and gentimicin (75 μg/ml), seeded in 100 mm petri dish and incubated at 37° C. in 5% $CO_2$. After 20 minutes, the cells are rinsed with PBS and fresh medium added, this was repeated again at 24 hours. The cells are confluent after approximately 1 week. The endothelial cells are routinely fed twice a week and, when confluent, trypsinized and seeded at a 1:7 ratio. Cell mediated oxidation of 12.5 μg/mL LDL is allowed to proceed in the presence of the compound to be evaluated (5 μM) for 4 hours at 37° C. Results are expressed as the percent inhibition of the oxidative process as measured by the TBARS (thiobarbituric acid reactive substances) method for analysis of free aldehydes (Yagi K., Biochem Med 15:212-216 (1976)).

EXAMPLE 67

D12 Hypothalmic Cell Test Procedure

D12 rat hypothalamic cells are subcloned from the RCF17 parental cell line and stored frozen. They are routinely grown in DMEM:F12 (1:1), glutaMAX-1 (2 mM), penicillin (100 U/ml)-streptomycin (100 mg/ml), plus 10% fetal bovine serum (FBS). The cells are plated in phenol red-free medium (DMEM:F12, glutaMAX, penicillin-streptomycin) containing 2-10% charcoal stripped FBS at a subconfluent density (1-4×10 6 cells/150 mm dish). The cells are refed 24 h later with medium containing 2% stripped serum. To test for agonist activity, cells are treated with 10 nM 17β-estradiol or various doses of test compound (1 mM or a range from 1 μM to 1 mM). To test for antagonist activity the cells are treated with 0.1 nM 17β-estradiol in the absence or presence of varying doses (100 pM to 1 mM) of test compound. Control dishes are also treated with DMSO as a negative control. Forty-eight hours after hormone addition, the cells are lysed and binding test procedure performed.

For each binding test procedure 100-150 mg protein is incubated with 10 nM $^3$H-R5020+100-fold excess R5020 in a 150 ml volume. Triplicate reactions (three with R5020, three without R5020) are prepared in a 96 well plate. The protein extract is added first followed by $^3$H-R5020 or $^3$H-R5020+ 100× unlabeled R5020. The reaction is performed for 1-2 hr at room temperature. The reaction is stopped by the addition of 100 ml cold 5% charcoal (Norit SX-4), 0.5% dextran 69K (Pharmacia) in TE pH 7.4. After 5 min at room temperature, the bound and unbound ligand are separated by centrifugation (5 min, 1000 RCF, 4° C.). The supernatant solution (−150 ml)

is removed and transferred to a scintillation vial. Following the addition of scintillation fluid (Beckman Ready Protein+), the samples are counted for 1 min in a scintillation counter.

EXAMPLE 68

Progesterone Receptor in the CNS Preoptic Area

Sixty (60) day old female Sprague-Dawley rats are ovariectomized. The animals are housed in an animal care facility with a 12-h light, 12-h dark photoperiod and free access to tap water and rodent chow.

Ovariectomized animals are randomly divided into groups that are injected with vehicle (50% DMSO, 40% PBS, 10% ethanol vehicle), 17β-estradiol (200 ng/kg) or the compound to be tested. Additional animals are injected with the test compound 1 hr prior to injection of 17β-estradiol to evaluate the antagonistic properties of this compound. Six hrs after s.c. injection, animals are euthanized with a lethal dose of $CO_2$ and their brains collected and frozen.

Tissue collected from animals is cut on a cryostat at −16° C. and collected on Silane-coated microscope slides. The section-mounted slides are then dried on a slide warmer maintained at 42° C. and stored in desiccated slide boxes at −80° C. Prior to processing, the desiccated slide boxes are slowly warmed to room temperature (−20° C. for 12-16 hrs; 4° C. for 2 hrs; room temperature for 1 hr) to eliminate condensation formation on slides and thus minimize tissue and RNA degradation. The dry slides are loaded into metal racks, postfixed in 4% paraformaldehyde (pH 9.0) for 5 min and processed as previously described.

A plasmid containing a 815 bp fragment of the rat PR cDNA 9 (ligand binding domain) is linearized and used to generate a S 35-UTP labeled probe that is complimentary to a portion of the rat PR mRNA. Processed section-mounted slides are hybridized with 200 ml of hybridization mix containing the riboprobe ($4\text{-}6\times10^6$ DPM/slide) and 50% formamide and incubated overnight in a 55° C. humidified chamber. In the morning, the slides are placed in metal racks that are immersed in 2×SSC (0.15M NaCl, 0.015M sodium citrate; pH 7.0)/10 mM DTT. The racks are all transferred to a large container and washed in 2×SSC/10 mM DTT for 15 min at RT with gentle agitation. Slides are then washed in RNase buffer at 37° C. for 30 min, treated with RNase A (20 mg/ml) for 30 min at 37° C., and washed for 15 min in room temperature 1×SSC. Subsequently, the slides are washed (2×30 min) in 65° C. in 0.1×SSC to remove nonspecific label, rinsed in room temperature 0.1×SSC for 15 min and dehydrated with a graded series of alcohol: ammonium acetate (70%, 95%, and 100%). Air dried slides are opposed to x-ray film for 3 days and then photographically processed. The slides from all animals are hybridized, washed, exposed and photographically processed together to eliminate differences due to inter-assay variation in conditions.

EXAMPLE 69

Rat Hot Flush—CNS Effects

Ovariectomized-female, 60 day-old Sprague-Dawley rats are obtained following surgery. The surgeries are done a minimum of 8 days prior to the first treatment. The animals are housed individually under 12 h light/dark cycle and given standard rat chow and water ad libitum.

Two control groups are included in every study. Doses are prepared based on mg/kg mean group body weight in either 10% DMSO in sesame oil (sc studies) or in 1.0% tween 80 in saline (po studies). Animals are administered test compounds at doses ranging from 0.01 to 10 mg/kg mean group body weight. Vehicle and ethinyl estradiol (EE) controls (0.1 mg/kg, sc or 0.3 mg/kg, po) control groups are included in each test. When the compounds are tested for their antagonist activity, EE is coadministered at 0.1 or 0.3 mg/kg for sc or po studies, respectively. The test compounds are administered up to the day tail skin temperature is measured.

After the acclimation period of four days, the animals are treated once daily with the compound(s) of interest. There are 10 animals/treatment group. Administration of the compound is either by sc injection of 0.1 ml in the nape of the neck or po in a volume of 0.5 ml. On the 3rd day of treatment, a morphine pellet (75 mg morphine sulfate) is implanted subcutaneously. On the 5th day of treatment, one or two additional morphine pellets are implanted. On the eighth day, approximately half of the animals are injected with Ketamine (80 mg/kg, intramuscularly) and a thermocouple, connected with to a MacLab Data Acquisition System (API Instruments, Milford, Mass.) is taped on the tail approximately one inch from the root of the tail. This system allowed the continuous measurement of tail skin temperature. Baseline temperature is measured for 15 min, then naloxone (1.0 mg/kg) is given sc (0.2 ml) to block the effect of morphine and tail skin temperature is measured for one hour thereafter. On the ninth day, the remaining of the animals are set up and analyzed similarly.

EXAMPLE 70

Vasomotor Function in Isolated Rat Aortic Rings

Sprage-Dawley rats (240-260 grams) are divided into 4 groups:
1. Normal non-ovariectomized (intact)
2. Ovariectomized (ovex) vehicle treated
3. Ovariectomized 17-β estradiol treated (1 mg/kg/day)
4. Ovariectomized animals treated with test compound (i.e., 1 mg/kg/day)

Animals are ovariectomized approximately 3 weeks prior to treatment. Each animal receives 1 mg/kg/day of either 17-β estradiol sulfate or test compound suspended in distilled, deionized water with 1% tween-80 by gastric gavage. Vehicle treated animals received an appropriate volume of the vehicle used in the drug treated groups.

Animals are euthanized by $CO_2$ inhalation and exsanguination. Their thoracic aortas are rapidly removed and placed in 37° C. physiological solution with the following composition (mM): NaCl (54.7), KCl (5.0), $NaHCO_3$ (25.0), $MgCl_2$ $2H_2O$ (2.5), D-glucose (11.8) and $CaCl_2$ (0.2) gassed with $CO_2$—$O_2$, 95%/5% for a final pH of 7.4. The advantitia is removed from the outer surface and the vessel is cut into 2-3 mm wide rings. Rings are suspended in at 10 mL tissue bath with one end attached to the bottom of the bath and the other to a force transducer. A resting tension of 1 gram is placed on the rings. Rings are equilibrated for 1 hour, signals are acquired and analyzed.

After equilibration, the rings are exposed to increasing concentrations of phenylephrine ($10^{-8}$ to $10^{-4}$ M) and the tension recorded. Baths are then rinsed 3 times with fresh buffer. After washout, 200 mM L-NAME is added to the tissue bath and equilibrated for 30 minutes. The phenylephrine concentration response curve is then repeated.

EXAMPLE 71

Eight Arm Radial Arm Maze—Cognition Enhancement

Male Sprague-Dawley, CD rats (Charles River, Kingston, N.Y.) weighing 200-250 g on arrival are used. For one week, the rats are housed, six per cage, with standard laboratory chow and water available ad libitum. Housing is in a colony room maintained at 22° C. and had a 12 hour light/dark cycle with lights on at 6:00 AM. Following habituation to the facility, animals are individually housed and maintained at 85% of free-feeding weight. Once stable weights are attained, the rats are acclimated to the 8-arm radial maze.

The structure of the maze is an adaptation from that of Peele and Baron (Pharmacology, Biochemistry, and Behavior, 29:143-150, 1988). The maze is elevated to a height of 75.5 cm and composed of a circular area surrounded by 8 arms radiating away from the center, equidistant from one another. Each arm is 58 cm long×13 cm high. A clear plexiglass cylinder is oared to enclose the animal in the center portion of the maze prior to the start of each session. Each arm of the maze is equipped with 3 sets of photocells interfaced to a data acquisition unit, which in turn is interfaced to a computer. The photocells are used to track the movement of the rat in the maze. Pellet feeders located above food cups at the end of each arm, dispensed two 45 mg-chocolate pellets when the outer photocell of the arm is activated for the first time in a given session. The maze is located in a testing room with black and white geometric posters on each wall to serve as visual cues. During all training and testing procedures, white noise is audible (~70 db).

The training procedure consists of five phases, each with daily sessions lasting 5 or 10 minutes. A 10 second delay is imposed between the time the rat is placed in the center portion of the maze and when the cylinder is raised to begin the session. During Phase 1, food-restricted pairs of rats are placed on the maze for 10 minutes with 45 mg chocolate food pellets scattered throughout the 8 arms of the maze. During Phase II, each rat is placed individually on the maze for a 10 minute period, with pellets scattered from the middle photocell to the food cup of each arm. During Phase III, each rat is placed on the maze for a 10 minute period, with food pellets located only in and around the food cups in each arm. In Phase IV, each rat is allowed 10 minutes to collect two pellets from each arm. Re-entry into an arm is considered an error. Rats are trained daily in this manner until they achieved criterion performance with less than or equal to 2 total-errors on three consecutive days of training. Total habituation and training time is approximately 3 weeks.

Test compound is prepared in phosphate buffered saline and administered in a volume of 1 ml/kg. Scopolamine HBr (0.3 mg/kg s.c.) served as the impairing agent, producing an increase in error rate (loss of memory). Test compound is given intraperitoneally simultaneously with scopolamine, 30 minutes prior to the first maze exposure on any given test day.

To assess the test compound, an 8×8 balanced latin square for repeated measures is designed, in order to achieve a high experimental efficiency with the least amount of animals. Eight experimental sessions, two per week, are conducted with the 8 treatments (vehicle, scopolamine, 3 doses of test compound in combination with scopolamine) randomized within each session. Each treatment followed every other treatment the same number of times. Therefore, the residual effect of every treatment could be estimated and removed from the direct treatment effect. Following ANOVA, multiple comparisons are performed using Dunnett's two-sided test on adjusted means.

Animals that did not make 4 correct choices within 5 minutes during the first exposure, or that had not made a total of 8 choices by the end of the 2nd exposure, are considered to have "timed-out" for that session. Any animal that "timed-out" following administration of more than one dose of the test compound is excluded from the analysis.

EXAMPLE 72

Neuroprotection

Inhibition of Time-Dependent Death of Cells in Primary Cortical Neuron Cultures

Primary cortical neurons were produced from rat brains that were 0-1 day old using a variation of methods described by Monyer et al. 1989, Brain Research 483:347-354. Dispersed brain tissue was grown in DMEM/10% PDHS (pregnant donor horse serum) for three days and then treated with cytosine arabinoside (ARC) for two days to remove contaminating glial cells. On day 5, the ARC media was removed and replaced with DMEM/10% PDHS. The neuronal cells were cultured for a further 4-7 days before use.

Control primary neuronal cultures show progressive cell death between days 12 and 18 in culture. Twelve cultures were evaluated on days 12 and 16 for levels of the enzyme lactate dehydrogenase (LD) after adding test compound to 6 cultures maintained in DMEM and 10% PDHS on day 9 and maintaining the remaining cultures as controls. LD was assayed using a variation of the method by Wroblewski et al. 1955, Proc. Soc. Exp. Biol. Med. 90:210-213. LD is a cytosolic enzyme which is commonly used in both clinical and basic research to determine tissue viability. An increase in media LD is directly related to cell death.

Neuroprotection Against Cytotoxicity Induced by Hypoglycemia

C6 glioma cells obtained from ATCC were plated in RPMI media with FBS at a concentration of 1×10<6> cells/ml in FALCON 25 cm² tissue culture flasks. Four hours prior to the onset of hypoglycemia, the maintenance media was discarded, monolayers were washed twice in the appropriate media and then incubated for four hours at 37° C. in either serum free or serum free plus test compound. Kreb's Ringer Phosphate buffer was used to wash the monolayers twice before the addition of appropriate glucose treatment. RPMI medium contains 2 mg glucose/ml; flasks were divided into groups of 6 each receiving 100% glucose (2 mg/ml), 80% glucose (1.6 mg/ml), 60% glucose (1.2 mg/ml) or 0% glucose (buffer) or supplemented with test compound. All flasks were incubated for 20 hours and then evaluated for total, live, and dead cell number utilizing trypan blue.

Neuroprotection Against Excitotoxic Amino Acids

Five culture dishes containing SK-N-SH neuroblastoma cells were treated with test compound and 5 culture dishes were treated with RPMI media. Four hours later, all cell were treated with NMDA (500 mu M) for 5 minutes. Total live cells and dead cells were then determined.

Neuroprotection Against Oxygen-Glucose Deprivation

Analysis of pyknotic nuclei to measure apoptosis: Cortical neurons are prepared from E18 rat fetus and plated in 8-well chamber slides precoated with poly-D-lysine (10 ng/ml) and serum at a density of 100,000 cells/well. Cells are plated in high glucose DMEM containing 10% FCS and kept in the incubator at 37° C. with 10% $CO_2$/90% air. On the next day, serum is removed by replacing culture media with high glucose DMEM containing B27 supplement and cells are kept in the incubator without further media change until the day of experiment. On day 6, slides are divided into two groups; control group and OGD group. Cells in control group receive DMEM with glucose and custom B27 (without antioxidants). Cells in OGD group receive no-glucose DMEM with custom B27, which has been degassed under vacuum for 15 min. Cells are flushed with 90% $N_2$/10% $CO_2$ for 10 min in an airtight chamber and incubated at 37° C. for 6 hrs. After 6 hrs, both control and OGD cells are subject to replacement of media containing either vehicle (DMSO) or test compound in glucose-containing DMEM with custom B27. Cells are returned to normoxic incubator at 37° C. After 24 hrs, cells are fixed in 4% PFA for 10 min at 4° C. and stained with Topro (Fluorescent nuclear binding dye). Apoptosis is assessed using Laser Scanning Cytometer by measuring pyknotic nuclei.

Measurement of LDH release as an indication of cell death: Cortical neurons are prepared from E18 rat fetus and plated in 48-well culture plates precoated with poly-D-lysine (10 ng/ml) and serum at a density of 150,000 cells/well. Cells are plated in high glucose DMEM containing 10% FCS and kept in the incubator at 37° C. with 10% $CO_2$/90% air. On the next day, serum is removed by replacing culture media with high glucose DMEM containing B27 supplement. On day 6, cells are divided into two groups; control group and OGD group. Cells in control group receive DMEM with glucose and custom B27 (without antioxidants). Cells in OGD group receive no-glucose DMEM with custom B27, which has been degassed under vacuum for 15 min. Cells are flushed with 90% $N_2$/10% $CO_2$ for 10 min in an airtight chamber and incubated at 37° C. for 6 hrs. After 6 hrs, both control and OGD cells are subject to replacement of media containing either vehicle (DMSO) or test compound in glucose-containing DMEM with custom B27. Cells are returned to normoxic incubator at 37° C. After 24 hrs, cell death is assessed by measuring cellular release of LDH (lactate dehydrogenase) into the culture medium. For LDH assay, an aliquot of 50 µl culture medium is transferred into the 96 well plate. After the addition of 140 µl 0.1M potassium phosphate buffer (pH 7.5) and 100 µl 0.2 mg/ml NADH, the plate is let sit in the dark at room temperature for 20 min. The reaction is initiated by the addition of 10 µl of sodium pyruvate. The plate is read immediately at 340 nM in a Thermomax plate reader (Molecular Devices). The absorbance, an index of NADH concentration, is recorded every 6 seconds for 5 minutes and the slope indicating the rate of NADH disappearance is used to calculate LDH activity.

LDH Activity(U/ml)=($\Delta$A/min) (TCF)(20) (0.0833)/(0.78)

where: 0.0833=proportionality constant 0.78=instrument light path length (cm)

EXAMPLE 73

HLA Rat Test Procedure—Crohn's Disease and Inflammatory Bowel Disorders

Male HLA-B27 rats are obtained from Taconic and provided unrestricted access to a food (PMI Lab diet 5001) and water. At the start of the study, rats are 22-26 weeks old.

Rats are dosed subcutaneously once per day for seven days with one of the formulations listed below. There are five rats in each group and the last dose is administered two hours before euthanasia.

vehicle (50% DMSO/50% Dulbecco's PBS)

17α-ethinyl-17β-estradiol (10 µg/kg)

test compound

Stool quality is observed daily and graded according to the following scale: Diarrhea=3; soft stool=2; normal stool=1. At the end of the test procedure, serum is collected and stored at −70° C. A section of colon is prepared for histological analysis and an additional segment is analyzed for myeloperoxidase activity.

The following method is used to measure myeloperoxidase activity. Colon tissue is harvested and flash frozen in liquid nitrogen. A representative sample of the entire colon is used to ensure consistency between samples. The tissue is stored at −80° C. until use. Next, the tissue is weighed (approximately 500 mg) and homogenized in 1:15 w/v of 5 mM $H_2 KPO_4$ (pH 6) washing buffer. The tissue is spun down at 20,000×g in a Sorvall RC 5B centrifuge for 45 minutes at 2-8° C. Supernatant is then discarded. Tissue is resuspended and homogenized in 2.5 ml (1:5 w/v) of 50 mM $H_2 KPO_4$ with 10 mM EDTA and 0.5% Hex Ammonium Bromide to help solubilize the intracellular MPO. Tissue is frozen in liquid Nitrogen, thawed in a 37° C. water bath and sonicated for 15 seconds to ensure membrane lysis. This procedure is repeated 3 times. Samples are then kept on ice for 20 minutes and centrifuged at 12,000×g for 15 minutes at 2-8° C. The supernatant is analyzed following these steps.

The test mixture is prepared by adding 2.9 ml of 50 mM $H_2 KPO_4$ with 0.167 O-Dianisidine/ml with 0.0005% $H_2O_2$ into a reaction tube. When hydrogen peroxide is degraded, O-Dianisidine is oxidized and absorbs at 460 nm in a concentration dependent manner. The mixture is heated to 25° C. One hundred (100) µL of the tissue supernatant is added to the reaction tube, incubated for one minute at 25° C., then 1 ml is transferred to a disposable plastic cuvette. OD is measured every 2 minutes reaction time at 460 nm against a blank containing 2.9 ml of the reaction mixture and 100 µl of the 0.5% ammonium bromide solution.

Enzyme activity units are quantified by comparison of absorbence @ 460 to a standard curve prepared with purified human MPO 31.1 Units/Vial. The MPO is reconstituted and serially diluted using 50 mM $H_2 KPO_4$ with 10 mM EDTA and 0.5% Hex Ammonium Bromide to four known concentrations. Sample absorbencies are compared against this curve to determine activity.

Histological analysis is performed as follows. Colonic tissue is immersed in 10% neutral buffered formalin. Each specimen of colon is separated into four samples for evaluation. The formalin-fixed tissues are processed in a vacuum infiltration processor for paraffin embedding. The samples are sectioned at 5 µm and then stained with hematoxylin and eosin (H&E) for blinded histologic evaluations using a scale modified after Boughton-Smith. After the scores are completed the samples are unblinded, and data are tabulated and analyzed by ANOVA linear modeling with multiple mean comparisons.

Based on the results obtained in the standard pharmacological test procedure, the compounds of this invention are estrogen receptor modulators useful in the treatment or inhibition of conditions, disorders, or disease states that are at least partially mediated by an estrogen deficiency or excess, or which may be treated or inhibited through the use of an estrogenic agent. The compounds of this invention are particularly useful in treating a peri-menopausal, menopausal, or postmenopausal patient in which the levels of endogenous estrogens produced are greatly diminished. Menopause is generally defined as the last natural menstrual period and is characterized by the cessation of ovarian function, leading to the substantial diminution of circulating estrogen in the bloodstream. As used herein, menopause also includes conditions of decreased estrogen production that may be surgically, chemically, or be caused by a disease state which leads to premature diminution or cessation of ovarian function.

Accordingly, the compounds of this invention are useful in treating or inhibiting osteoporosis and in the inhibition of bone demineralization, which may result from an imbalance in a individual's formation of new bone tissues and the resorption of older tissues, leading to a net loss of bone. Such bone depletion results in a range of individuals, particularly in post-menopausal women, women who have undergone bilateral oophorectomy, those receiving or who have received extended corticosteroid therapies, those experiencing gonadal dysgenesis, and those suffering from Cushing's syndrome. Special needs for bone, including teeth and oral bone, replacement can also be addressed using these compounds in individuals with bone fractures, defective bone structures, and those receiving bone-related surgeries and/or the implantation of prosthesis. In addition to those problems described above, these compounds can be used in treatment or inhibition for osteoarthritis, hypocalcemia, hypercalcemia, Paget's disease, osteomalacia, osteohalisteresis, multiple myeloma and other forms of cancer having deleterious effects on bone tissues.

The compounds of this invention are also useful in treating or inhibiting benign or malignant abnormal tissue growth, including prostatic hypertrophy, uterine leiomyomas, breast cancer, endometriosis, endometrial cancer, polycystic ovary syndrome, endometrial polyps, benign breast disease, adenomyosis, ovarian cancer, melanoma, prostrate cancer, cancers of the colon, CNS cancers, such as glioma or astioblastomia.

The compounds of this invention are cardioprotective and they are useful in lowering cholesterol, triglycerides, Lp(a), and LDL levels; inhibiting or treating hypercholesteremia; hyperlipidemia; cardiovascular disease; atherosclerosis; peripheral vascular disease; restenosis, and vasospasm; and inhibiting vascular wall damage from cellular events leading toward immune mediated vascular damage. These cardiovascular protective properties are of great importance when treating postmenopausal patients with estrogens to inhibit osteoporosis and in the male when estrogen therapy is indicated.

The compounds of this invention are also antioxidants, and are therefore useful in treating or inhibiting free radical induced disease states. Specific situations in which antioxidant therapy is indicated to be warranted are with cancers, central nervous system disorders, Alzheimer's disease, bone disease, aging, inflammatory disorders, peripheral vascular disease, rheumatoid arthritis, autoimmune diseases, respiratory distress, emphysema, prevention of reperfusion injury, viral hepatitis, chronic active hepatitis, tuberculosis, psoriasis, systemic lupus erythematosus, adult respiratory distress syndrome, central nervous system trauma and stroke.

The compounds of this invention are also useful in providing cognition enhancement, and in treating or inhibiting senile dementias, Alzheimer's disease, cognitive decline, neurodegenerative disorders, providing neuroprotection or cognition enhancement.

The compounds of this invention are also useful in treating or inhibiting inflammatory bowel disease, ulcerative proctitis, Crohn's disease, and colitis; menopausal related conditions, such as vasomotor symptoms including hot flushes, vaginal or vulvar atrophy, atrophic vaginitis, vaginal dryness, pruritus, dyspareunia, dysuria, frequent urination, urinary incontinence, urinary tract infections, vasomotor symptoms, including hot flushes, myalgia, arthralgia, insomnia, irritability, and the like; male pattern baldness; skin atrophy; acne; type II diabetes; dysfunctional uterine bleeding; and infertility.

The compounds of this invention are useful in disease states where amenorrhea is advantageous, such as leukemia, endometrial ablations, chronic renal or hepatic disease or coagulation diseases or disorders.

The compounds of this invention can be used as a contraceptive agent, particularly when combined with a progestin.

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. Effective administration of the compounds of this invention may be given at an oral dose of from about 0.1 mg/day to about 1,000 mg/day. Preferably, administration will be from about 10 mg/day to about 600 mg/day, more preferably from about 50 mg/day to about 600 mg/day, in a single dose or in two or more divided doses. The projected daily dosages are expected to vary with route of administration.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally.

Oral formulations containing the active compounds of this invention may comprise any conventionally used oral forms, including tablets, capsules, buccal forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthan gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or a fruit juice, containing appropriate solubilizers or emulsifiers as needed.

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature.

Suppository formulations may be made from traditional materials, including cocoa butter, with or without the addition of waxes to alter the suppository's melting point, and glycerin. Water soluble suppository bases, such as polyethylene glycols of various molecular weights, may also be used.

All patents, publications, and other documents cited herein are hereby incorporated by reference in their entirety.

What is claimed is:

1. A method of lowering cholesterol, triglycerides, Lp(a), or LDL levels; or inhibiting hypercholesteremia; or hyperlipidemia; comprising providing to said mammal an effective amount of a compound of the formula:

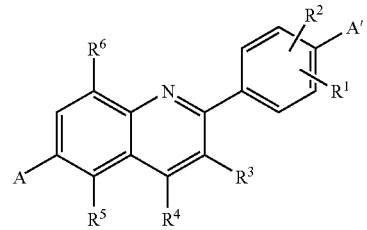

I wherein:
  A and A' are each, independently, OH or OP;
  P is alkyl, alkenyl, benzyl, acyl, aroyl, alkoxycarbonyl, sulfonyl or phosphoryl;
  $R^1$ and $R^2$ are each, independently, H, halogen, $C_1$-$C_6$ alkyl, $C_2$-$C_7$ alkenyl, or $C_1$-$C_6$ alkoxy;
  $R^3$ is H, halogen, or $C_1$-$C_6$ alkyl;
  $R^4$, $R^5$ and $R^6$ are each, independently, H, halogen, $C_1$-$C_6$ alkyl, $C_2$-$C_7$ alkenyl, $C_2$-$C_7$ alkynyl, $C_3$-$C_7$ cycloalkyl, $C_1$-$C_6$ alkoxy, —CN, —CHO, acyl, phenyl, aryl or heteroaryl;
  wherein the alkyl or alkenyl moieties of $R^4$, $R^5$ or $R^6$ may be optionally substituted with halogen, OH, —CN, trifluroalkyl, trifluoroalkoxy, —NO$_2$, or phenyl;
  wherein the alkynyl moiety of $R^4$, $R^5$ or $R^6$ may be optionally substituted with halogen, —CN, —CHO, acyl, trifluroalkyl, trialkylsilyl, or optionally substituted phenyl;
  wherein the phenyl moiety of $R^4$, $R^5$ or $R^6$ may be optionally mono-, di-, or tri-subsitituted with halogen, $C_1$-$C_6$ alkyl, $C_2$-$C_7$ alkenyl, OH, $C_1$-$C_6$ alkoxy, —CN, —CHO, —NO$_2$, amino, $C_1$-$C_6$ alkylamino, di-($C_1$-$C_6$)alkylamino, thiol, or $C_1$-$C_6$ alkylthio;
or a N-oxide thereof or a pharmaceutically acceptable salt thereof or a prodrug thereof.

* * * * *

UNITED STATES PATENT AND TRADEMARK OFFICE
CERTIFICATE OF CORRECTION

| | | |
|---|---|---|
| PATENT NO. | : 7,632,845 B2 | Page 1 of 1 |
| APPLICATION NO. | : 11/443861 | |
| DATED | : December 15, 2009 | |
| INVENTOR(S) | : Vu et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 537 days.

Signed and Sealed this

Second Day of November, 2010

David J. Kappos
*Director of the United States Patent and Trademark Office*